US010072090B2

(12) United States Patent
Siu et al.

(10) Patent No.: US 10,072,090 B2
(45) Date of Patent: Sep. 11, 2018

(54) HUMAN ANTI-B7RP1 NEUTRALIZING ANTIBODIES

(71) Applicants: AMGEN INC., Thousand Oaks, CA (US); E. R. SQUIBB & SONS, L.L.C., Princeton, NJ (US)

(72) Inventors: Gerald Siu, Santa Monica, CA (US); Wenyan Shen, Thousand Oaks, CA (US); Steven K. Yoshinaga, Thousand Oaks, CA (US); Haichun Huang, Fremont, CA (US)

(73) Assignees: AMGEN INC., Thousand Oaks, CA (US); MEDAREX INC., Princeton, NJ (US)

( * ) Notice: Subject to any disclaimer, the term of this patent is extended or adjusted under 35 U.S.C. 154(b) by 228 days.

(21) Appl. No.: 14/995,983

(22) Filed: Jan. 14, 2016

(65) Prior Publication Data
US 2016/0145345 A1    May 26, 2016

Related U.S. Application Data

(60) Continuation of application No. 13/794,265, filed on Mar. 11, 2013, now Pat. No. 9,266,945, which is a division of application No. 12/976,802, filed on Dec. 22, 2010, now Pat. No. 8,981,071, which is a division of application No. 11/458,260, filed on Jul. 18, 2006, now Pat. No. 7,868,140.

(60) Provisional application No. 60/700,265, filed on Jul. 18, 2005.

(51) Int. Cl.
C07K 16/28 (2006.01)
A61K 39/395 (2006.01)
C07K 16/18 (2006.01)
A61K 39/00 (2006.01)

(52) U.S. Cl.
CPC .......... *C07K 16/2896* (2013.01); *C07K 16/18* (2013.01); *C07K 16/2827* (2013.01); *A61K 2039/505* (2013.01); *C07K 2317/20* (2013.01); *C07K 2317/21* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,399,216 A | 8/1983 | Axel et al. |
| 4,740,461 A | 4/1988 | Kaufman |
| 4,816,397 A | 3/1989 | Boss et al. |
| 4,912,040 A | 3/1990 | Kaufman et al. |
| 4,946,778 A | 8/1990 | Ladner et al. |
| 4,959,455 A | 9/1990 | Clark et al. |
| 5,151,510 A | 9/1992 | Stec et al. |
| 5,260,203 A | 11/1993 | Ladner et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,625,825 A | 4/1997 | Rostoker et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 6,180,370 B1 | 1/2001 | Queen et al. |
| 6,521,749 B1 | 2/2003 | Ling et al. |
| 6,984,720 B1 | 1/2006 | Korman et al. |
| 7,271,245 B2 | 9/2007 | Felding-Habermann et al. |
| 7,435,796 B1 | 10/2008 | Yoshinaga |
| 7,521,532 B2 | 4/2009 | Dunussi-Joannopoulos et al. |
| 7,601,813 B2 | 10/2009 | Ling et al. |

(Continued)

FOREIGN PATENT DOCUMENTS

| | | |
|---|---|---|
| EP | 0 036 676 A1 | 9/1981 |
| EP | 0058481 A1 | 8/1982 |

(Continued)

OTHER PUBLICATIONS

Panka et al. 1988, Proc. Natl. Acad. Sci. USA, 85: 3080-3084.*
Beiboer et al., J. Mol. Biol. (2000), 296: 833-849.*
Klimka et al., British Journal of Cancer (2000), 83: 252-260.*
Rader et al., Proc. Natl. Acad. Sci. USA (1998), 95: 8910-8915.*
Xu et al., Immunity (2000), 13: 37-45.*
Abrams et al., Blockade of T lymphocyte costimulation with cytotoxic T lymphocyte-associated antigen 4-immunoglobulin (CTLA4Ig) reverses the cellular pathology of psoriatic plaques, including the activation of keratinocytes, dendritic cells, and endothelial cells, *J Exp Med.*, 192(5): 681-94 (2000).

(Continued)

*Primary Examiner* — Ilia I Ouspenski
(74) *Attorney, Agent, or Firm* — Marshall, Gerstein & Borun LLP

(57) ABSTRACT

This invention provides antibodies that interact with or bind to human B7 related protein-1 (B7RP1) and antibodies that bind to and neutralize the function of B7RP1 thereby. The invention also provides pharmaceutical compositions of said antibodies and methods for neutralizing B7RP1 function, and particularly for treating immune disorders (e.g., inappropriate immune response) by administering a pharmaceutically effective amount of anti-B7RP1 antibodies. Methods of detecting the amount of B7RP1 in a sample using anti-B7RP1 antibodies are also provided.

12 Claims, 17 Drawing Sheets
Specification includes a Sequence Listing.

(56) References Cited

U.S. PATENT DOCUMENTS

| | | | |
|---|---|---|---|
| 7,708,993 B2 | 5/2010 | Yoshinaga et al. | |
| 7,868,140 B2 * | 1/2011 | Siu | C07K 16/2827 424/130.1 |
| 8,470,317 B2 * | 6/2013 | Yoshinaga | C07K 14/705 424/130.1 |
| 8,981,071 B2 * | 3/2015 | Siu | C07K 16/2827 435/320.1 |
| 9,266,945 B2 * | 2/2016 | Siu | C07K 16/2827 |
| 2011/0104757 A1 | 5/2011 | Siu et al. | |

FOREIGN PATENT DOCUMENTS

| | | |
|---|---|---|
| EP | 88046 A2 | 9/1983 |
| EP | 0 133 988 A2 | 3/1985 |
| EP | 0 143 949 A1 | 6/1985 |
| EP | 1374902 A1 | 1/2004 |
| WO | WO-1988/001649 A1 | 3/1988 |
| WO | WO-1990/14363 A1 | 11/1990 |
| WO | WO-1992/03918 A1 | 3/1992 |
| WO | WO-1992/22646 A1 | 12/1992 |
| WO | WO-1993/12227 A1 | 6/1993 |
| WO | WO-1993/15722 A1 | 8/1993 |
| WO | WO-1994/20069 A1 | 9/1994 |
| WO | WO-1998/24884 A1 | 6/1998 |
| WO | WO-1998/24893 A2 | 6/1998 |
| WO | WO-2000/24782 A2 | 5/2000 |
| WO | WO-2000/46240 A2 | 8/2000 |
| WO | WO-2000/56772 A1 | 9/2000 |
| WO | WO-2001/09187 A2 | 2/2001 |
| WO | WO-2002/04364 A2 | 1/2002 |
| WO | WO-2002/44364 A2 | 6/2002 |
| WO | WO-2004/43989 A2 | 5/2004 |
| WO | WO-2004/106380 A2 | 12/2004 |
| WO | WO-2006/003999 A1 | 1/2006 |

OTHER PUBLICATIONS

Abrams et al., CTLA4lg-mediated blockade of T-cell costimulation in patients with *Psoriasis vulgaris*, *J. Clin. Invest.*, 103(9): 1243-52 (1999).

Adamczyk et al., Application of surface plasmon resonance toward studies of low-molecular-weight antigen-antibody binding interactions, *Methods*, 20(3): 319-28 (2000).

Adamczyk et al., Surface plasmon resonance (SPR) as a tool for antibody conjugate analysis, *Bioconjugate Chem.*, 10: 1032-37 (1999).

Adames et al., The c-myc oncogene driven by immunoglobulin enhancers induces lymphoid malignancy in transgenic mice, *Nature*, 318: 533-38 (1985).

Alexander et al., Expression of the c-myc oncogene under control of an immunoglobulin enhancer in E mu-myc transgenic mice, *Mol. Cell. Biol.*, 7(4): 1436-44 (1987).

Ausubel et al., Current Protocols in Molecular Biology, Greene Publishing Associates (1987) [Table of Contents].

Benoist et al., In vivo sequence requirements of the SV40 early premotor region, *Nature*, 290(5804): 304-10 (1981).

Blazer et al., Infusion of anti-B7.1 (CD80) and anti-B7.2 (CD86) monoclonal antibodies inhibits murine graft-versus-host disease lethality in part via direct effects on CD4+ and CD8+ T cells. *J. Immunol.*, 157: 3250-9 (1996).

Boerner et al., Production of antigen-specific human monoclonal antibodies from in vitro-primed human splenocytes, *J. Immunol.*, 147(1): 86-95 (1991).

Brinster et al., Regulation of metallothionein-thymidine kinase fusion plasmids injected into mouse eggs, *Nature*, 296(5852): 39-42 (1982).

Bruggemann et al., Designer mice: The production of human antibody repertoires in transgenic animals, *Year Immun.*, 7:33-40 (1993).

Burton et al., Human antibody effector function, *Adv. Immunol.*, 51: 1-84 (1992).

Chen et al., Immunoglobulin gene rearrangement in B cell deficient mice generated by targeted deletion of the JH locus, *Int. Immunol.*, 5(6): 647-56 (1993).

Chu et al., SV40 DNA transfection of cells in suspension: Analysis of efficiency of transcription and translation of T-antigen, *Gene*, 13(2): 197-202 (1981).

Cole et al., The EBV-hybridoma technique and its application to human lung cancer, *Monoclonal Antibodies and Cancer Therapy*, Alan R. Liss, p. 77 (1985).

Colman et al., Effects of amino acid sequence changes on antibody-antigen interactions, *Res. Immunol.*, 145: 33-6 (1994).

Coyle et al., The CD28-related molecule ICOS is required for effective T cell-dependent immune responses, *Immunity*, 13(1):95-105 (2000).

Davis et at., Basic Methods in Molecular Biology, Elsevier (1986) [Table of Contents].

DeBoer et al., The tac promoter: A functional hybrid derived from the trp and lac promoters, *Proc. Nati Acad. Sci. USA*, 80: 21-5 (1983).

DePascalis, Grafting of "abbreviated" complementarity-determining regions containing specificity-determining residues essential for ligand contact to engineer a less immunogenic humanized monoclonal antibody, *J. Immunol.*, 169: 3076-84 (2002).

Dong et al., Regulation of immune and autoimmune responses by ICOS, *J. Autoimmun.*, 21: 255-60 (2003).

Eppstein et al., Biological activity of liposome-encapsulated murine interferon gamma is mediated by a cell membrane receptor, *Proc. Natl. Acad. Sci. USA*, 82(11): 3688-92 (1985).

Fishwild et al., High-avidity human IgG kappa monoclonal antibodies from a novel strain of minilocus transgenic mice, *Nat. Biotechnol.*, 14(7): 845-51 (1996).

Frisque et al., Infectivity of the DNA from four isolates of JC virus, *Virology*, 32(2): 476-82 (1973).

Goeddel, Systems for heterologous gene expression. *Meth. Enzymol.*, 185: 3-7 (1990) [Table of Contents].

Graham et al., A new technique for the assay of infectivity of human adenovirus 5 *Virology*, 52(2): 456-67 (1973).

Grosschedl et al., Introduction of a mu immunoglobulin gene into the mouse germ line: Specific expression in lymphoid cells and synthesis of functional antibody, *Cell*, 38(3):647-58 (1984).

Hammer et al., Diversity of alpha-fetoprotein gene expression in mice is generated by a combination of separate enhancer elements, *Science*, 235(4784): 53-8 (1987).

Hanahan, Heritable formation of pancreatic beta-cell tumours in transgenic mice expressing recombinant insulin/simian virus 40 oncogenes, *Nature*, 315(6015): 115-22 (1985).

Harding et al., Class switching in human immunoglobulin transgenic mice, *Ann. N.Y. Acad. Sci.*, 764: 536-46 (1995).

Holm et al., Functional mapping and single chain construction of the anti-cytokeratin 8 monoclonal antibody TS1, *Mol. Immunol.*, 44(6): 1075-84 (2007).

Hoogenboom et al., By-passing immunisation. Human antibodies from synthetic repertoires of germline VH gene segments rearranged in vitro, J. *Mol. Biol.*, 227(2): 381-8 (1992).

Hu et al., B7RP-1 blockade ameliorates autoimmunity through regulation of follicular helper T cells, *J. Immunol.*, 182: 1421-8 (2009).

Iwahi et al., Amelioration of collagen-included arthritis by blockade of inducible costimulator-B7 homologous protein costimulation-B7 homologous protein costimulation, *J. Immunol.*, 4332-9 (2002).

Jakobovits et al., Analysis of homozygous mutant chimeric mice: deletion of the immunoglobulin heavy-chain joining region blocks B-cell development and antibody production, *Proc. Natl. Acad. Sci. USA*, 90(6): 2551-5 (1993).

Jakobovits et al., Germ-line transmission and expression of a human-derived yeast artificial chromosome, *Nature*, 362(6417): 255-8 (1993).

Kelsey et al., Species-and tissue-specific expression of human alpha 1-antitrypsin in transgenic mice, *Genes Devel.*, 1(2): 161-71 (1987).

Khayyamian et al., Species and tissue-specific expression of human alpha 1-antitrypsin in transgenic mice, *Genes Devel.*, 1(2):161-71 (19870.

(56) References Cited

OTHER PUBLICATIONS

Kimmel et al., Preparation of cDNA and the generation of cDNA libraries: Overview. *Meth. Enzymol.*, 152: 307-16 (1987).
Kohler et al., Continuous cultures of fused cells secreting antibody of predefined specificity, *Nature*, 256(5517): 495-7 (1975).
Kollias et al., Regulated expression of human A gamma-, beta-, and hybrid gamma beta-globin genes in transgenic mice: manipulation of the developmental expression patterns, *Cell*, 46(1): 89-94 (1986).
Kostelny et al., Formation of a bispecific antibody by the use of leucine zippers, *J. Immunol.*, 148(5): 1547-53 (1992).
Kremer et al., Treatment of rheumatoid arthritis by selective inhibition of T-cell activation with fusion protein CTLA4Ig, *New Eng. J. Med.*, 349(20): 1907-15 (2003).
Krumlauf et al., Developmental regulation of alpha-fetoprotein genes in transgenic mice, *Mol. Cell. Biol.*, 5(7): 1639-48 (1985).
Langer et al., Biocompatibility of polymeric delivery systems for macromolecules, *J. Biomed. Mater. Res.*, 15: 167-277 (1981).
LaPlanche et al., Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates, *Nucl. Acids Res.*, 14(22): 9081-93 (1986).
Leder et al., Consequences of widespread deregulation of the c-myc gene in transgenic mice: multiple neoplasms and normal development, *Cell*, 45(4): 485-95 (1986).
Lonberg et al., Antigen-specific human antibodies from mice comprising four distinct genetic modifications, *Nature*, 368(6474): 856-9 (1994).
Lonberg et al., Human antibodies from transgenic mice, *Intern. Rev. Immunol.*, 13(1): 65-93 (1995).
Lonberg, Transgenic approaches to human monoclonal antibodies, *Handbook of Experimental Pharmacology*, 113: 49-101 (1994).
MacCallum et al., Antibody-antigen Interactions: Contact analysis and finding site topography, *J. Mol. Biol.*, 262(5): 732-45 (1996).
MacDonald, Expression of the pancreatic elastase I gene in transgenic mice, *Hepatology*, 7(1 Suppl): 42S-51S (1987).
Marks et al., By-passing immunization. Human antibodies from V-gene libraries displayed on phage, *J. Mol. Biol.*, 222(3): 581-97 (1991).
Mason et al., The hypogonadal mouse: Reproductive functions restored by gene therapy, *Science*, 234: 1372-78 (1986).
Medesan et al., Comparative studies of rat IgG to further delineate the Fc:FcRn interaction site, *Eur. J. Immunol.*, 28(7): 2092-100 (1998).
Mendez et al., Functional transplant of megabase human immunoglobulin loci recapitulates human antibody response in mice, *Nat. Genet.*, 15(2): 146-56 (1997).
Mogram et al., Developmental regulation of a cloned adult beta-globin gene in transgenic mice, *Nature*, 315(6017): 338-40 (1985).
Ornitz et al., Elastase I promoter directs expression of human growth hormone and SV40 T antigen genes to pancreatic acinar cells in transgenic mice, *Cold Spring Harbor Symp. Quant Biol.* 50: 399-409 (1986).
Pinkert et al., An albumin enhancer located 10 kb upstream functions along with its promoter to direct efficient, liver-specific expression in transgenic mice, *Genes Devel.*, 1(3): 268-76 (1987).
Proteins, Structures and Molecular Principles, (Creighton, Ed.), W. H. Freeman and Company, New York (1984) [Table of Contents].
Ravetch et al., IgG Fc receptors, *Annu. Rev. Immunol.*, 19: 275-90 (2001).
Readhead et al., Expression of a myelin basic protein gene in transgenic shiverer mice: Correction of the dysmyelinating phenotype, *Cell*, 48(4): 703-12 (1987).
Remington's Pharmaceutical Sciences, 18th Edition, (A. R. Gennaro, Ed.), Mack Publishing Company (1990) [Table of Contents].
Richter et al., Tumor necrosis factor-alpha regulates the expression of inducible costimulator receptor ligand on CD34+ progenitor cells during differentiation into antigen presenting cells, *J. Biol. Chem.*, 276(49): 45686-93 (2001).
Rudikoff et al., Single amino acid substitution altering antigen-binding specificity, *Proc. Natl. Acad. Sci. USA*. 79: 1979-83 (1982).
Sambrook et al., Molecular Cloning, A Laboratory Manual, Cold Spring Harbor Laboratories (2001) [Table of Contents].
Sani Tissue-specific expression of rat myosin light-chain 2 gene in transgenic mice, *Nature*, 314: 283-86 (1985).
Shields et al., High resolution mapping of the binding site on human IgG1 for Fc gamma RI, Fc gamma RII, Fc gamma RIII, and FcRn and design of IgG1 variants with improved binding to the Fc gamma R, *J. Biol. Chem.*, 276(9): 6591-604 (2001).
Sidman et al., Controlled release of macromolecules and pharmaceuticals from synthetic polypeptides based on glutamic acid, *Biopolymers*, 22(1): 547-56 (1983).
Songsivilai et al., Bispecific antibody: A tool for diagnosis and treatment of disease, *Clin. Exp Immunol.*, 79(3): 315-21 (1990).
Stec et al., Automated solid phase synthesis, separation and stereochemistry of phosphothioate analogues of oligodeoxyribonucleotides, *J. Am. Chem. Soc.*, 106: 6077 (1984).
Stein et al., Physicochemical properties of phosphorothioate oligodeoxynucleotides, *Nucl. Acids Res.*, 16(8):3209-21 (1988).
Swift et al., Tissue-specific expression of the rat pancreatic elastase I gene in transgenic mice, *Cell*, 38(3): 639-46 (1984).
Taylor et al., A transgenic mouse that expresses a diversity of human sequence heavy and light chain immunoglobulins, *Nucl. Acids Res.*, 20(23): 6287-95 (1992).
Taylor et al., Human immunoglobulin transgenes undergo rearrangement, somatic mutation and class switching in mice that lack endogenous IgM, *Int. Immunol.*, 6(4): 579-91 (1994).
Telleman et al., The role of the Brambell receptor (FcRB) in liver: protection of endocytosed immunoglobulin G (IgG) from catabolism in hepatocytes rather than transport of IgG to bile, *Immunology*, 100(2): 245-51 (2000).
Thomsen et al., Promoter-regulatory region of the major immediate early gene of human cytomegalovirus, *Proc. Natl. Acad. Sci. USA*, 81(3): 659-63 (1984).
Thornton et al., Protein structure: Prediction of progress at last, *Nature*, 354(6349): 105-6 (1991).
Totsuka et al., Amerliorating effect of anti-inducible costimulator monoclonal antibody in a murine model of chronic cloitis, *Gastroenterology*, 410-21 (2003).
Tuaillon et al. Biased utilization of DHQ52 and JH4 gene segments in a human Ig transgenic minilocus is independent of antigenic selection, *J. Immunol.*, 152(6): 2912-20 (1994).
Vajdos et al., Comprehensive functional maps of the Antigen-binding site of an anti-ErbB2 antibody obtained with shotgun scanning mutagensis, *J. Mol. Biol.*, 320(2): 415-28 (2002).
Villa-Kamaroff et al., A bacterial clone synthesizing proinsulin, *Proc. Natl. Acad. Sci U.S.A.*, 75: 3727-31 (1978).
Wagner et al.: Nucleotide sequence of the thymidine kinase gene of herpes simplex virus type 1, *Proc. Natl. Acad. Sci. U.S.A.*, 78: 1441-5 (1981).
Wahl et al., Interaction of B&RP1 with ICOS negatively regulates antigen presentation by B cells, *Inflammation*, 27(4): 191-200 (2003).
Wahl et al., Molecular hybridization of immobilized nucleic acids: theoretical concepts and practical considerations, *Methods Enzymol.*, 152: 399-407 (1987).
Wahl et al., Renal tubular epithelial expression of the costimulatory molecule B7RP-1 (Inducible Costimulator Ligand), *J. Am. Soc. Nephrol.*, 13: 1517-26 (2002).
Wu et al., Humanization of a murine monoclonal antibody by simultaneous optimization of framework and CDR residues, *J. Mol. Biol.*, 294: 151-62 (1999).
Yamamoto et al., Identification of a functional promoter in the long terminal repeat of Rous sarcoma virus, *Cell*, 22(3): 787-97 (1980).
Yoshinaga et al., T-cell co-stimulation through B7RP-1 and ICOS, *Nature*, 402(6763): 827-32 (1999).
Yoshinga et al., Characterization of a new human B7-related protein: B7RP-1 is the ligand to the co-stimulatory protein ICOS, *Int. Immun.*, 12(10): 1439-47 (2000).
Zola, Using monoclonal antibodies: Soluble antigens. Monoclonal Antibodies: A Manual of Techniques, *CRC Press*, pp. 147-158 (1987).

(56) References Cited

OTHER PUBLICATIONS

Zon et al., Phosphorothioate oligonucleotides: Chemistry, purification, analysis, scale-up and future directions, *Anti-Cancer Drug Design*, 6(6): 539-68 (1991).

Zou et al., Gene targeting in the Igx locus: Efficient generation of I chain-expressing B cells, independent of gene rearrangements in Igx, *EMBO J.*, 12:811-20 (1993).

* cited by examiner

```
16H-VH-G.L.  (1)   EVQLVESGGGLVQPGGSLRLSCAASGFTFSSYWMSWVRQAPGKGLEWVAY
16H.VH       (1)   EVQLVESGGGLVQPGGSLRLSCAGSGFTFSSYWMSWVRQAPGKGLEWVAY

16H-VH-G.L. (51)   IKQDGNEKYYVDSVKGRFTISRDNAKNSLYLQMNSLRAEDTAVYYCAREG
16H.VH      (51)   IKQDGNEKYYVDSVKGRFTISRDNAKKSLYLQMNSLRAEDTAVYYCAREG

16H-VH-G.L.(101)   ILWFGDLPTFWGQGTLVTVSS
16H.VH     (101)   ILWFGDLPTFWGQGILVTVSS
```

Figure 7

| # of samples seq'ed* | Location in cDNA | Base Change | # of Homozygotes | # of Heterozygotes | Alternate allele frequency | AA change | Location in peptide sequence |
|---|---|---|---|---|---|---|---|
| 70 | 22 | G→C | 4 | 31 | 27.9% | L→V | 8 (sig pep) |
| 70 | 31 | G→T | 6 | 48 | 42.9% | L→M | 11 (sig pep) |
| 88 | 382 | G→A | 5 | 40 | 28.4% | V→I | 128 (IgV-like) |
| 1.5 | 661 | T→C | ? | ? | ? | L→F | 221 (IgC-like) |

* Number of individuals. The number of chromosomes is twice this amount.

Figure 8

| mAb | IC50 |
|---|---|
| 2H | 6.6 |
| 4H | 9.3 |
| 6H | 11.2 |
| 8H | 8.8 |
| 10H | 11.1 |
| 15H | 8.2 |
| 16H | 6.3 |
| 18H | 12.7 |
| 21H | 8.7 |
| 25H | 12.6 |
| 31H | 10.0 |
| 32H | 11.6 |
| ICOS | 9.5 |

| mAb | IC50 |
|---|---|
| 33H | 8.3 |
| 34H | 14.4 |
| 38H | 8.6 |
| 39H | 12.6 |
| 41H | 5.9 |
| 43H | 8.0 |
| 44H | 9.2 |
| 45H | 10.5 |
| 2K | 17.0 |
| 3K | 10.0 |
| 4K | 15.1 |
| 5K | 18.9 |
| ICOS | 9.5 |

No DNA control
huB7RP1SNP221
huB7RP1SNP128

| | EC50 in pM | | |
| --- | --- | --- | --- |
| | +/+ | V128I | L221F |
| 16H | 27 | 27 | 29 |
| 5D | 10 | 11 | 15 |

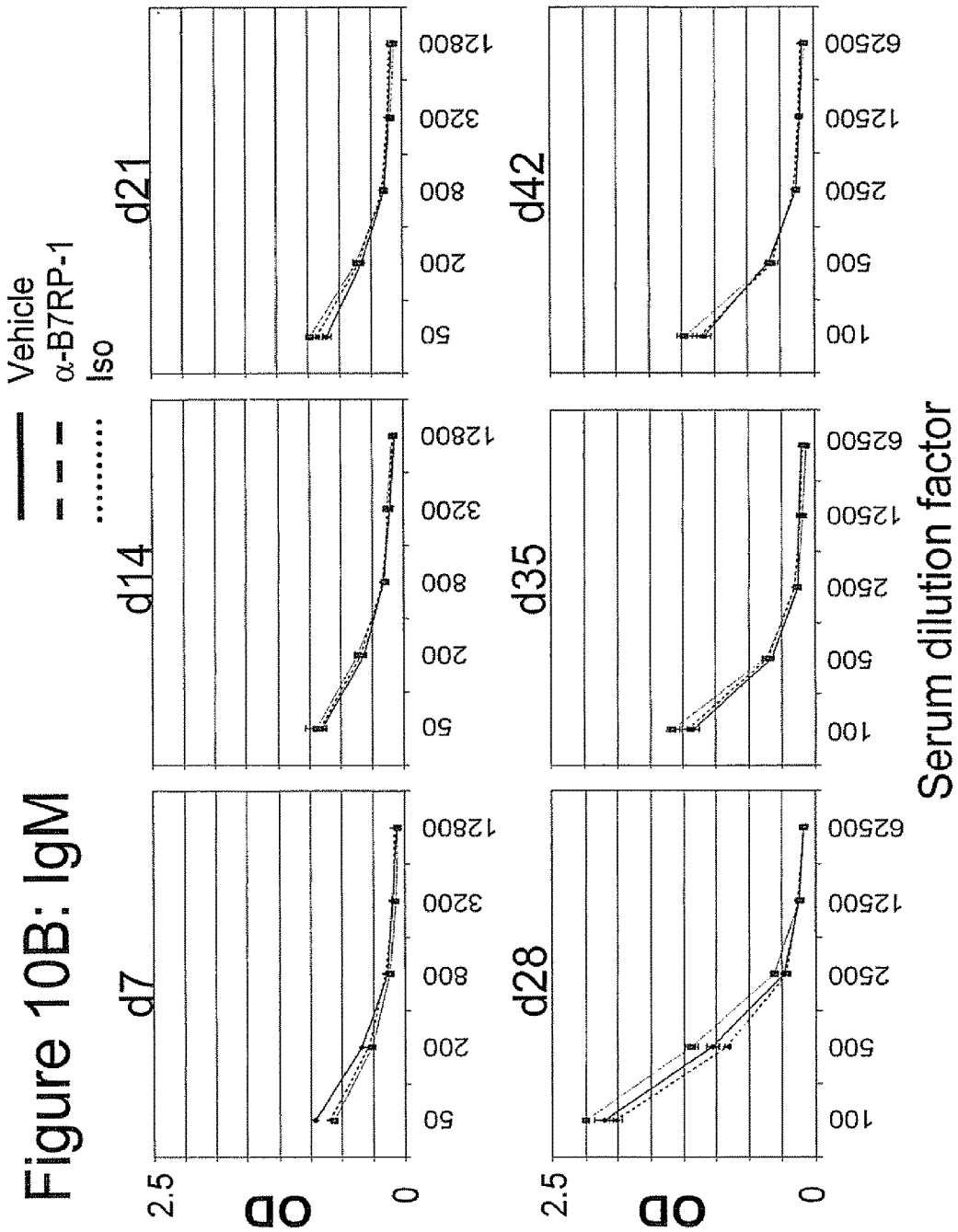
Figure 10B: IgM

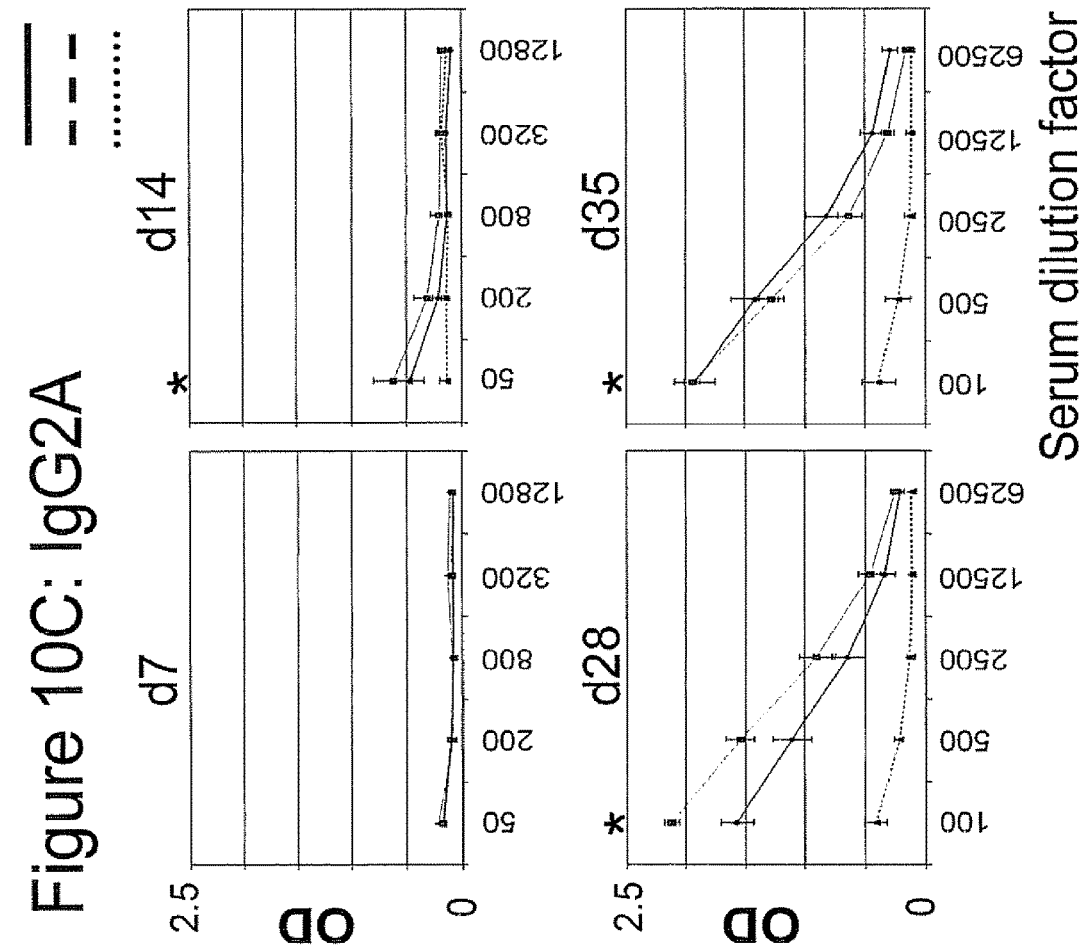
Figure 10C: IgG2A

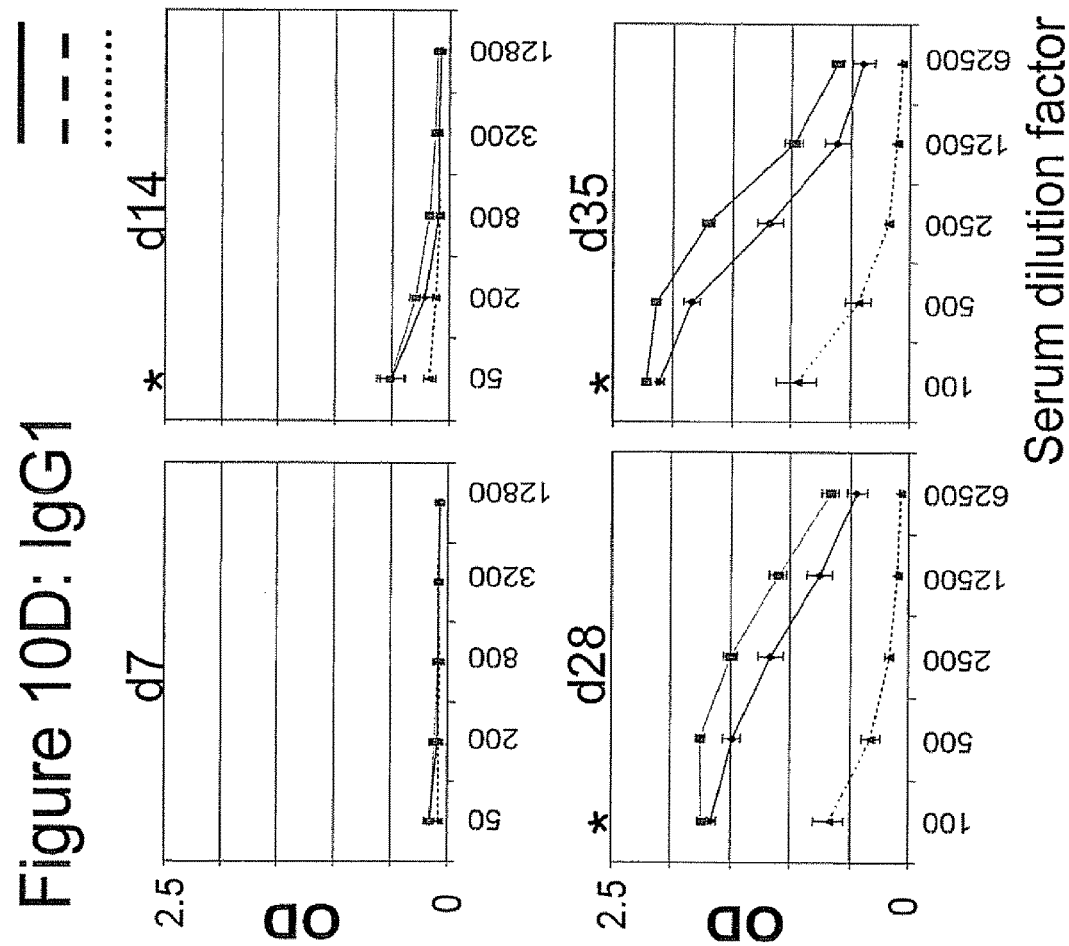

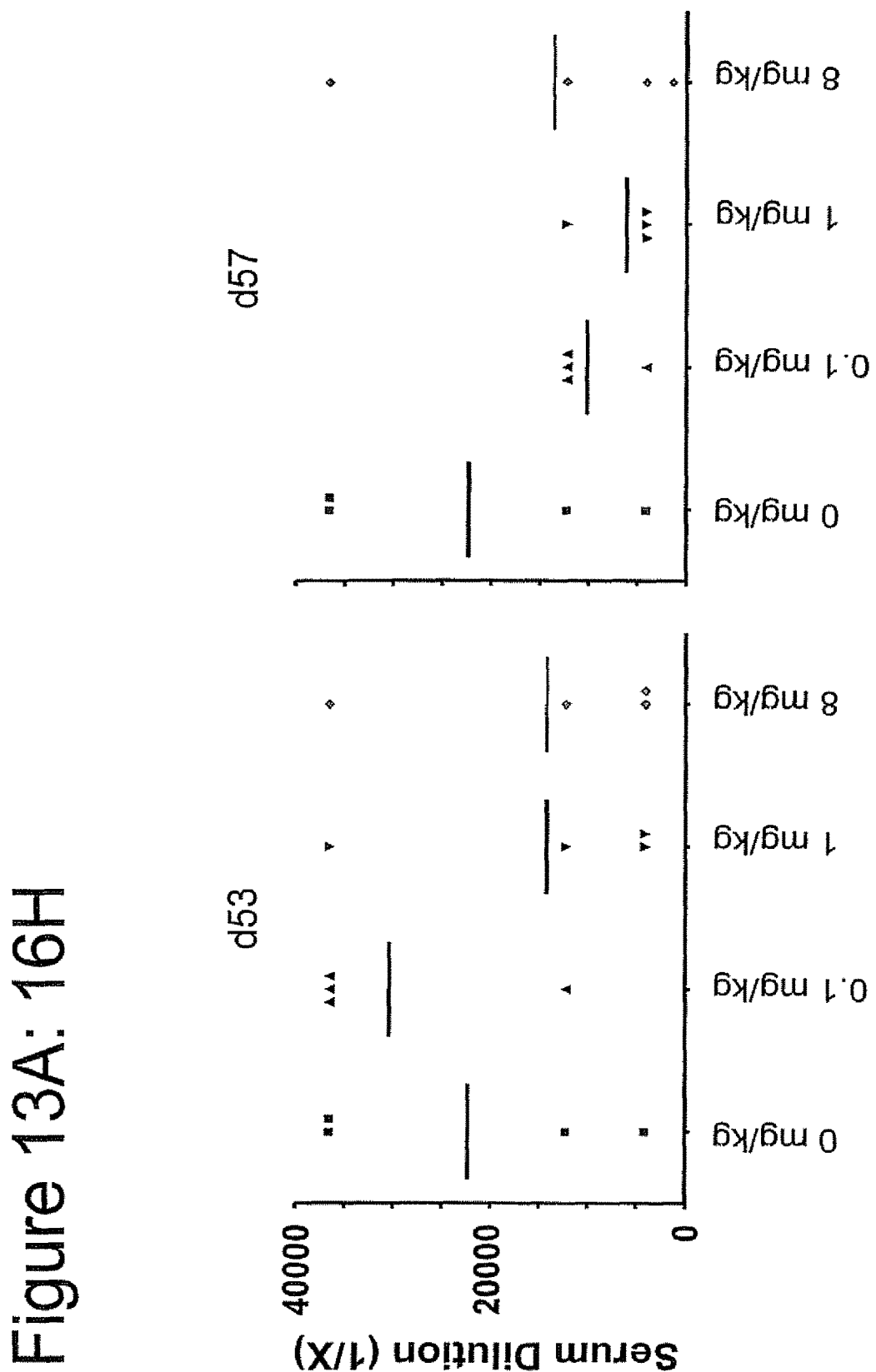
Figure 13A: 16H

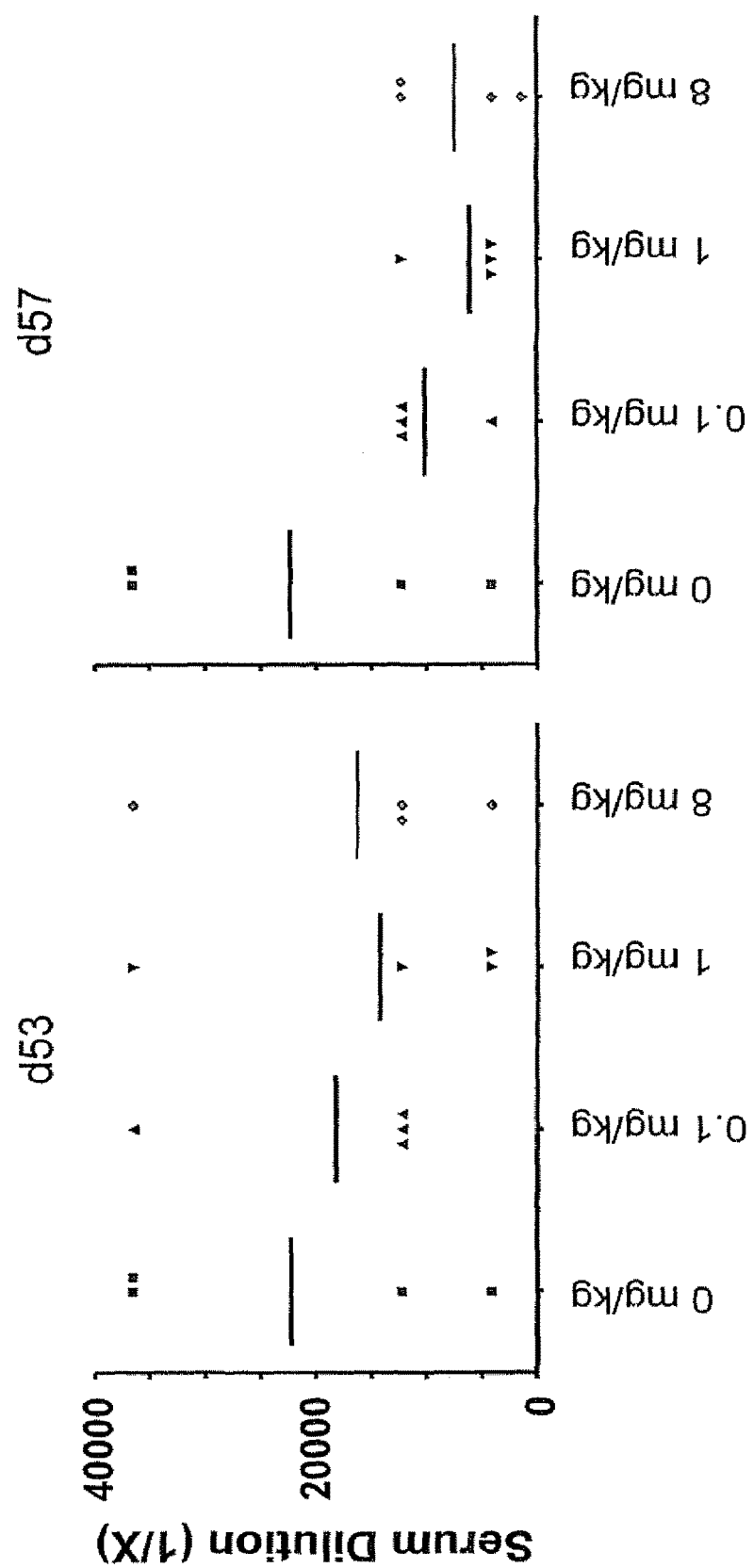
Figure 13B: 5D

HUMAN ANTI-B7RP1 NEUTRALIZING ANTIBODIES

This application claims priority to U.S. patent application Ser. No. 13/794,265, filed Mar. 11, 2013, which in turn claims priority to U.S. patent application Ser. No. 12/976,802, filed Dec. 22, 2010, which in turn claims priority to U.S. patent application Ser. No. 11/458,260, filed Jul. 18, 2006, which in turn claims priority to provisional U.S. Patent Application No. 60/700,265, filed Jul. 18, 2005.

FIELD OF THE INVENTION

The invention relates to human monoclonal antibodies that bind B7 related protein-1 (B7RP1). Compositions and methods for treating diseases and disorders related to immunosuppression and immune activation are also described.

BACKGROUND OF THE INVENTION

T-cells initiate the immune response, mediate antigen-specific effector functions, and regulate the activity of other leukocytes by secreting cytokines. For the generation of a proper T-lymphocyte (T-cell) immune response, two signals must be provided to the T-cell by antigen presenting cells (APC). Antigen must be presented to the T-cell receptor (TCR) via a major histocompatibility complex (MHC), in an event that determines specificity. T-cells can only recognize antigen presented on an APC. In addition to the antigen receptor, proper T-cell activation also requires the interaction of other cell-surface molecules on both the T-cell and the APC. These molecules, referred to as co-stimulatory molecules, consist of a receptor on the responding cell and a ligand present on the inducer cell. This antigen independent, co-stimulatory signal must be delivered by engagement of members of the B7 family on the APC with their receptors on T-cells. A productive immune response leads to proliferation, differentiation, clonal expansion, and effector function. In the absence of the second, co-stimulatory signal, T-cells undergo a state of long-lasting antigen-specific unresponsiveness, termed anergy. Phase II clinical experiments have demonstrated that blocking one co-stimulation pathway is efficacious in the treatment of psoriasis (Abrams et al, 2000, *J Exp Med* 192:681-94; Abrams et al., 1999, *J. Clin. Invest.* 103:1243-52) and rheumatoid arthritis (Kremer et al., 2003, *New England Journal of Medicine* 349:1907-15), indicating that this general strategy is a good target for immunomodulatory therapy.

A particular co-stimulatory B7 molecule, B7 related protein-1 (B7RP1), is a type 1 transmembrane protein with a signal sequence and extracellular domain at the amino-terminus, an extracellular domain comprising two Ig loops, a transmembrane domain, and a carboxy terminal intracellular domain (PCT Application Publication No. WO 00/46240). B7RP1 preferentially binds to ICOS (which stands for "inducible costimulator"; Yoshinga et al., 2000, *Int. Immun.* 12:1439-1447) expressed on the cell surface of T-cells. ICOS plays an important role in the production of both type 1 and type 2 cytokines by activated T-cells (Coyle et al., 2000, *Immunity* 13:95-105).

B7RP1 is the sole ligand expressed constitutively on APCs (Yoshinaga et al., 1999, *Nature.* 402:827-32), while ICOS is expressed only on activated T-cells (McAdam et al., 2000, *Journal of Immunology* 15:5035-40). B7RP1-dependent signaling is required for the activation of the effector (i.e. fully activated) T-cell, as well as its maturation from its nave precursor (Dong et al, 2003, *Journal of Autoimmunity.* 21:255-60; Coyle et al, 2000, *Immunity.* 11:95-105). Consequently, the B7RP1/ICOS interaction is required for proper T-cell-dependent recall immune responses (Dong et al., 2003, *Journal of Autoimmunity.* 21:255-60).

Current attempts to interfere with the co-stimulatory T-cell pathway have focused primarily on co-stimulatory polypeptides that block T-cell activation only, but have not focused on activation and maturation. Consequently, these therapies provide general inhibition of T-cell function. In contrast, blocking the B7RP1/ICOS interaction provides a more specific inhibition of T-cell function by affecting only mature effector T-cells. Thus, blocking the B7RP1/ICOS interaction in a clinical setting is highly desirable because it would provide a more limited side-effect profile than co-stimulation therapies that block naïve T-cell activation only.

SUMMARY OF THE INVENTION

The invention provides monoclonal antibodies that bind to B7 related protein-1 (B7RP1). In one embodiment, the monoclonal antibodies are human monoclonal antibodies that neutralize biological activities of B7RP1 and are particularly useful for inhibiting partially or completely the immune co-stimulatory activity of B7RP1. Also provided by the invention are cells, particularly hybridoma cells that produce the monoclonal antibodies of the invention. In particular aspects, the antibodies of the invention bind specifically to the H or D region of B7RP1 as described herein.

The invention further provides fusion proteins comprising the sequence of an antibody Fc region and one or more sequences identified as SEQ ID NO: 1 through SEQ ID NO. 40. Such molecules can be prepared using methods as described, for example, in International Patent Application, Publication No. WO 00/24782, which is hereby incorporated by reference. Such molecules can be expressed, for example, in mammalian cells (e.g. Chinese Hamster Ovary cells) or bacterial cells (e.g. *E. coli* cells).

In certain aspects, the invention provides antibodies comprising a heavy chain and a light chain, wherein the heavy chain comprises an heavy chain constant region selected from IgG1, IgG2, IgG3, IgG4, IgM, IgA and IgE heavy chain constant regions or any allelic variation thereof (as discussed in Kabat et at, 1991, SEQUENCES OF IMMUNOLOGICAL INTEREST, Fifth Edition, U.S. Department of Health and Human Services, NIH Publication No. 91-3242), incorporated herein by reference, and the variable region of the heavy chain comprises an amino acid sequence as set forth in any of SEQ ID NO: 7 through SEQ ID NO. 14, or an antigen-binding or an immunologically functional immunoglobulin fragment thereof. An antibody of the invention comprises either an amino acid sequence of the IgG2 heavy chain constant region as set forth in SEQ ID NO: 41 or an antigen-binding or an immunologically functional immunoglobulin fragment thereof, or an amino acid sequence of the IgG1 heavy chain constant region as set forth in SEQ ID NO: 42 or an antigen-binding or an immunologically functional immunoglobulin fragment thereof. In certain embodiments, the antibodies are monoclonal antibodies, human antibodies, or preferably human monoclonal antibodies.

In certain aspects, the invention provides antibodies comprising a heavy chain and a light chain, wherein the light chain comprises a constant region having an amino acid sequence as set forth in SEQ ID NO: 43 or an antigen-binding or an immunologically functional immunoglobulin fragment thereof, and the light chain variable region comprises an amino acid sequence as set forth in any of SEQ ID NO: 1 through SEQ ID NO. 6, or an antigen-binding or an immunologically functional immunoglobulin fragment thereof. In certain embodiments, the antibodies are monoclonal antibodies, human antibodies, or preferably human monoclonal antibodies.

In certain aspects, antibodies of the invention comprise a heavy chain and a light chain, wherein the variable region of the heavy chain comprises an amino acid sequence as set forth in SEQ ID NO: 7 or SEQ ID NO: 8, or an antigen-binding or an immunologically functional immunoglobulin fragment thereof. In other aspects, the light chain variable region comprises an amino acid sequence as set forth in SEQ ID NO: 1, or an antigen-binding or an immunologically functional immunoglobulin fragment thereof.

In other aspects, antibodies of the invention comprise a heavy chain and a light chain, wherein the variable region of the heavy chain comprises an amino acid sequence as set forth in SEQ ID NO: 9, or an antigen-binding or an immunologically functional immunoglobulin fragment thereof. In other aspects, the light chain variable region comprises an amino acid sequence as set forth in SEQ ID NO: 2, or an antigen-binding or an immunologically functional immunoglobulin fragment thereof.

In additional aspects, the heavy chain comprises at least one complementarity determining region (CDR) having an amino acid sequence as set forth in any of SEQ ID NO: 27 through SEQ ID NO. 40, or an antigen-binding or an immunologically functional immunoglobulin fragment thereof. In still further aspects, the light chain comprises at least one CDR having an amino acid sequence as set forth in any of SEQ ID NO: 15 through SEQ ID NO. 26, or an antigen-binding or an immunologically functional immunoglobulin fragment thereof.

The invention also provides antibodies that bind specifically to B7RP1, wherein the heavy chain comprises a variable region comprising an amino acid sequence as set forth in SEQ ID NO: 7 or SEQ ID NO: 8, or an antigen-binding or an immunologically functional immunoglobulin fragment thereof, and the light chain comprises a variable region comprising an amino acid sequence as set forth in SEQ ID NO: 1, or an antigen-binding or an immunologically functional immunoglobulin fragment thereof.

In addition, the invention provides antibodies that bind specifically to B7RP1, wherein the heavy chain comprises a variable region comprising an amino acid sequence as set forth in SEQ ID NO: 9, or an antigen-binding or an immunologically functional immunoglobulin fragment thereof, and the light chain comprises a variable region comprising an amino acid sequence as set forth in SEQ ID NO: 2, or an antigen-binding or an immunologically functional immunoglobulin fragment thereof.

In certain aspects, the invention also provides antibodies, comprising a heavy chain and a light chain, wherein the heavy chain comprises a heavy chain variable region, and wherein the heavy chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in any of SEQ ID NO: 7 through SEQ ID NO. 14, and wherein the light chain comprises a light chain variable region, and wherein the light chain variable region comprises a sequence that has at least about 80%, at least about 85%, at least about 900, 91%, 92%, 93%, 94%, 95%, 96%, 97%, 98%, or at least about 99% identity to the amino acid sequence as set forth in any of SEQ ID NO: 1 through SEQ ID NO. 6, wherein the antibody binds specifically to B7RP1.

The invention also provides antibodies that bind specifically to B7RP1, wherein the heavy chain comprises an amino acid sequence as set forth in SEQ ID NO: 44 or SEQ ID NO: 46, or an antigen-binding or an immunologically functional immunoglobulin fragment thereof, and the light chain comprises an amino acid sequence as set forth in SEQ ID NO: 45, or an antigen-binding or an immunologically functional immunoglobulin fragment thereof.

The invention also provides antibodies that bind specifically to B7RP1, wherein the heavy chain comprises an amino acid sequence as set forth in SEQ ID NO: 47, or an antigen-binding or an immunologically functional immunoglobulin fragment thereof, and the light chain comprises an amino acid sequence as set forth in SEQ ID NO: 48, or an antigen-binding or an immunologically functional immunoglobulin fragment thereof.

In certain aspects, the invention provides antibodies, comprising a heavy chain and a light chain, wherein the heavy chain comprises a heavy chain variable region, and wherein the heavy chain variable region comprises at least one CDR having a sequence that has at least about 75%, at least about 80%, at least about 85%, at least about 90%, 91%, 92%, 93%, 94%, 95%, 96%, 97%, 98/%, or at least about 99% identity to the amino acid sequence as set forth in any of SEQ ID NO: 27 through SEQ ID NO. 40, and wherein the light chain comprises a light chain variable region, and wherein the light chain variable region comprises at least one CDR having an amino acid sequence that has as least about 80%, at least about 85%, at least about 90%, 91%, 920%, 93%, 94%, 95%, 96%, 97%, 98%, or at least about 99% identity to the amino acid sequence as set forth in SEQ ID NO: 15 through SEQ ID NO. 26, wherein the antibody binds specifically to B7RP1.

The invention also provides single chain antibodies, single chain Fv antibodies, F(ab) antibodies, F(ab)' antibodies and (Fab')$_2$ antibodies.

In particular aspects, the invention provides a light chain comprising an amino acid sequence as set forth in SEQ ID NO: 15 through SEQ ID NO. 26, or an antigen-binding or an immunologically functional immunoglobulin fragment thereof.

In addition, the invention provides a heavy chain comprising an amino acid sequence as set forth in any of SEQ ID NO: 27 through SEQ ID NO. 40, or an antigen-binding or an immunologically functional immunoglobulin fragment thereof.

The invention also relates to isolated human antibodies that specifically bind B7RP1, wherein the antibody comprises: (a) human heavy chain framework regions, a human heavy chain CDR1 region, a human heavy chain CDR2 region, and a human heavy chain CDR3 region; and (b) human light chain framework regions, a human light chain CDR1 region, a human light chain CDR2 region, and a human light chain CDR3 region. In certain aspects, the human heavy chain CDR1 region can be the heavy chain CDR1 region as shown in any of SEQ ID NO: 27, 30, or 35 and the human light chain CDR1 region can be the light chain CDR1 region shown in any of SEQ ID NO: 15, 18, or 24. In other aspects, the human heavy chain CDR2 region can be the heavy chain CDR2 region as shown in any of SEQ ID NO: 28, 31, 33, 36, or 39, and the human light chain CDR2 region can be the light chain CDR2 as shown in any of SEQ ID NO: 16, 19, or 21. In still other aspects, the human heavy chain CDR3 region is the heavy chain CDR3 region as shown in any of SEQ ID NO: 29, 32, 34, 37, 38 or 40, and the human light chain CDR3 region is the light chain CDR3 region as shown in any of SEQ ID NO: 17, 20, 22, 23, 25, or 26.

The antibodies of the invention are characterized by the ability to bind specifically to B7RP1. Furthermore, antibodies of the invention have the capacity to antagonize at least one in vitro and/or in vivo activity associated with B7RP1 polypeptides. The invention provides isolated anti-human B7RP1 human antibodies with high affinity binding to B7RP1 polypeptides, wherein the antibodies bind to a human B7RP1 polypeptide and dissociates from the human B7RP1 polypeptide with a dissociation constant ($K_D$) of about $10^{-6}$ M, $10^{-7}$ M, $10^{-8}$ M, $10^{-9}$ M, $10^{-10}$ M, $10^{-11}$ M, $10^{-12}$ M, or less, as determined using KinExA, or which inhibit B7RP1 induced survival in an in vitro neutralization assay with an $EC_{50}$ of about $10^{-6}$ M, $10^{-7}$ M, $10^{-8}$ M, $10^{-9}$ M, $10^{-10}$ M, $10^{-11}$ M, $10^{-12}$ M, or less.

The invention also provides isolated human antibodies or an antigen-binding or immunologically functional immunoglobulin fragments thereof that bind specifically to B7RP1, wherein the antibodies or fragments comprise a heavy chain variable region comprising a heavy chain CDR1, CDR2, and CDR3, wherein:
 a) the heavy chain CDR1 has an amino acid sequence as set forth in SEQ ID NO: 27, the heavy chain CDR2 has an amino acid sequence as set forth in SEQ ID NO: 28, and the heavy chain CDR 3 has an amino acid sequence as set forth in SEQ ID NO: 29;
 b) the heavy chain CDR1 has an amino acid sequence as set forth in SEQ ID NO: 30, the heavy chain CDR2 has an amino acid sequence as set forth in SEQ ID NO: 31, and the heavy chain CDR 3 has an amino acid sequence as set forth in SEQ ID NO: 32;
 c) the heavy chain CDR1 has an amino acid sequence as set forth in SEQ ID NO: 27, the heavy chain CDR2 has an amino acid sequence as set forth in SEQ ID NO: 33, and the heavy chain CDR 3 has an amino acid sequence as set forth in SEQ ID NO: 34;
 d) the heavy chain CDR1 has an amino acid sequence as set forth in SEQ ID NO: 35, the heavy chain CDR2 has an amino acid sequence as set forth in SEQ ID NO: 36, and the heavy chain CDR 3 has an amino acid sequence as set forth in SEQ ID NO: 37;
 e) the heavy chain CDR1 has an amino acid sequence as set forth in SEQ ID NO: 27, the heavy chain CDR2 has an amino acid sequence as set forth in SEQ ID NO: 33, and the heavy chain CDR 3 has an amino acid sequence as set forth in SEQ ID NO: 38; or
 f) the heavy chain CDR1 has an amino acid sequence as set forth in SEQ ID NO: 35, the heavy chain CDR2 has an amino acid sequence as set forth in SEQ ID NO: 39, and the heavy chain CDR 3 has an amino acid sequence as set forth in SEQ ID NO: 40.

The invention also provides an isolated human antibody or an antigen-binding or an immunologically functional immunoglobulin fragment thereof that binds specifically to B7RP1, wherein the antibody or fragment comprises a light chain variable region comprising a light chain CDR1, CDR2, and CDR3, wherein:
 a) the light chain CDR1 has an amino acid sequence as set forth in SEQ ID NO: 15, the light chain CDR2 has an amino acid sequence as set forth in SEQ ID NO: 16, and the light chain CDR 3 has an amino acid sequence as set forth in SEQ ID NO: 17;
 b) the light chain CDR1 has an amino acid sequence as set forth in SEQ ID NO: 18, the light chain CDR2 has an amino acid sequence as set forth in SEQ ID NO: 19, and the light chain CDR 3 has an amino acid sequence as set forth in SEQ ID NO: 20;
 c) the light chain CDR1 has an amino acid sequence as set forth in SEQ ID NO: 15, the light chain CDR2 has an amino acid sequence as set forth in SEQ ID NO: 21, and the light chain CDR 3 has an amino acid sequence as set forth in SEQ ID NO: 22;
 d) the light chain CDR1 has an amino acid sequence as set forth in SEQ ID NO: 18, the light chain CDR2 has an amino acid sequence as set forth in SEQ ID NO: 19, and the light chain CDR 3 has an amino acid sequence as set forth in SEQ ID NO: 23;
 e) the light chain CDR1 has an amino acid sequence as set forth in SEQ ID NO: 24, the light chain CDR2 has an amino acid sequence as set forth in SEQ ID NO: 16, and the light chain CDR 3 has an amino acid sequence as set forth in SEQ ID NO: 25; or
 f) the light chain CDR1 has an amino acid sequence as set forth in SEQ ID NO: 24, the light chain CDR2 has an amino acid sequence as set forth in SEQ ID NO: 16, and the light chain CDR 3 has an amino acid sequence as set forth in SEQ ID NO: 26.

The invention also provides antibodies that compete with binding of the antibodies described herein to B7RP1. In certain aspects, a competitive antibody of the invention competes with binding of an antibody that comprises any of SEQ ID NO: 1-40 to human B7RP1.

Also part of the invention are polynucleotide sequences that encode anti-human B7RP1 human antibodies, vectors comprising the polynucleotide sequences encoding anti-human B7RP1 human antibodies, host cells transformed with vectors incorporating polynucleotides that encode anti-human B7RP1 human antibodies, formulations comprising anti-human B7RP1 human antibodies and methods of making and using same.

The invention also provides methods for detecting B7RP1 in a biological sample, comprising the step of contacting the sample with an antibody of the invention or antigen-binding fragment thereof. An anti-B7RP1 antibody of the invention may be employed in any known assay method, such as competitive binding assays, direct and indirect sandwich assays, immunoprecipitation assays and enzyme-linked immunosorbent assays (ELISA) (See, Sola, 1987, *Monoclonal Antibodies: A Manual of Techniques*, pp. 147-158, CRC Press, Inc.) for the detection and quantitation of B7RP1. The antibodies can bind B7RP1 with an affinity that is appropriate for the assay method being employed.

In addition, the invention provides methods for treating a disease associated with increased production of B7RP1, increased sensitivity to B7RP1, and/or diseases related to control of T-cell responses, comprising the step of administering a pharmaceutically effective amount of a pharmaceutical composition comprising at least one antibody of the invention or an antigen-binding or an immunologically functional immunoglobulin fragment thereof to an individual in need thereof.

Embodiments of the invention will become evident from the following detailed description and the claims.

BRIEF DESCRIPTION OF THE DRAWINGS

FIG. 7 depicts a summary of a B7RP-1 single nucleotide polymorphism (SNP) analysis.

FIG. 8 depicts a summary of the analysis of a set of anti-human B7RP-1 monoclonal antibodies in ELISA competition assays. Values shown are $IC_{50}$s for inhibition of binding of an ICOS-Fc fusion protein.

FIGS. 10B, 10C, and 10D show the results of antigen challenge experiments, analyzed for antigen-specific serum IgM (FIG. 10B), IgG2a (FIG. 10C), and IgG1 (FIG. 10D).

FIG. 13A depicts individual cynomolgus monkey and group mean titer values at day 53 and day 57 after secondary challenge with tetanus toxoid on day 42 in animals treated with 16H antibodies.

FIG. 13B depicts individual cynomolgus monkey and group mean titer values at day 53 and day 57 after secondary challenge with tetanus toxoid on day 42 in animals treated with 5D antibodies.

DETAILED DESCRIPTION OF CERTAIN EMBODIMENTS

Figures 1A, 1B:
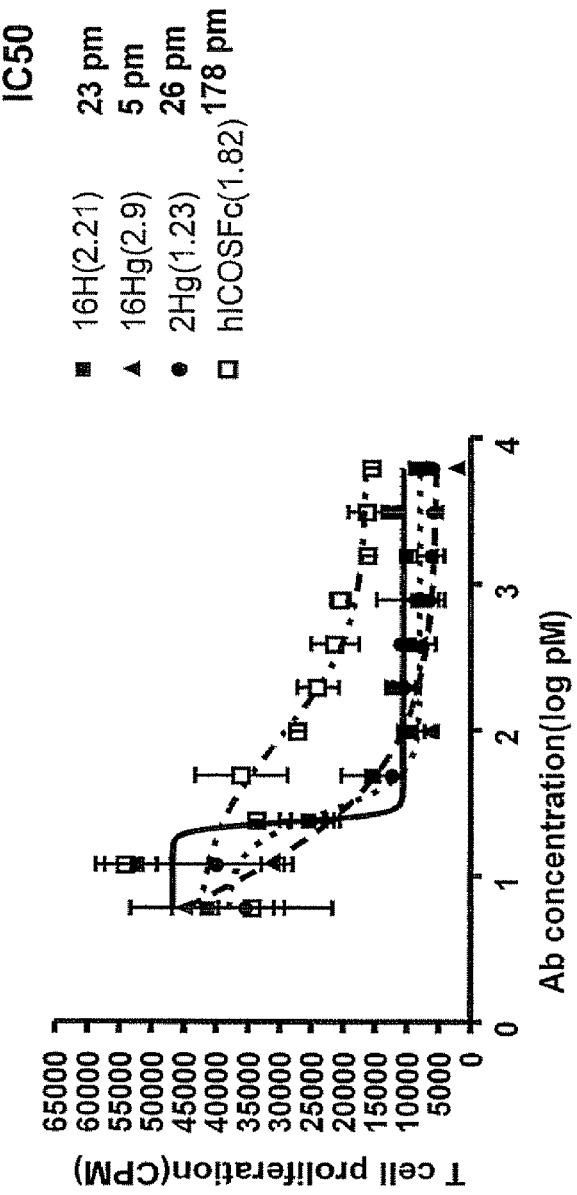
FIG. 1A depicts the 16H antibody variable region sequence (SEQ ID NO: 7) and the corresponding 16H variable region germline (16Hg) sequence (SEQ ID NO: 8).
FIG. 1B depicts results of co-stimulation assays using anti-CD3 and hB7RP1-Fc fusion protein demonstrating that 16Hg retains its biological activities compared with 16H.

The section headings used herein are for organizational purposes only and are not to be construed as limiting the subject matter described. All references cited in this application are expressly incorporated by reference herein for any purpose.

Definitions

Conventional techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Similarly, conventional techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings. The phrases "biological property", "biological characteristic", and the term "activity" in reference to an antibody of the present invention are used interchangeably herein and include, but are not limited to, epitope affinity and specificity (e.g., anti-human B7RP1 human antibody binding to human B7RP1), ability to antagonize the activity of the targeted polypeptide (e.g., B7RP1 activity), the in vivo stability of the antibody, and the immunogenic properties of the antibody. Other identifiable biological properties or characteristics of an antibody recognized in the art include, for example, cross-reactivity, (i.e., with non-human homologs of B7RP1, or with other proteins or tissues, generally), and ability to preserve high expression levels of protein in mammalian cells. The aforementioned properties or characteristics can be observed or measured using art-recognized techniques including, but not limited to ELISA, competitive ELISA, surface plasmon resonance analysis, in vitro and in vivo neutralization assays (e.g., Example 2), and immunohistochemistry with tissue sections from different sources including human, primate, or any other appropriate source. Particular activities and biological properties of anti-human B7RP1 human antibodies are described in further detail in the Examples below.

The term "isolated polynucleotide" as used herein shall mean a polynucleotide of genomic DNA, cDNA, RNA, or synthetic origin or some combination thereof, which by virtue of its origin the isolated polynucleotide (1) is not associated with all or a portion of a polynucleotide with which the isolated polynucleotide is found in nature, (2) is linked to a polynucleotide to which it is not linked in nature, or (3) does not occur in nature as part of a larger sequence.

The term "polynucleotide" as referred to herein means single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA or RNA.

The term "oligonucleotide" referred to herein includes naturally occurring, and modified nucleotides linked together by naturally occurring, and/or non-naturally occurring oligonucleotide linkages. Oligonucleotides are a polynucleotide subset comprising members that are generally single-stranded and have a length of 200 nucleotides or fewer. In certain embodiments, oligonucleotides are 10 to 60 nucleotides in length. In certain embodiments, oligonucleotides are 12, 13, 14, 15, 16, 17, 18, 19, or 20 to 40 nucleotides in length. Oligonucleotides may be single stranded or double stranded, e.g. for use in the construction of a genetic mutant. Oligonucleotides of the invention may be sense or antisense oligonucleotides with reference to a protein-coding sequence.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl Acids Res.*, 14:9081; Stec et al., 1984, *J. Am. Chem. Soc.*, 06:6077; Stein et al, 1988, *Nucl. Acids Res.*, 16:3209; Zon et al., 1991, *Anti-Cancer Drug Design*, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, *Chemical Reviews*, 90:543, the disclosures of which are hereby incorporated by reference for any purpose. An oligonucleotide can include a detectable label to enable detection of the oligonucleotide or hybridization thereof.

The term "isolated protein" referred to herein means that a subject protein (1) is free of at least some other proteins with which it would be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. In one embodiment, the isolated protein is substantially free from proteins or polypeptides or other contaminants that are found in its natural environment that would interfere with its use (therapeutic, diagnostic, prophylactic, research or otherwise).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous substances. In certain embodiments, the antibody is purified (1) to greater than 95% or greater than 99% by weight of antibody as determined by the Lowry method, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present.

The terms "polypeptide" or "protein" means molecules having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass anti-B7RP1 antibodies, or sequences that have deletions from, additions to, and/or substitutions of one or more amino acid of an anti-B7RP1 antibody.

The term "polypeptide fragment" refers to a polypeptide that has an amino-terminal deletion, a carboxyl-terminal deletion, and/or an internal deletion. In certain embodiments, fragments are at least 5 to about 500 amino acids long. It will be appreciated that in certain embodiments, fragments are at least 5, 6, 8, 10, 14, 20, 50, 70, 100, 110, 150, 200, 250, 300, 350, 400, or 450 amino acids long. Particularly useful polypeptide fragments include functional domains, including binding domains particularly antigen-binding domains, especially wherein the antigen is an epitope of human B7RP1. In the case of an anti-B7RP1 antibody, useful fragments include but are not limited to a CDR region, a variable domain of a heavy or light chain, a portion of an antibody chain or just its variable region including two CDRs, and the like.

The term "specific binding agent" refers to a naturally occurring or non-naturally occurring molecule that specifically binds to a target. Examples of specific binding agents include, but are not limited to, proteins, peptides, nucleic acids, carbohydrates, and lipids. In certain embodiments, a specific binding agent is an antibody.

The term "specific binding agent to B7RP1" refers to a specific binding agent that specifically binds any portion of B7RP1. In certain embodiments, a specific binding agent to B7RP1 is an antibody that binds specifically to B7RP1.

By way of example, an antibody "binds specifically" to a target if the antibody, when labeled, can be competed away from its target by the corresponding non-labeled antibody.

The term "immunologically functional immunoglobulin fragment" as used herein refers to a polypeptide fragment that contains at least the CDRs of the immunoglobulin heavy and light chains. An immunologically functional immunoglobulin fragment of the invention is capable of binding to an antigen. In certain embodiments, the antigen is a ligand that specifically binds to a receptor. In these embodiments, binding of an immunologically functional immunoglobulin fragment of the invention prevents binding of the ligand to its receptor, interrupting the biological response resulting from ligand binding to the receptor. In one embodiment, an immunologically functional immunoglobulin fragment of the invention binds specifically to B7RP1. Preferably, the fragment binds specifically to human B7RP1.

The term "naturally-occurring" or "native" as used herein and applied to an object refers to the fact that the object can be found in nature. For example, a polypeptide or polynucleotide sequence that is present in an organism (including viruses) that can be isolated from a source in nature and that has not been intentionally modified by man is naturally-occurring. The term "non-naturally occurring" or "non-native" as used herein refers to a material that is not found in nature or that has been structurally modified or synthesized by man. For example, "non-naturally occurring" can refer to a variant, such as a polynucleotide variant that can be produced using art-known mutagenesis techniques, or a polypeptide variant produced by such a polynucleotide variant. Such variants include, for example, those produced by nucleotide substitutions, deletions or additions that may involve one or more nucleotides. Polynucleotide variants can be altered in coding or non-coding regions or both. Alterations in the coding regions may produce conservative or non-conservative amino acid substitutions, deletions, or additions. Especially certain among these are silent substitutions, additions, deletions, and conservative substitutions, which do not alter the properties and activities of a B7RP1 antibody of the invention. One of skill in the art can readily determine how to generate such a variant using methods well known in the art.

The term "operably linked" means that the components to which the term is applied are in a relationship that allows them to carry out their inherent functions under suitable conditions. For example, a control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can effect expression, processing or intracellular localization of coding sequences to which they are operably linked. The nature of such control sequences may depend upon the host organism. In particular embodiments, control sequences for prokaryotes may include a promoter, ribosomal binding site, and transcription termination sequence. In other particular embodiments, control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "vector" includes a nucleic acid molecule capable of carrying into a cell another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors useful in the practice of recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The phrase "recombinant host cell" (or simply "host cell") includes a cell into which a recombinant expression vector has been introduced. It will be understood by those of skill in the art that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A wide variety of host expression systems can be used to express the antibodies of the present invention including bacterial, yeast, baculoviral and mammalian expression systems (as well as phage display expression systems). An example of a suitable bacterial expression vector is pUC19. To express an antibody recombinantly, a host cell is transfected with one or more recombinant expression vectors carrying DNA fragments encoding the immunoglobulin light and heavy chains of the antibody such that the light and heavy chains are expressed in the host cell and can be secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook et al., 2001, MOLECULAR CLONING, A LABORATORY MANUAL, Cold Spring Harbor Laboratories, Ausubel, F. M. et al. (eds.), CURRENT PROTOCOLS IN MOLECULAR BIOLOGY, Greene Publishing Associates, (1989) and in U.S. Pat. No. 4,816,397 to Boss et al.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52: 456; Sambrook et al., 2001, MOLECULAR CLONING, A LABORATORY MANUAL, Cold Spring Harbor Laboratories; Davis et al, 1986, BASIC METHODS IN MOLECULAR BIOLOGY, Elsevier; and Chu et al, 1981, *Gene* 13: 197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with DNA from the cell by physically integrating into a chromosome of the cell, or may be maintained transiently as an episomal element without being replicated, or may replicate independently as a plasmid. A cell is considered to have been stably transformed when the DNA is replicated with the division of the cell.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-Xaa-Ser or Asn-Xaa-Thr, wherein the amino acid residue designated as Xaa may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional antibody variants include cysteine variants wherein one or more cysteine residues are deleted from or substituted for another amino acid (e.g., serine) compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

In additional embodiments, antibody variants can include antibodies comprising a modified Fc fragment or a modified heavy chain constant region. An Fc fragment, which stands for "fragment that crystallizes," or a heavy chain constant region can be modified by mutation to confer on an antibody altered binding characteristics. See, for example, Burton and Woof, 1992, *Advances in Immunology* 51: 1-84; Ravetch and Bolland, 2001, *Annu. Rev Immunol.* 12: 275-90; Shields et al, 2001, *Journal of Biol. Chem* 226: 6591-6604; Telleman and Junghans, 2000, *Immunology* 100: 245-251; Medesan et al., 1998, *Eur. J. Immunol.* 28: 2092-2100; all of which are incorporated herein by reference). Such mutations can include substitutions, additions, deletions, or any combination thereof, and are typically produced by site-directed mutagenesis using one or more mutagenic oligonucleotide(s) according to methods described herein, as well as according to methods known in the art (see, for example, Sambrook et al., MOLECULAR CLONING: A LABORATORY MANUAL, 3rd Ed., 2001, Cold Spring Harbor, N.Y. and Berger and Kimmel, METHODS IN ENZYMOLOGY, Volume 152, *Guide to Molecular Cloning Techniques*, 1987, Academic Press, Inc., San Diego, Calif., which are incorporated herein by reference).

According to certain embodiments, amino acid substitutions may (1) reduce susceptibility to proteolysis, (2) reduce susceptibility to oxidation, (3) alter binding affinity, and/or (4) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In certain embodiments, a conservative amino acid substitution typically does not substantially change the structural characteristics of the parent sequence (e.g., a replacement amino acid should disrupt or tend to disrupt secondary structure that characterizes a parent sequence, such as a helix). Examples of art-recognized polypeptide secondary and tertiary structures are described in PROTEINS, STRUCTURES AND MOLECULAR PRINCIPLES, (Creighton, Ed.), 1984, W. H. Freeman and Company, New York; INTRODUCTION TO PROTEIN STRUCTURE (C. Branden and J. Tooze, eds.), 1991, Garland Publishing, New York, N.Y.; and Thornton et al., 1991, *Nature* 354:105, each of which are incorporated herein by reference.

"Antibody" or "antibody peptide(s)" refer to an intact antibody, or a binding fragment thereof that competes with the intact antibody for specific binding. In certain embodiments, binding fragments are produced by recombinant DNA techniques. In additional embodiments, binding fragments are produced by enzymatic or chemical cleavage of intact antibodies. Binding fragments include, but are not limited to, F(ab), F(ab'), F(ab')$_2$, Fv, and single-chain antibodies.

The invention provides antibodies that comprise a heavy chain and a light chain, wherein the heavy and light chains together form an antigen binding structure capable of specifically binding B7RP1. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxyl-terminus. The term "heavy chain", as used herein, encompasses a full-length heavy chain and fragments thereof. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof. A F(ab) fragment is comprised of one light chain and the $C_H1$ and variable regions of one heavy chain. The heavy chain of a F(ab) molecule cannot form a disulfide bond with another heavy chain molecule. A F(ab') fragment contains one light chain and one heavy chain that contains more of the constant region, between the $C_H1$ and $C_H2$ domains, such that an interchain disulfide bond can be formed between two heavy chains to form a F(ab')$_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203.

A bivalent antibody other than a "multispecific" or "multifunctional" antibody, in certain embodiments, is understood to comprise binding sites having identical antigenic specificity.

In assessing antibody binding and specificity according to the invention, an antibody substantially inhibits adhesion of a ligand to a receptor when an excess of antibody reduces the quantity of ligand bound to receptor by at least about 20%, 40%, 60%, 80%, 85%, or more (as measured, inter alia, using an in vitro competitive binding assay).

By "neutralizing antibody" is meant an antibody molecule that is able to block or substantially reduce an effector function of a target antigen to which it binds. Accordingly, a "neutralizing" anti-B7RP1 antibody is capable of blocking or substantially reducing an effector function, such as receptor binding and/or elicitation of a cellular response, of B7RP1. "Substantially reduce" is intended to mean at least about 60%, at least about 70%, at least about 75%, at least about 80%, at least about 85%, or at least about 90% reduction of an effector function of the target antigen (e.g., human B7RP1).

The term "epitope" includes any site on an antigen that is capable of specific binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In certain embodiments, an antibody is said to specifically bind an antigen when the equilibrium dissociation constant is about $10^{-6}$ M, $10^{-7}$ M, $10^{-8}$ M, $10^{-9}$ M, $10^{-10}$ M, $10^{-11}$ M, $10^{-12}$ M, or less than about $10^{-12}$ M.

An antibody binds "essentially the same epitope" as a reference antibody, when the two antibodies recognize identical or sterically overlapping epitopes. The most widely used and rapid methods for determining whether two antibodies bind to identical or sterically overlapping epitopes are competition assays, which can be configured in all number of different formats, using either labeled antigen or labeled antibody. Usually, the antigen is immobilized on a substrate, and the ability of unlabeled antibodies to block the binding of labeled antibodies is measured using radioactive isotopes or enzyme labels.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by labeled avidin (e.g., streptavidin comprising a detectable marker such as a fluorescent marker, a chemiluminescent marker or an enzymatic activity that can be detected by optical or colorimetric methods). In certain embodiments, the label can also be therapeutic. Various methods of labeling polypeptides and glycoproteins are known in the art and may be used advantageously in the methods disclosed herein. Examples of labels for polypeptides include, but are not limited to radioisotopes or radionuclides such as $^{3}H$, $^{14}C$, $^{15}N$, $^{35}S$, $^{90}Y$, $^{99m}Tc$, $^{111}In$, $^{125}I$, and $^{31}I$, fluorescent labels (e.g., fluorescein isothiocyanate or FITC, rhodamine, or lanthanide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, or epitope tags). In certain embodiments, labels are attached by spacer arms (such as $(CH_2)_n$, where n<about 20) of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent or drug" as used herein refers to a chemical compound or composition capable of inducing a desired therapeutic effect when properly administered to a patient. The expression "pharmaceutically effective amount" in reference to a pharmaceutical composition comprising one or a plurality of the antibodies of the invention is understood to mean, according to the invention, an amount of the said pharmaceutical composition that is capable of abolishing, in a patient, the decrease in the sensitivity threshold to external stimuli with a return of this sensitivity threshold to a level comparable to that observed in healthy subjects.

A "disorder" is any condition that would benefit from treatment according to the present invention. "Disorder" and "condition" are used interchangeably herein and include chronic and acute immune system disorders or immune system diseases associated with inappropriate immune response, including those pathological conditions which predispose the mammal to the disorder in question. A number of conditions and disorders that would benefit from the treatment according to the present invention are described, for example, in International Patent Application No. PCT/US00/01871 (Publication No. WO 00/46240), the disclosure of which is incorporated by reference in its entirety.

The terms "immune system disease" and "immune system condition" encompass any medical condition or disorder associated with increased levels of B7RP1, increased sensitivity to B7RP1, or T-cell mediated diseases, including, but not limited to, autoimmune disease, graft survival, bone marrow and organ transplantation, allosensitization due to blood transfusions, toxic shock syndrome, T-cell dependent B-cell mediated diseases, chronic inflammatory diseases associated with chronic immune cell dysfunction, lymphoproliferative disorders (such as multiple myeloma, Waldenstom's macroglobulinemia, and crioglobulinemias), and cancer. Non-limiting examples of autoimmune diseases include systemic lupus erythematosis, rheumatoid arthritis, immune thrombocytopenic purpura (ITP), multiple sclerosis, diabetes, and psoriasis. Non-limiting examples of chronic inflammatory diseases include inflammatory bowel disease (such as Crohn's disease and ulcerative colitis), Grave's disease, Hashimoto's thyroiditis, and diabetes mellitus.

The terms "immune system disease" and "immune system condition" also encompass any clinical condition that would be ameliorated by the inhibition of antibody production, such as hypersensitivity reactions. Hypersensitivity reactions can be caused, for example, by hay fever, allergies, asthma, atopy, and acute edema. Non-limiting examples of diseases that cause antibody-mediated hypersensitivity reactions include systemic lupus erythematosis, arthritis (such as rheumatoid arthritis, reactive arthritis, psoriatic arthritis), nephropathies (such as glomerulo-nephritis, membranous, mesangiocapillary, focal segmental, focal necrotizing, crescentic, and proliferative nephropathies such as tubulopathies), skin disorders (such as pemphigus and pemphigoid, erythema nodosum), endocrinopathies (such as thyroiditis, Grave's disease, Hashimoto's disease, insulin dependent diabetes mellitus), various pneumopathies (such as extrinsic alveolitis), various vasculopathies, coeliac disease, diseases with aberrant production of IgA, many anemias and thrombocytopenias, Guillain-Barre Syndrome, and myasthenia gravis.

As used herein, the terms "effective amount" and "therapeutically effective amount" when used with reference to a vehicle- or a pharmaceutical composition comprising one or more anti-human B7RP1 human antibodies refers to an amount or dosage sufficient to produce a desired result (i.e., where for therapy with the vehicle- or anti-human B7RP1 human antibodies of the present invention the desired result is the desired modulation of T-cell responses, for example) or to support an observable decrease in the level of one or more biological activities of B7RP1. More specifically, a therapeutically effective amount is an amount of the anti-human B7RP1 human antibody(ies) sufficient to inhibit, for some period of time, one or more of the clinically defined pathological processes associated with the condition at issue, e.g. immune disorders and diseases, in a subject treated in vivo with the agent. In the present invention, an "effective amount" of an anti-B7RP1 antibody may modulate T-cell responses in a patient. In the methods of the present invention, the term "control" and grammatical variants thereof, are used to refer to the prevention, partial or complete inhibition, reduction, delay or slowing down of an unwanted event, e.g. immune response. The effective amount may vary depending on the specific vehicle- or anti-human B7RP1 human antibody(ies) selected, and is also dependent on a variety of factors and conditions related to the subject to be treated and the severity of the disorder.

For example, if the vehicle- or anti-human B7RP1 human antibody(ies) is to be administered in vivo, factors such as the age, weight and health of the patient as well as dose response curves and toxicity data obtained in preclinical animal work would be among those considered. If the agent is to be contacted with the cells in vitro, one would also design a variety of pre-clinical in vitro studies to assess such parameters as uptake, half-life, dose, toxicity, etc. The determination of an effective amount or a therapeutically effective amount for a given agent is well within the ability of those skilled in the art.

As used herein, the terms "B7 related protein-1" and "B7RP1" are defined as all mammalian species of native sequence B7RP1, which is described in International Patent Application Publication No. WO 00/46240, which is incorporated herein by reference.

As used herein, "substantially pure" or "substantially purified" means a compound or species that is the predominant species present (i.e., on a molar basis it is more abundant than any other individual species in the composition). In certain embodiments, a substantially purified fraction is a composition wherein the species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the species is purified to essential homogeneity (contaminant species cannot be detected in the composition by conventional detection methods) wherein the composition consists essentially of a single macromolecular species.

The term "patient" includes human and animal subjects.

"Treatment" or "treat" refers to both therapeutic treatment and prophylactic or preventative measures. Those in need of treatment include those already with the disorder as well as those prone to have the disorder or those in which the disorder is to be prevented.

Unless otherwise required by context, singular terms shall include pluralities and plural terms shall include the singular.

According to certain embodiments of the invention, antibodies directed to B7RP1 may be used to treat immune system disorders and immune system diseases, including but not limited to, those mentioned above.

In one aspect of the invention are provided fully human monoclonal antibodies raised against and having biological and immunological specificity for binding to human B7RP1. In another aspect the invention provides nucleic acids comprising nucleotide sequences encoding amino acid sequences for heavy and light chain immunoglobulin molecules, particularly sequences corresponding to the variable regions thereof. Particular embodiments of this aspect of the invention are sequences corresponding to complementarity determining regions (CDRs), specifically from CDR1 through CDR3, of the heavy and light chains provided by the invention. In yet another aspect the invention provides hybridoma cells and cell lines that express the immunoglobulin molecules and antibodies, such as monoclonal antibodies of the invention. The invention also provides biologically and immunologically purified preparations of antibodies, such as monoclonal antibodies raised against and having biological and immunological specificity for binding to human B7RP1.

The ability to clone and reconstruct megabase-sized human loci in yeast artificial chromosomes (YACs) and to introduce them into the mouse germline provides an advantageous approach to elucidating the functional components of very large or crudely mapped loci as well as generating useful models of human disease. Furthermore, the utilization of such technology for substitution of mouse loci with their human equivalents provides unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study mechanisms underlying programmed expression and assembly of antibodies as well as their role in B-cell development. Furthermore, such a strategy provides a source for production of fully human monoclonal antibodies (MAbs).

The term "human antibody" includes antibodies having variable and constant regions substantially corresponding to human germline immunoglobulin sequences. In certain embodiments, human antibodies are produced in non-human mammals, including, but not limited to, rodents, such as mice and rats, and lagomorphs, such as rabbits. In certain embodiments, human antibodies are produced in hybridoma cells. In certain embodiments, human antibodies are produced recombinantly.

The term "recombinant" in reference to an antibody includes antibodies that are prepared, expressed, created or isolated by recombinant means. Representative examples include antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, et al., 1992, *Nucl. Acids Res.* 20:6287-6295); or antibodies prepared, expressed, created or isolated by any means that involves splicing of human immunoglobulin gene sequences to other DNA sequences. Such recombinant human antibodies have variable and constant regions derived from human germline immunoglobulin sequences.

Human antibodies have at least three advantages over non-human and chimeric antibodies for use in human therapy:

1) because the effector portion of the antibody is human, it may interact better with the other parts of the human immune system (e.g., destroy the target cells more efficiently by complement-dependent cytotoxicity (CDC) or antibody-dependent cellular cytotoxicity (ADCC));

2) the human immune system should not recognize the human antibody as foreign, and, therefore the antibody response against such an injected antibody should be less than against a totally foreign non-human antibody or a partially foreign chimeric antibody;

3) injected non-human antibodies have been reported to have a half-life in the human circulation much shorter than the half-life of human antibodies. Injected human antibodies will have a half-life essentially identical to naturally occurring human antibodies, allowing smaller and less frequent doses to be given.

Thus, fully human antibodies are expected to minimize the immunogenic and allergic responses intrinsic to mouse or mouse-derivatized MAbs, and to thereby increase the efficacy and safety of the administered antibodies. Fully human antibodies of the invention, therefore, can be used in the treatment of diseases and disorders associated with inappropriate immune response, the treatment thereof requiring repeated antibody administration. Thus, one particular advantage of the anti-B7RP1 antibodies of the invention is that the antibodies are fully human and can be administered to patients in a non-acute manner while minimizing adverse reactions commonly associated with human anti-mouse antibodies or other previously described non-fully human antibodies from non-human species.

One skilled in the art can engineer mouse strains deficient in mouse antibody production with large fragments of the human Ig loci so that such mice produce human antibodies in the absence of mouse antibodies. Large human Ig fragments may preserve the large variable gene diversity as well as the proper regulation of antibody production and expression. By exploiting the mouse cellular machinery for antibody diversification and selection and the lack of immunological tolerance to human proteins, the reproduced human antibody repertoire in these mouse strains yields high affinity antibodies against any antigen of interest, including human antigens. Using the hybridoma technology, antigen-specific human MAbs with the desired specificity may be produced and selected.

Transgenic animals (e.g., mice) can also be used to produce human antibodies in the absence of endogenous immunoglobulin production. For example, transfer of the human germ-line immunoglobulin gene array in such germ-line mutant mice will result in the production of human antibodies upon antigen challenge (see, e.g., Jakobovits et al., 1993, *Proc Natl Acad Sci. USA* 29:2551-2555; Jakobovits et al, 1993, *Nature* 2:255-258; Bruggemann et al., 1993, *Year in Immun.* 2:33, 1994, *Nature* 148:1547-1553) and, 1996, *Nature Biotechnology* 14:826; Gross et al., 2000, *Nature* 404:995-999; and U.S. Pat. Nos. 5,877,397, 5,874,299, 5,814,318, 5,789,650, 5,770,429, 5,661,016, 5,633,425, 5,625,126, 5,569,825, and 5,545,806, (each of which is incorporated herein by reference in its entirety for all purposes)). Human antibodies can also be produced in phage display libraries (Hoogenboom and Winter, 1992, *J. Mol. Biol* 227:381; Marks et al., 1991, *J. Mol. Biol.* 22:581). The techniques of Cole et al. and Boerner et at are also available for the preparation of human monoclonal antibodies (Cole et al., 1985, Monoclonal Antibodies and Cancer Therapy Alan R. Liss, p. 77; and Boerner et al., 1991, *J. Immunol.* 142:86-95).

Recombinant human antibodies may also be subjected to in vitro mutagenesis (or, when an animal transgenic for human Ig sequences is used, in vivo somatic mutagenesis) and, thus, the amino acid sequences of the $V_H$ and $V_L$ regions of the recombinant antibodies are sequences that, while derived from those related to human germline $V_H$ and $V_1$ sequences, may not naturally exist within the human antibody germline repertoire in vivo.

In certain embodiments, the skilled artisan can use constant regions from species other than human along with the human variable region(s) in such mice to produce chimeric antibodies.

A bispecific or bifunctional antibody typically is an artificial hybrid antibody having two different heavy chain/light chain pairs and two different binding sites. Bispecific antibodies may be produced by a variety of methods including, but not limited to, fusion of hybridomas or linking of F(ab') fragments. See, e.g., Songsivilai & Lachmann, 1990, *Clin. Exp Immunol.* 22: 315-321; Kostelny et al., 1992, *J. Immunol.* 148: 1547-1553.

The invention provides antibodies that bind to human B7RP1. These antibodies can be produced by immunization with full-length B7RP1 or fragments thereof. The antibodies of the invention can be polyclonal or monoclonal, and/or may be recombinant antibodies. In preferred embodiments, antibodies of the invention are human antibodies prepared, for example, by immunization of transgenic animals capable of producing human antibodies (see, for example, International Patent Application, Publication WO 93/12227).

The complementarity determining regions (CDRs) of the light chain and heavy chain variable regions of anti-B7RP1 antibodies of the invention can be grafted to framework regions (FRs) from the same, or another, species. In certain embodiments, the CDRs of the light chain and heavy chain variable regions of anti-B7RP1 antibody may be grafted to consensus human FRs. To create consensus human FRs, FRs from several human heavy chain or light chain amino acid sequences are aligned to identify a consensus amino acid sequence. The FRs of the anti-B7RP1 antibody heavy chain or light chain can be replaced with the FRs from a different heavy chain or light chain. Rare amino acids in the FRs of the heavy and light chains of anti-B7RP1 antibody typically are not replaced, while the rest of the FR amino acids can be replaced. Rare amino acids are specific amino acids that are in positions in which they are not usually found in FRs. The grafted variable regions from anti-B7RP1 antibodies of the invention can be used with a constant region that is different from the constant region of anti-B7RP1 antibody. Alternatively, the grafted variable regions are part of a single chain Fv antibody. CDR grafting is described, e.g., in U.S. Pat. Nos. 6,180,370, 5,693,762, 5,693,761, 5,585,089, and 5,530,101, which are hereby incorporated by reference for any purpose.

Antibodies of the invention can be prepared using transgenic mice that have a substantial portion of the human antibody producing locus inserted in antibody-producing cells of the mice, and that are further engineered to be deficient in producing endogenous, murine, antibodies. Such mice are capable of producing human immunoglobulin molecules and antibodies and do not produce or produce substantially reduced amounts of murine immunoglobulin molecules and antibodies. Technologies utilized for achieving this result are disclosed in the patents, applications, and references disclosed in the specification herein. In certain embodiments, the skilled worker may employ methods as disclosed in International Patent Application Publication No. WO 98/24893, which is hereby incorporated by reference for any purpose. See also Mendez et al., 1997, *Nature Genetics* 1:146-156, which is hereby incorporated by reference for any purpose.

The monoclonal antibodies (mAbs) of the invention can be produced by a variety of techniques, including conventional monoclonal antibody methodology, e.g., the standard somatic cell hybridization technique of Kohler and Milstein (1975, *Nature* 25:495). Other techniques for producing monoclonal antibodies may be employed, e.g., viral or oncogenic transformation of B-lymphocytes.

An exemplary animal system for preparing hybridomas is the mouse. Hybridoma production in the mouse is known in the art and immunization protocols and techniques for isolation of immunized splenocytes for fusion are also known in the art. Fusion partners (e.g., murine myeloma cells) and fusion procedures are also known.

In a certain embodiment, human monoclonal antibodies directed against B7RP1 can be generated using transgenic mice carrying parts of the human immune system rather than the mouse system. These transgenic mice, referred to herein as "HuMab" mice, contain a human immunoglobulin gene minilocus that encodes unrearranged human heavy (μ and γ) and κ light chain immunoglobulin sequences, together with targeted mutations that inactivate the endogenous μ and κ chain loci (Lonberg et al, 1994, *Nature* 368:856-859). Accordingly, the mice exhibit reduced expression of mouse IgM or κ and in response to immunization, the introduced human heavy chain and light chain transgenes undergo class switching and somatic mutation to generate high affinity human IgG κ monoclonal antibodies (Lonberg et al., supra; Lonberg and Huszar, 1995, *Intern. Rev. Immunol.* 11:65-93; Harding and Lonberg, 1995, *Ann. N.Y. Acad. Sci.* 764:536-546). The preparation of HuMab mice is described in detail in Taylor et al., 1992, *Nucleic Acids Res.* 20:6287-6295; Chen et al, 1993, *International Immunology* 5:647-656; Tuaillon et al., 1994, *J. Immunol.* 12:2912-2920; Lonberg et al, 1994, *Nature* 368:856-859; Lonberg, 1994, *Handbook of Exp. Pharmacology* 113:49-101; Taylor et al., 1994, *International Immunology* 6:579-591; Lonberg & Huszar, 1995, *Intern Rev Immunol.* 11:65-93; Harding & Lonberg, 1995, *Ann. N.Y. Acad. Sci* 24:536-546; Fishwild et al., 1996, *Nature Biotechnology* 14:845-851, the contents of all of which are hereby incorporated by reference in their entirety. See further U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, as well as U.S. Pat. No. 5,545,807 to Surani et al.; International Patent Application Publication Nos. WO 93/1227, published Jun. 24, 1993; WO 92/22646, published Dec. 23, 1992; and WO 92/03918, published Mar. 19, 1992, the disclosures of all of which are hereby incorporated by reference in their entirety. Alternatively, transgenic mice strains described in the Examples below can be used to generate human anti-B7RP1 antibodies.

The present invention provides human monoclonal antibodies that are specific for and neutralize bioactive human B7RP1 polypeptides. Also provided are antibody heavy and light chain amino acid sequences which are highly specific for and neutralize B7RP1 polypeptides when they are bound to them. This high specificity enables the anti-human B7RP1 human antibodies, and human monoclonal antibodies with like specificity, to be effective immunotherapy for B7RP1 associated diseases.

In one aspect, the invention provides isolated human antibodies that bind the same or essentially the same epitope as the 16H antibody provided herein.

In one aspect, the invention provides isolated human antibodies comprising at least one of the amino acid sequences shown in SEQ ID NOS: 1-40 or 44-58 that binds a B7RP1 polypeptide epitope with high affinity and has the capacity to antagonize B7RP1 polypeptide activity. These antibodies may bind the same or essentially the same epitope as the anti-B7RP1 antibodies shown in the Examples herein.

In certain embodiments, the isolated antibodies bind to B7RP1 polypeptide with a dissociation constant (K) of about $10^{-6}$ M, $10^{-7}$ M, $10^{-8}$ M, $10^{-9}$ M, $10^{-10}$ M, $10^{-11}$ M or less and inhibits B7RP1 induced survival in an in vitro neutralization assay with an $EC_{50}$ of about $10^{-6}$ M, $10^{-7}$ M, $10^{-8}$ M, $10^{-9}$ M or less. Examples of anti-human B7RP1 human antibodies that meet the aforementioned binding and neutralization criteria are provided herein.

In certain embodiments, anti-human B7RP1 human antibodies of the invention are referred to herein as 16H, 16Hg (germline), 5D, 2H, 2Hg (germline), 15H, 41H, and 43H. Antibody 16H comprises $V_L$ and $V_H$ polypeptide sequences as shown in SEQ ID NO: 7 and SEQ ID NO: 1, respectively. Antibody 16Hg comprises a variable light chain ($V_L$) and variable heavy chain ($V_H$) polypeptide sequences as shown in SEQ ID NO: 1 and SEQ ID NO: 8, respectively. Antibody 5D comprises $V_L$ and $V_H$ polypeptide sequences as shown in SEQ ID NO: 2 and SEQ ID NO: 9, respectively. Antibody 2H comprises $V_L$ and $V_H$ polypeptide sequences as shown in SEQ ID NO: 3 and SEQ ID NO: 10, respectively. Antibody 2Hg comprises $V_L$ and $V_H$ polypeptide sequences as shown in SEQ ID NO: 3 and SEQ ID NO: 11, respectively. Antibody 15H comprises $V_L$ and $V_H$ polypeptide sequences as shown in SEQ ID NO: 4 and SEQ ID NO: 12, respectively. Antibody 41H comprises $V_L$ and $V_H$ polypeptide sequences as shown in SEQ ID NO: 5 and SEQ ID NO: 13, respectively. Antibody 43H comprises $V_L$ and $V_H$ polypeptide sequences as shown in SEQ ID NO: 6 and SEQ ID NO: 14, respectively. The properties of the anti-human B7RP1 human antibodies of the present invention are specifically disclosed in the Examples. Particularly notable is the high affinity for B7RP1 polypeptide and high capacity to antagonize B7RP1 polypeptide activity demonstrated herein.

The dissociation constant ($K_D$) of an anti-human B7RP1 human antibody can be determined by surface plasmon resonance as generally described in the Examples below. Generally, surface plasmon resonance analysis measures real-time binding interactions between ligand (recombinant B7RP1 polypeptide immobilized on a biosensor matrix) and analyte (antibodies in solution) by surface plasmon resonance (SPR) using the BIAcore® system (Pharmacia Biosensor, Piscataway, N.J.). Surface plasmon analysis can also be performed by immobilizing the analyte (antibodies on a biosensor matrix) and presenting the ligand (recombinant V in solution). The dissociation constant ($K_D$) of an anti-human B7RP1 human antibody can also be determined by using KinExA methodology. In certain embodiments of the invention, the antibodies bind to B7RP1 with a $K_D$ of approximately $10^{-5}$ M, $10^{-6}$ M, $10^{-7}$ M, $10^{-8}$ M, $10^{-9}$ M, $10^{-10}$ M, $10^{-11}$ M, or $10^{-12}$ M. The term "$K_D$", as used herein, is intended to refer to the dissociation constant of a particular antibody-antigen interaction. For purposes of the present invention $K_D$ was determined as shown in the Examples below.

In certain embodiments, the antibodies of the invention are of the IgG1, IgG2, IgG3, or IgG4 isotype. The antibodies may be of the IgG2 or IgG1 isotype. In other embodiments, the antibodies of the invention may be of the IgM, IgA, IgE, or IgD isotype. In certain embodiments of the invention, the antibodies comprise a human kappa light chain and a human IgG1, IgG2, IgG3, or IgG4 heavy chain. Expression of antibodies of the invention comprising an IgG1 or an IgG2 heavy chain constant region is described in the Examples below. In particular embodiments, the variable regions of the antibodies are ligated to a constant region other than the constant region for the IgG1, IgG2, IgG3, or IgG4 isotype. In certain embodiments, the antibodies of the invention have been cloned for expression in mammalian cells.

In certain embodiments, conservative modifications to the heavy chains and light chains of anti-B7RP1 antibodies (and corresponding modifications to the encoding nucleotides) will produce anti-B7RP1 antibodies having functional and chemical characteristics similar to those of the anti-B7RP1 antibodies disclosed herein. In contrast, substantial modifications in the functional and/or chemical characteristics of anti-B7RP1 antibodies may be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis."

Amino acid substitutions (whether conservative or non-conservative) can be determined by those skilled in the art at the time such substitutions are desired. In certain embodiments, amino acid substitutions can be used to identify those amino acid residues of an anti-B7RP1 antibody that are involved in binding specificity and/or affinity of the antibody for B7RP1 (e.g. residues that are involved in binding of the antibody to a particular epitope), such as amino acid residues in CDR1, CDR2, and/or CDR3 regions of the light or heavy chains as described herein. Such amino acid substitutions may increase or decrease the affinity of the anti-B7RP1 antibodies described herein.

Minor changes in an amino acid sequence such as deletion, addition or substitution of one, a few or even several amino acids may lead to an allelic form of the original protein which has substantially identical properties. Therefore, in addition to the antibodies specifically described herein, other "substantially homologous" antibodies can be readily designed and manufactured utilizing various recombinant DNA techniques well known to those skilled in the art. In general, modifications of the genes may be readily accomplished by a variety of well-known techniques, such as site-directed mutagenesis. Therefore, the present invention contemplates "variant" or "mutant" anti-B7RP1 human antibodies having substantially similar characteristics to the anti-B7RP1 human antibodies disclosed herein (See, for example, WO 00/56772, all of which is hereby incorporated herein by reference). Thus, by the term "variant" or "mutant" in reference to an anti-B7RP1 human antibody is meant any binding molecule (molecule X) (i) in which the hypervariable regions CDR1, CDR2, and CDR3 of the heavy chain or the hypervariable regions CDR1, CDR2, and CDR3 of the light chain taken as a whole are at least about 80% homologous, at least about 90% homologous, or at least about 95% homologous to the hypervariable regions as shown in SEQ ID NO: 15 through SEQ ID NO. 26 or SEQ ID NO: 27 through SEQ ID NO: 40, respectively, and (ii) wherein the variant or mutant is capable of inhibiting the activity of human B7RP1 to the same extent as a reference anti-B7RP1 human antibody having framework regions identical to those of molecule X. Such antibodies may bind to human B7RP1 or to mouse B7RP1 or both. The mouse B7RP1 sequence is described in WO 00/46240, which is incorporated by reference.

Ordinarily, an anti-B7RP1 human antibody variant will have light and/or heavy chain CDRs, when taken as a whole, that are at least about 80% amino acid sequence identity, at least about 85% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% amino acid sequence identity to the amino acid sequence as shown in SEQ ID NOS: 15 through SEQ ID NO. 26 and/or SEQ ID NOS: 27 through SEQ ID NO. 40, respectively. Such antibodies may bind to human B7RP1 or to mouse B7RP1 or to both.

An anti-B7RP1 human antibody variant will have a light chain variable region, when taken as a whole, that has at least about 80% amino acid sequence identity, at least about 81% sequence identity, at least about 82% sequence identity, at least about 83% sequence identity, at least about 84% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% amino acid sequence identity to the amino acid sequence as shown in SEQ ID NOS: 1 through SEQ ID NO. 6, and/or a heavy chain variable region, when taken as a whole, that has at least about 70% amino acid sequence identity, at least about 75% sequence identity, at least about 80% sequence identity, at least about 81% sequence identity, at least about 82% sequence identity, at least about 83% sequence identity, at least about 84% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% amino acid sequence identity to the amino acid sequence as shown in SEQ ID NOS: 7 through SEQ ID NO. 14. Such antibodies may bind to human B7RP1 and/or mouse B7RP1.

As will be appreciated by those of skill in the art, many of the potential CDR-contact residues are amenable to substitution by other amino acids and still allow the antibody to retain substantial affinity for the antigen. Likewise, many of the framework residues not in contact with the CDRs in the heavy and light chains can accommodate substitutions of amino acids from the corresponding positions from other human antibodies, by human consensus amino acids, or from other mouse antibodies, without significant loss of the affinity or non-immunogenicity of the human antibody. Selection of various alternative amino acids may be used to produce versions of the disclosed anti-B7RP1 antibodies and fragments thereof that have varying combinations of affinity, specificity, non-immunogenicity, ease of manufacture, and other desirable properties.

A "variant" in reference to a polynucleotide is intended to refer to a nucleic acid molecule having at least about 75% nucleic acid sequence identity with a polynucleotide sequence of the present invention. Ordinarily, a polynucleotide variant will have at least about 75% nucleic acid sequence identity, at least about 80% nucleic acid sequence identity, at least about 81% nucleic acid sequence identity, at least about 82% nucleic acid sequence identity, at least about 83% nucleic acid sequence identity, at least about 84% nucleic acid sequence identity, at least about 85% nucleic acid sequence identity, at least about 86% nucleic acid sequence identity, at least about 87% nucleic acid sequence identity, at least about 88% nucleic acid sequence identity, at least about 89% nucleic acid sequence identity, at least about 90% nucleic acid sequence identity, at least about 91% nucleic acid sequence identity, at least about 92% nucleic acid sequence identity, at least about 93% nucleic acid sequence identity, at least about 94% nucleic acid sequence identity, at least about 95% nucleic acid sequence identity, at least about 96% nucleic acid sequence identity, at least about 97% nucleic acid sequence identity, at least about 98% nucleic acid sequence identity, or at least about 99% nucleic acid sequence identity with a novel nucleic acid sequence disclosed herein.

In alternative embodiments, antibodies of the invention can be expressed in cell lines other than hybridoma cell lines. In these embodiments, sequences encoding particular antibodies can be used for transformation of a suitable mammalian host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (all of which are hereby incorporated herein by reference for any purpose). Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

A nucleic acid molecule encoding the amino acid sequence of a heavy chain constant region, a heavy chain variable region, a light chain constant region, or a light chain variable region of an anti-B7RP1 antibody of the invention is inserted into an appropriate expression vector using standard ligation techniques. In one embodiment, the anti-B7RP1 antibody heavy chain or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see METHODS IN. ENZYMOLOGY 185 (Goeddel, ed.), 1990, Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the anti-B7RP1 antibody polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification or detection of the anti-B7RP1 antibody from the host cell. Affinity purification can be accomplished, for example, by column chromatography using antibodies against the tag as an affinity matrix. Optionally, the tag can subsequently be removed from the purified anti-B7RP1 antibody polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Exemplary selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody that binds to B7RP1 polypeptide. As a result, increased quantities of a polypeptide such as an anti-B7RP1 antibody are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such an area within the mature polypeptide.

Expression and cloning vectors of the invention will typically contain a promoter that is recognized by the host organism and operably linked to the molecule encoding the anti-B7RP1 antibody. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe genes to which they are operably linked, that is, with little or no control over gene expression. A large number of promoters, recognized by a variety of potential host cells, are well known. A suitable promoter is operably linked to the DNA encoding heavy chain or light chain comprising an anti-B7RP1 antibody of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Bernoist and Chambon, 1981, *Nature* 22:304-10); CMV promoter (Thomsen et al., 1984, *Proc. Natl Acad Sci. USA* 8:659-663); the promoter contained in the 3' long terminal repeat of Rous sarcoma virus (Yamamoto, et al., 1980, *Cell* 22:787-97); herpes thymidine kinase promoter (Wagner et al., 1981, *Proc. Natl Acad Sci. USA* 78:1444-45); promoter and regulatory sequences from the metallothionine gene (Brinster et al., 1982, *Nature* 296:39-42); and prokaryotic promoters such as the beta-lactamase promoter (Villa-Kamaroff et al., 1978, *Proc. Natl. Acad. Sci USA,* 72:3727-31); or the tac promoter (DeBoer et al, 1983, *Proc Natl. Acad Sci. U.S.A.,* 80:21-25). Also of interest are the following animal transcriptional control regions, which exhibit tissue specificity and have been utilized in transgenic animals: the elastase I gene control region that is active in pancreatic acinar cells (Swift et al, 1984, Cell 38:639-46; Ornitz et al., 1986, *Cold Spring Harbor Symp. Quant Biol.* 50:399-409 (1986); MacDonald, 1987, *Hepatology* 7:425-515); the insulin gene control region that is active in pancreatic beta cells (Hanahan, 1985, *Nature* 315:115-22); the immunoglobulin gene control region that is active in lymphoid cells (Grosschedl et al, 1984, *Cell* 38:647-58; Adames et al., 1985, *Nature* 318:533-38; Alexander et al, 1987, *Mol. Cell. Biol,* 7:1436-44); the mouse mammary tumor virus control region that is active in testicular, breast, lymphoid and mast cells (Leder et al, 1986, *Cell* 45:485-95); the albumin gene control region that is active in liver (Pinkert et al, 1987, *Genes and Devel.* 1:268-76); the alpha-feto-protein gene control region that is active in liver (Krumlauf et al, 1985, *Mol. Cell. Biol.,* 5:1639-48; Hammer et al., 1987, *Science* 235:53-58); the alpha 1-antitrypsin gene control region that is active in liver (Kelsey et al., 1987, *Genes and Devel.* 1:161-71); the beta-globin gene control region that is active in myeloid cells (Mogram et al., 1985, *Nature* 315:338-40; Kollias et al, 1986, *Cell* 46:89-94); the myelin basic protein gene control region that is active in oligodendrocyte cells in the brain (Readhead et al., 1987, *Cell* 48:703-12); the myosin light chain-2 gene control region that is active in skeletal muscle (Sani, 1985, *Nature* 314:283-86); and the gonadotropic releasing hormone gene control region that is active in the hypothalamus (Mason et al., 1986, *Science* 234:1372-78).

An enhancer sequence may be inserted into the vector to increase transcription of DNA encoding light chain or heavy chain comprising an anti-B7RP1 antibody of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an anti-B7RP1 antibody has been inserted into the proper site of the vector, the completed vector may be inserted into a suitable host cell for amplification and/or polypeptide expression. The transformation of an expression vector for an anti-B7RP1 antibody into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al, *supra*.

A host cell, when cultured under appropriate conditions, synthesizes an anti-B7RP1 antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antibodies with B7RP1 binding properties. In another embodiment, a cell line from the B cell lineage that does not make its own antibody but has a capacity to make and secrete a heterologous antibody can be selected.

Antibodies of the invention are useful for detecting B7RP1 in biological samples and identification of cells or tissues that produce B7RP1 protein. Antibodies of the invention that specifically bind to B7RP1 may be useful in treatment of B7RP1 mediated diseases. Said antibodies can be used in binding assays to detect B7RP1 and to inhibit B7RP1 from forming a complex with B7RP1 receptors. Said antibodies that bind to B7RP1 and block interaction with other binding compounds may have therapeutic use in modulating B7RP1 mediated diseases. In certain embodiments, antibodies to B7RP1 may block B7RP1 binding to its receptor, which may result in disruption of the B7RP1 induced signal transduction cascade.

The present invention also relates to the use of one or more of the antibodies of the present invention in the manufacture of a medicament for the treatment of a disorder or condition caused by increased expression of B7RP1 or increased sensitivity to B7RP1 in a patient such as any one of disorders or conditions disclosed herein.

In certain embodiments, the invention provides pharmaceutical compositions comprising a therapeutically effective amount of one or a plurality of the antibodies of the invention together with a pharmaceutically acceptable diluent, carrier, solubilizer, emulsifier, preservative and/or adjuvant. Acceptable formulation materials are nontoxic to recipients at the dosages and concentrations employed. In preferred embodiments, pharmaceutical compositions comprising a therapeutically effective amount of anti-B7RP1 antibodies are provided.

In certain embodiments, acceptable formulation materials are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, for example, sodium or potassium chloride, mannitol sorbitol); delivery vehicles; diluents; excipients and/or pharmaceutical adjuvants. See REMINGTON'S PHARMACEUTICAL SCIENCES, 18$^{th}$ Edition, (A.R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, *supra*. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In certain embodiments, pharmaceutical compositions of the present invention comprise Tris buffer of about pH 7.0-8.5, or acetate buffer of about pH 4.0-5.5, and may further include sorbitol, sucrose, Tween-20 and/or a suitable substitute therefor. In certain embodiments of the invention, anti-B7RP1 antibody compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the anti-B7RP1 antibody product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired anti-B7RP1 antibody in a pharmaceutically acceptable vehicle. A particularly suitable vehicle for parenteral injection is sterile distilled water in which the anti-B7RP1 antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody molecule.

Pharmaceutical compositions of the invention can be formulated for inhalation. In these embodiments, anti-B7RP1 antibodies are advantageously formulated as a dry, inhalable powder. In certain embodiments, anti-B7RP1 antibody inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. Anti-B7RP1 antibodies that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the anti-B7RP1 antibody. Diluents, flavorings, low melting point waxes, vegetable oils, lubricants, suspending agents, tablet disintegrating agents, and binders may also be employed.

A pharmaceutical composition of the invention is provided to comprise an effective quantity of one or a plurality of anti-B7RP1 antibodies in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving anti-B7RP1 antibodies in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al, 1983, *Biopolymers* 22:547-556), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(-)-3-hydroxybutyric acid (European Patent Application Publication No. EP 133,988). Sustained release compositions may also include liposomes that can be prepared by any of several methods known in the art. See e.g., Eppstein et al, 1985, *Proc. Natl. Acad Sci. USA* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The effective amount of an anti-B7RP1 antibody-containing pharmaceutical composition to be employed therapeutically will depend, for example, upon the therapeutic context and objectives. One skilled in the art will appreciate that the appropriate dosage levels for treatment will vary depending, in part, upon the molecule delivered, the indication for which the anti-B7RP1 antibody is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In certain embodiments, the dosage may range from 0.1 pig/kg up to about 30 mg/kg; from 1 µg/kg up to about 30 mg/kg; or from 5 µg/kg up to about 30 mg/kg.

Dosing frequency will depend upon the pharmacokinetic parameters of the particular anti-B7RP1 antibody in the formulation used. Typically, a clinician administers the composition until a dosage is reached that achieves the desired effect.

The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, the antibodies of the invention can be administered to patients throughout an extended time period. Chronic administration of an antibody of the invention minimizes the adverse immune or allergic response commonly associated with antibodies that are raised against a human antigen in a non-human animal, for example, a non-fully human antibody produced in a non-human species.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use anti-B7RP1 antibody pharmaceutical compositions according to the invention ex vivo. In such instances, cells, tissues or organs that have been removed from the patient are exposed to anti-B7RP1 antibody pharmaceutical compositions after which the cells, tissues and/or organs are subsequently implanted back into the patient.

In particular, anti-B7RP1 antibodies can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

The following examples, including the experiments conducted and results achieved are provided for illustrative purposes only and are not to be construed as limiting the invention.

Example 1

Production of Human Monoclonal Antibodies Against B7 Related Protein-1 (B7RP1)

Antigen

Purified recombinant human B7RP-1 (hB7RP-1) prepared as described in International Patent Application Publication No. WO 00/46240, which is incorporated herein by reference, or CHO cells transfected to express hB7RP-1 were used as the antigen. Mature human B7RP-1 has the amino acid sequence of residues X to 302 in the sequence shown in WO 00/46240 as SEQ ID NO: 17, wherein X can be 19, 20, 21, 22, 24 or 28.

Transgenic HuMab Mice

Fully human monoclonal antibodies to B7RP-1 were prepared using HCo7 and HCo12 strains of HuMab transgenic mice, both of which express human antibody genes. In both of these mouse strains, the endogenous mouse kappa light chain gene has been homozygously disrupted as described in Chen et al (1993) *EMBO J.* 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) *Nature Biotechnology* 14:845-851. The HCo7 strain carries the HCo7 human heavy chain transgene as described in U.S. Pat. Nos. 5,545,806; 5,625,825; and 5,545,807. The HCo12 strain carries the HCo12 human heavy chain transgene as described in Example 2 of PCT Publication WO 01/09187.

HuMab Immunizations:

To generate fully human monoclonal antibodies to B7RP-1, HuMab mice of the HCo7 or HCo12 strain were immunized with purified recombinant B7RP-1 or CHO cells transfected to express B7RP-1. General immunization schemes for HuMab mice are described in Lonberg et al (1994) *Nature* 368(6474): 856-859; Fishwild et al. (1996) *Nature Biotechnology* 14: 845-851 and PCT Publication WO 98/24884. The mice were 6-16 weeks of age upon the first infusion of antigen. A purified recombinant preparation of B7RP-1 antigen (50 µg) or a preparation of transfected CHO cells (3.5×10⁶-1×10⁷ cells) was used to immunize the HuMab mice intraperitonealy.

Transgenic mice were immunized twice with purified antigen in complete Freund's adjuvant intraperitonealy, followed by 2-4 weeks of IP immunizations (up to a total of 8 immunizations) with the purified antigen in incomplete Freund's adjuvant. Immunization with CHO cells transfected to express B7RP-1 was the same except that complete Freund's adjuvant and incomplete Freund's adjuvant were not used with the cells. The immune response was monitored by retroorbital bleeds. The plasma was screened by ELISA (as described below), and mice with sufficient titers of anti-B7RP-1 human immunogolobulin were used for fusions. Mice were boosted intravenously with antigen 3 and 2 days before sacrifice and removal of the spleen. Typically, 10-20 fusions for each antigen were performed. Several dozen mice were immunized for each antigen. A total of 28 mice of the HCo7 and HCo12 mice strains were immunized with B7RP-1.

Selection of HuMab Mice Producing Anti-B7RP-1 Antibodies:

To select HuMab mice producing antibodies that bound B7RP-1, sera from immunized mice was tested by ELISA as described by Fishwild et al. (1996). Briefly, microtiter plates were coated with purified recombinant B7RP-1 at 1-2 µg/ml in PBS, 50 µl/wells incubated 4° C. overnight then blocked with 200 µl/well of 5% chicken serum in PBS/Tween (0.05%). Dilutions of plasma from B7RP-1-immunized mice were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495. Mice that developed the highest titers of anti-B7RP-1 antibodies were used for fusions. Fusions were performed as described below and hybridoma supernatants were tested for anti-B7RP-1 activity by ELISA.

Generation of Hybridomas Producing Human Monoclonal Antibodies to B7RP-1.

The mouse splenocytes, isolated from the HuMab mice, were fused with PEG to a mouse myeloma cell line based upon standard protocols. The resulting hybridomas were then screened for the production of antigen-specific antibodies. Single cell suspensions of splenic lymphocytes from immunized mice were fused to one-fourth the number of SP2/0 nonsecreting mouse myeloma cells (ATCC, CRL 1581) with 50% PEG (Sigma). Cells were plated at approximately 1×10⁵/well in flat bottom microtiter plate, followed by about two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by ELISA (described above) for human anti-B7RP-1 monoclonal IgG antibodies. Once extensive hybridoma growth occurred, medium was monitored usually after 10-14 days. The antibody secreting hybridomas were replated, screened again and, if still positive for human IgG, anti-B7RP-1 monoclonal antibodies were subcloned at least twice by limiting dilution. The stable subclones were then cultured in vitro to generate small amounts of antibody in tissue culture medium for further characterization.

Example 2

Cloning the Anti-B7RP1 Antibody Heavy and Light Chains

The hybridoma expressing the B7RP1 binding monoclonal antibody 16H was used as a source to isolate total RNA using TRIzol® reagent (Invitrogen). A 5' RACE (rapid amplification of cDNA ends) oligonucleotide (5'-CGA CUG GAG CAC GAG GAC ACU GAC AUG GAC UGA AGG AGU AGA AA-3'; SEQ ID NO: 69) was ligated to the RNA using the GeneRacer™ Kit (Invitrogen) components and protocol. First strand cDNA was synthesized using a random primer with an extension adapter (5'-_GGC CGG ATA GGC CTC CAN NNN NNT-3') (SEQ ID NO: 59) and a 5' RACE (rapid amplification of cDNA ends) preparative assay was performed using the GeneRacer™ Kit (Invitrogen) according to instructions from the manufacturer. For preparing complete light chain encoding cDNA, the forward primer was the GeneRacer™ nested primer, and the reverse primer was (5'-GGG GTC AGG CTG GAA CTG AGG-3') (SEQ ID NO: 60). For preparing cDNA encoding the variable region of the heavy chain, the forward primer was the GeneRacer™ nested primer and the reverse primer was (5'-TGA GGA CGC TGA CCA CAC G-3') (SEQ ID NO: 61). RACE products were cloned into pCR4-TOPO (Invitrogen) and the sequences determined. Consensus sequences were used to design primers for full-length antibody chain PCR amplification.

For preparing cDNA encoding anti-B7RP1 16H kappa light chain, the 5' PCR primer encoded the amino terminus of the signal sequence, an XbaI restriction enzyme site, and an optimized Kozak sequence (5'-CAG CAG AAG CTT CTA GAC CAC CAT GGA CAT GAG GGT CCT CGC TCA GCT CCT GGG-3') (SEQ ID NO: 62). The 3' primer encoded the carboxyl terminus and termination codon, as well as a SalI restriction site (5'-CTT GTC GAC TCA ACA CTC TCC CCT GTT GAA GCT C-3') (SEQ ID NO: 63). The resulting PCR product fragment was purified, digested with XbaI and SalI, and then gel isolated and ligated into the mammalian expression vector pDSRα20 (see International Application, Publication No. WO 90/14363, which is herein incorporated by reference for any purpose. pDSRα20 was produced by changing nucleotide 2563 in pDSRα19 from a "Guanosine" to an "Adenosine" by site directed mutagenesis.).

For preparing cDNA encoding anti-B7RP1 16H heavy chain the 5' PCR primer encoded the amino terminus of the signal sequence, an XbaI restriction enzyme site, and an optimized Kozak sequence (5'-ACA ACA AAG CTT CTA GAC CAC CAT GGA GTT GGG GCT GAA CTG G-3') (SEQ ID NO: 64). The 3' primer encoded the carboxyl end of the variable region, Including a naturally occurring sense strand BsmBI site (5'-GTG GAG GCA CTA GAG ACG GTG ACC AGG ATT CC-3'; SEQ ID NO: 65). The resulting product was purified, digested with XbaI and BsmBI, gel isolated and ligated into the pDSRα20 vector containing the human IgG1 constant region and also into the pDSRα20 vector containing the human IgG2 constant region. All of the hybridoma derived anti-B7RP1 heavy chain variable regions, regardless of the native constant region associated, were cloned as described above into both the pDSRα20 vectors containing the human IgG1 and the human IgG2 constant regions.

Example 3

Expression of Anti-B7RP1 Antibodies in Chinese Hamster Ovary (CHO) Cells

Stable expression of the 16H anti-B7RP1 mAb was achieved by co-transfection of 16H-heavy chain/pDSRα19 IgG2 B7RP1-kappa/pDSRα19 plasmids into dihydrofolate reductase deficient (DHFR⁻) serum-free adapted Chinese hamster ovary (CHO) cells using a calcium phosphate method (the full length 16H heavy chain sequence is shown in SEQ ID NO: 44; the 16H kappa chain sequence is shown in SEQ ID NO: 45). Transfected cells were selected in medium containing dialyzed serum but not containing hypoxanthine-thymidine to ensure the growth of cells expressing the DHFR enzyme. Transfected clones were screened using assays such as ELISA in order to detect the expression of 16H anti-B7RP1 mAb in the conditioned medium. The highest expressing clones were subjected to increasing concentrations of methotrexate (MTX) for DHFR amplification. MTX amplified clones were screened using assays such as ELISA in order to detect higher expression of 16H anti-B7RP1 mAb in the conditioned medium. The highest expressing clones were subjected to subcloning to obtain a homogeneous population and creation of cell banks.

Other recombinant anti-B7RP1 antibodies of the invention can be generated in Chinese hamster ovary cells deficient in DHFR using the same protocol as described above for the anti-B7RP1 monoclonal antibody. The DNA sequences encoding the complete heavy chain or light chain of each anti-B7RP1 antibody of the invention are cloned into expression vectors. CHOd-cells are co-transfected with an expression vector capable of expressing a complete heavy chain and an expression vector expressing the complete light chain of the appropriate anti-B7RP1 antibody. For example, to generate a 5D anti-B7RP1 antibody, cells are co-transfected with a vector capable of expressing a complete heavy chain comprising the amino acid sequence as set forth in SEQ ID NO: 47 and a vector capable of expressing a complete light chain comprising the amino acid sequence set forth in SEQ ID NO: 48. Table 2 summarizes exemplary complete light chains and exemplary complete heavy chains for anti-B7RP1 antibodies having human IgG heavy chain constant regions. One of skill in the art will recognize that the IgG1 or IgG2 could be substituted for each other (i.e. where IgG1 is listed in the table, IgG2 could be present, and vice versa). Alternatively, any other immunoglobulin (e.g., IgM, IgA, IgE or IgH) could be used to generate antibodies of the invention.

TABLE 2

| Antibody | Heavy Chain Variable Region + Heavy Chain Constant Region | Complete Heavy Chain |
| --- | --- | --- |
| 16H(IgG2) | SEQ ID NO: 7 + SEQ ID NO: 41 | SEQ ID NO: 44 |
| 16H(IgG1) | SEQ ID NO: 7 + SEQ ID NO: 42 | SEQ ID NO: 70 |
| 16Hg(IgG2) | SEQ ID NO: 8 + SEQ ID NO: 41 | SEQ ID NO: 46 |
| 16Hg(IgG1) | SEQ ID NO: 8 + SEQ ID NO: 42 | SEQ ID NO: 71 |
| 5D(IgG1) | SEQ ID NO: 9 + SEQ ID NO: 42 | SEQ ID NO: 47 |
| 5D(IgG2) | SEQ ID NO: 9 + SEQ ID NO: 41 | SEQ ID NO: 72 |
| 2H(IgG2) | SEQ ID NO: 10 + SEQ ID NO: 41 | SEQ ID NO: 49 |
| 2H(IgG1) | SEQ ID NO: 10 + SEQ ID NO: 42 | SEQ ID NO: 73 |
| 2Hg(IgG2) | SEQ ID NO: 11 + SEQ ID NO: 41 | SEQ ID NO: 51 |
| 2Hg(IgG1) | SEQ ID NO: 11 + SEQ ID NO: 42 | SEQ ID NO: 74 |
| 43H(IgG2) | SEQ ID NO: 14 + SEQ ID NO: 41 | SEQ ID NO: 52 |
| 43H(IgG1) | SEQ ID NO: 14 + SEQ ID NO: 42 | SEQ ID NO: 75 |
| 41H(IgG2) | SEQ ID NO: 13 + SEQ ID NO: 41 | SEQ ID NO: 54 |
| 41H(IgG1) | SEQ ID NO: 13 + SEQ ID NO: 42 | SEQ ID NO: 76 |
| 15H(IgG2) | SEQ ID NO: 12 + SEQ ID NO: 41 | SEQ ID NO: 56 |
| 15H(IgG1) | SEQ ID NO: 12 + SEQ ID NO: 42 | SEQ ID NO: 57 |

TABLE 2-continued

| Antibody | Light Chain Variable Region + Light Chain Constant Region | Complete Light Chain |
| --- | --- | --- |
| 16H | SEQ ID NO: 1 + SEQ ID NO: 43 | SEQ ID NO: 45 |
| 5D | SEQ ID NO: 2 + SEQ ID NO: 43 | SEQ ID NO: 48 |
| 2H | SEQ ID NO: 3 + SEQ ID NO: 43 | SEQ ID NO: 50 |
| 43H | SEQ ID NO: 6 + SEQ ID NO: 43 | SEQ ID NO: 53 |
| 41H | SEQ ID NO: 5 + SEQ ID NO: 43 | SEQ ID NO: 55 |
| 15H | SEQ ID NO: 4 + SEQ ID NO: 43 | SEQ ID NO: 58 |

Example 4

Production of anti-B7RP1 Antibody

Anti-B7RP1 antibody is produced by expression in a clonal line of CHO cells. For each production run, cells from a single vial are thawed into serum-free cell culture media. The cells are grown initially in a T-flask followed by spinner flasks and then grown in stainless steel reactors of increasing scale up to a 2000 L bioreactor. Production is carried out in a 2000 L bioreactor using a fed batch culture, in which a nutrient feed containing concentrated media components is added to maintain cell growth and culture viability. Production lasts for approximately two weeks during which time anti-B7RP1 antibody is constitutively produced by the cells and secreted into the cell culture medium.

The production reactor is controlled at a predetermined pH, temperature, and dissolved oxygen level: pH is controlled by carbon dioxide gas and sodium carbonate addition; dissolved oxygen is controlled by air, nitrogen, and oxygen gas flows.

At the end of production, the cell broth is fed into a disk stack centrifuge and the culture supernatant is separated from the cells. The concentrate is further clarified through a depth filter followed by a 0.2 µm filter. The clarified conditioned media is then concentrated by tangential flow ultrafiltration. The conditioned media is concentrated 15- to 30-fold. The resulting concentrated conditioned medium is then either processed through purification or frozen for purification at a later date.

Example 5

Germlining the 16H mAb

Sequence alignment of the 16H antibody with human germline sequences showed that the framework sequence in the variable region of the 16H antibody was most identical to the $V_H$ 3-07 and JH4 germline sequences, with only three amino acid differences (FIG. 1A). The framework sequence for the VK region of the 16H antibody was found to be identical to the VK1-L15 germline sequence. It is theoretically possible that somatic hypermutations are recognized as foreign by the immune response of a patient; in which case the patient would generate an anti-idiotype response that could neutralize the therapeutic. To reduce this possibility, the three amino acid changes in the VH framework region were converted back to the $V_H$ 3-07 and JH4 germline sequences (FIG. 1A). Since the germline $V_H$ and $J_H$ gene segments are present in every human genome, the germline version of 16H is not likely to be recognized as foreign by the immune response of a dosed patient. Plate co-stimulation bioassays were conducted to determine if the germlined antibodies could induce T-cell proliferation with an $IC_{50}$ similar to the $IC_{50}$ of the non-germlined antibodies. The co-stimulation assays were conducted as described below using anti-CD3 and hB7RP-1-Fc fusion protein confirmed that this germlined antibody, referred to as 16Hgermline or 16Hg, retains its biological activities (FIG. 1B).

Example 6

Affinity Measurement of Monoclonal Antibodies by Biacore® and KinExA

Figure 2:
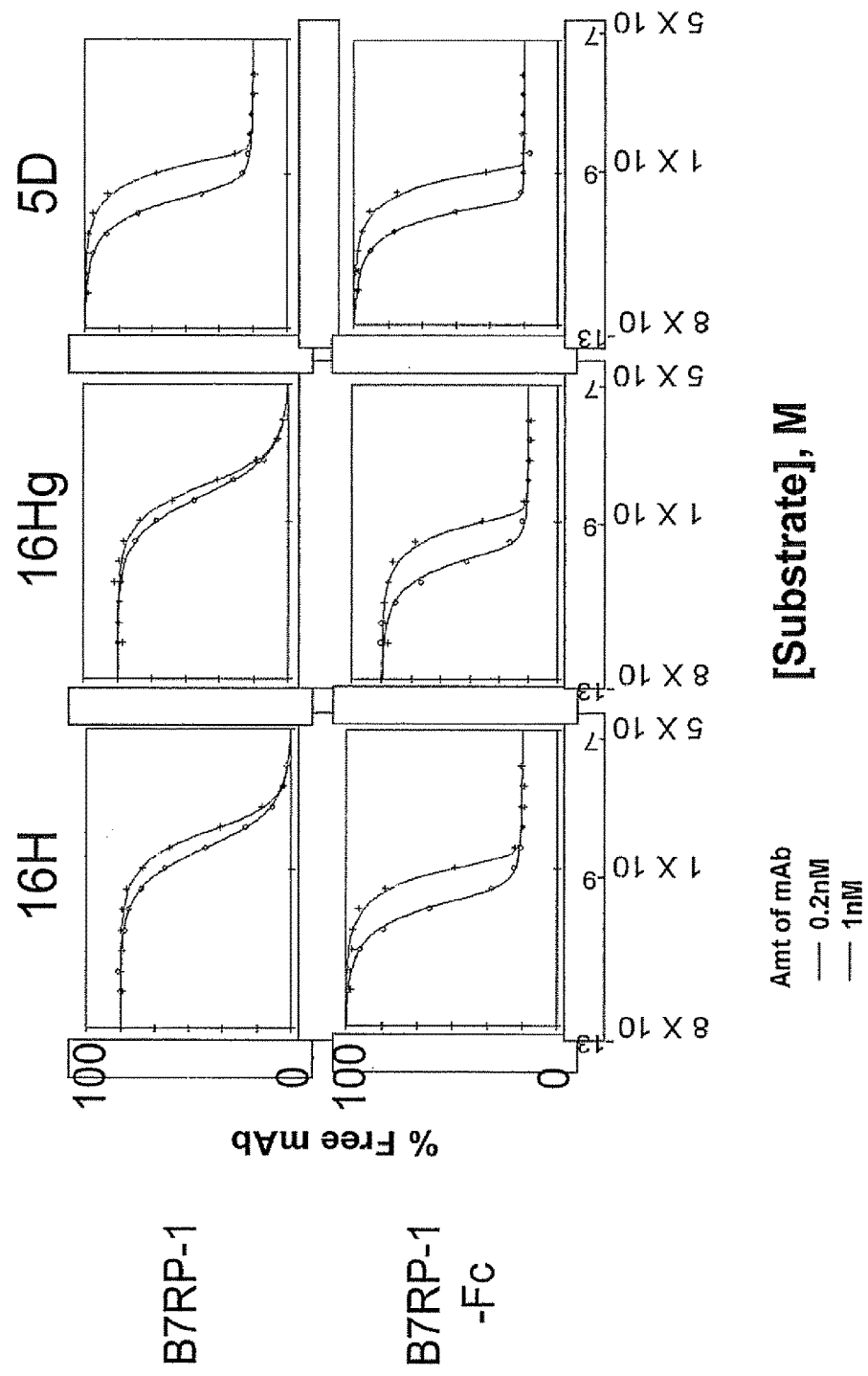
FIG. 2 shows the results of Biacore® binding assays with 16H, 16Hg, and 5D antibodies.

Three antibodies (5D and 16H, prepared as described in Example 1, and 16H germline, prepared as described in Example 5) were purified and submitted to binding affinity analysis. B7RP-Fc was immobilized at a high density on a CM5 sensor chip using standard amine coupling chemistry. A fixed concentration of mAb was then incubated with varying concentrations of B7RP-1 or B7RP1-Fc for at least eight hours at room temperature to allow them to reach equilibrium. The samples were then injected over the B7RP1-Fc surface, and the binding signal observed represented free antibody remaining in solution at equilibrium. By using two different antibody concentration (0.2 nM and 1 nM), the $K_D$ of the interaction between a particular mAb and ligand was calculated from nonlinear regression analysis of the competition curves using a dual-curve one-site homogeneous binding model (Adamczyk et al, 1999, *Bioconjugate Chem.* 10:1032-37; Adamczyk et al., 2000, *Methods* 20:319-28). As shown in FIG. 2 and Table 3, the 16H, 16Hg, and 5D mAbs all bound both soluble B7RP-1 and B7RP-1-Fc proteins at high affinities. In addition, the results indicated that the 16H (non-germline) and the 16Hg (germline) reacted similarly, demonstrating that germlining did not significantly affect binding between antibody and ligand.

TABLE 3

Summary of $K_D$ Values

|  | B7RP-1 | B7RP1-Fc |
|---|---|---|
| 5D | 37 pM | 1.6 pM |
| 16H | 1.9 nM | 27 pM |
| 16H (germline) | 2.7 nM | 17 pM |

Binding of 5D, 2H, and 2H germline antibodies was also tested using KinExA (kinetic exclusion assay) technology. In this assay, hB7RP-1 was coupled to agarose beads. The beads were used to create a bead column. Samples containing antibody at a fixed concentration, which were allowed to come to equilibrium with varying concentrations of hB7RP-1, were then passed over the bead column. Antibody not complexed with ligand bound to the coated beads.

Figure 3:
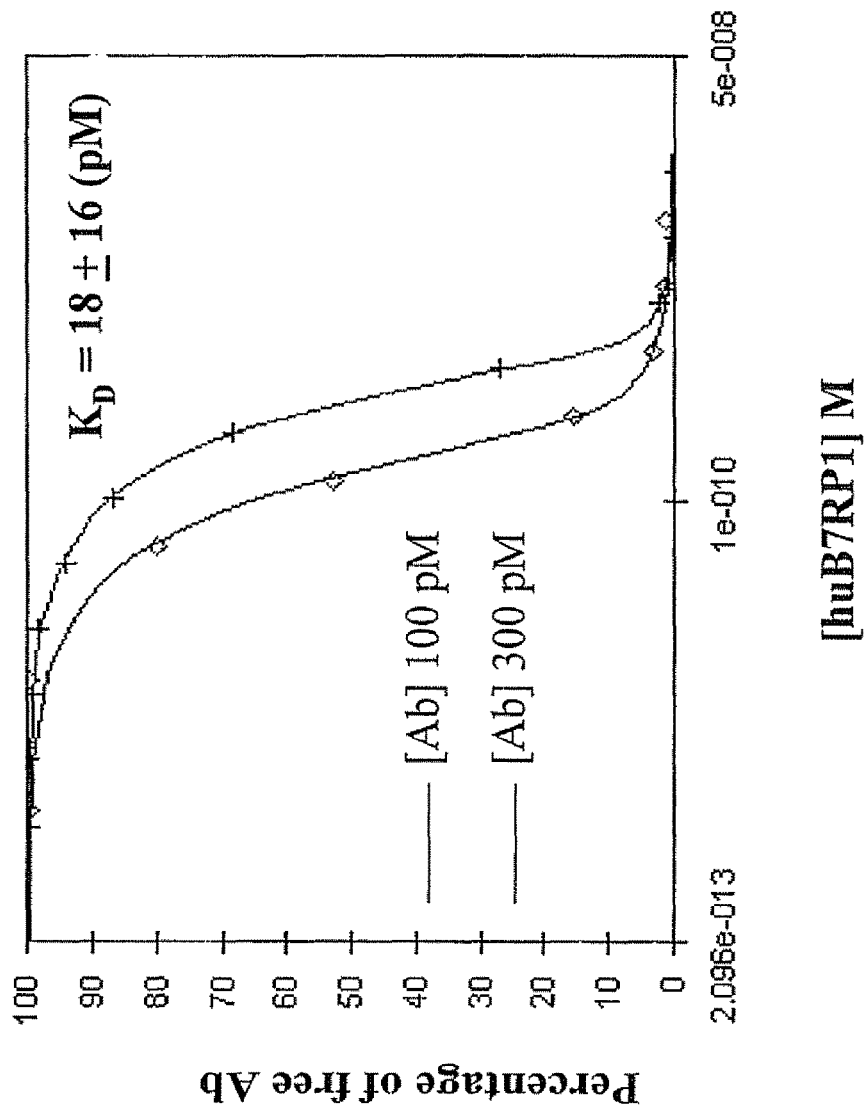
FIG. 3 shows the results of KinExA binding assay with 5D antibody.
Figure 4:
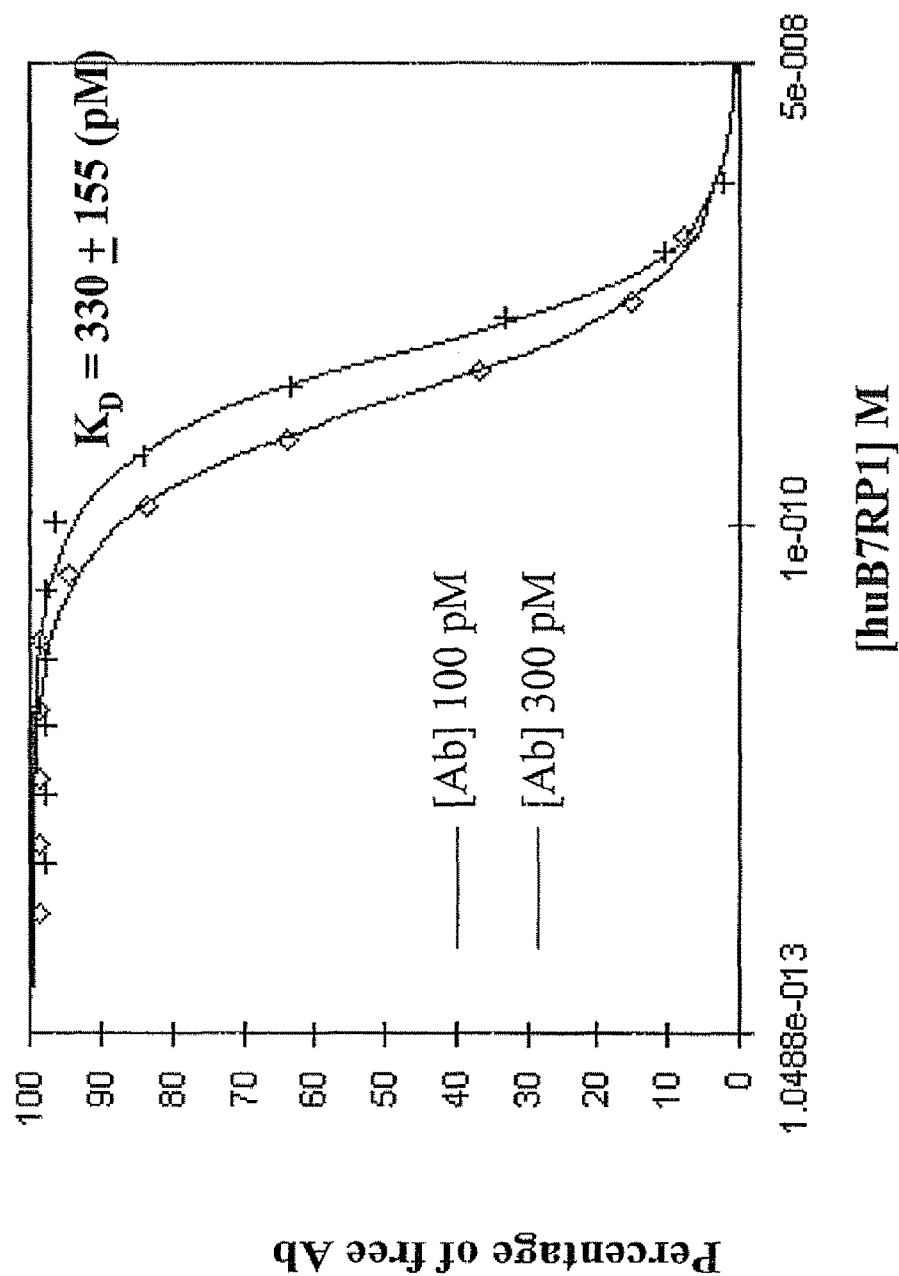
FIG. 4 shows the results of KinExA binding assay with 2H antibody.
Figure 5:
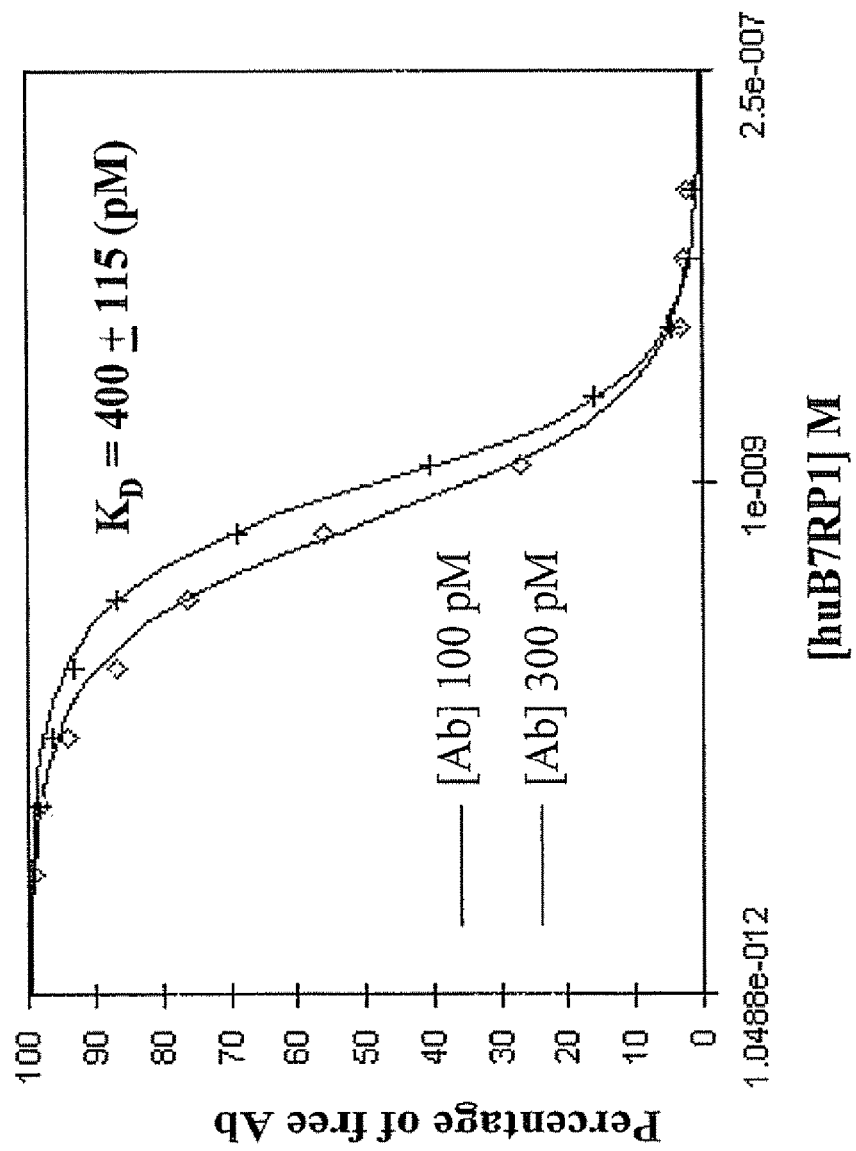
FIG. 5 shows the results of KinExA binding assay with 2H germline (2Hg) antibody.

A fluorescent tagged anti-human Fc secondary antibody was used to detect bound test antibody. The signal obtained was proportional to free antibody in solution at a given ligand concentration. Using two different antibody concentrations, the $K_D$ of the interaction was calculated from nonlinear regression analysis of the competition curves using a dual-curve one-site homogeneous binding model (Adamczyk et al., 1999, *Bioconjugate Chem.* 10:1032-37; Adamczyk et al., 2000, *Methods* 20:319-28). FIGS. 3, 4, and 5 show the dual-curve fits for antibodies 5D, 2H and 2H(germline). Using this technique, an approximately 10-fold difference was seen in the $K_D$s for antibodies 5D and 2H.

The results of the Biacore® and KinExA assays demonstrated that antibody 5D has a higher affinity for hB7RP-1 than do either 2H or 16H. Also, the germline version of antibody 2H does not show a significant difference from the non-germline construct.

Example 7

Functional Characteristics of anti-B7RP1 Antibodies

The functional characteristics of B7RP-1 antibodies of the invention were evaluated using binding-competition assays, in vitro co-stimulation assays and in vitro tetanus toxoid assays.

Binding-Competition Studies

Figure 6:
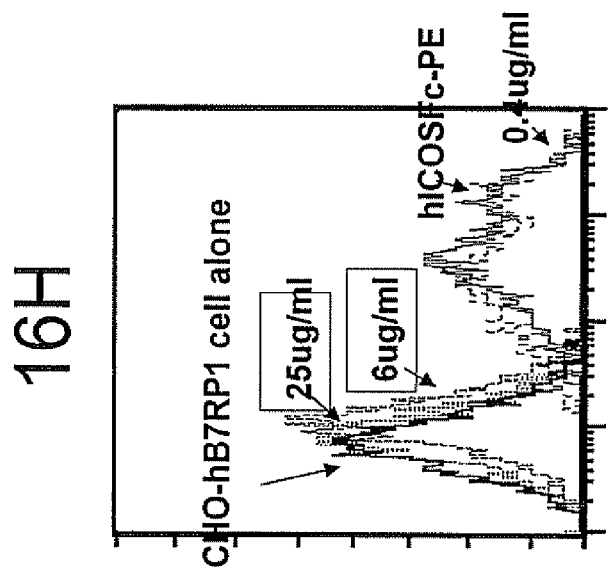
FIG. 6 depicts the results of binding-competition assays showing that 16H antibody competes away binding of ICOS-Fc on B7RP-1, analyzed by flow cytometry.

Binding-competition studies were conducted with the 16H mAbs to demonstrate that they can compete for ICOS binding for B7RP-1. CHO cells transfected with a gene encoding the full-length human B7RP-1 were first incubated with decreasing amounts of unlabeled 16H mAb and subsequently stained with a fluorescently-labeled ICOS-Fc fusion protein. The cells were then analyzed using flow cytometry. As shown in FIG. 6, ICOS-Fc stained the B7RP-1-transfected CHO cells; 0.4 µg/ml of 16H mAb did not affect ICOS-Fc binding. However, 6 and 25 µg/ml of 16H efficiently competed away ICOS-Fc binding, indicating that the 16H mAb indeed competed for ICOS binding on B7RP-1.

Co-Stimulation Assays

Cell culture plates (Falcon, Cat No. 353077, U bottom) were coated with 1 µg/ml anti-human CD3 antibodies (PharMingen Cat No. 555336) and 10 ug/ml anti-human IgG (Fc specific, Sigma Cat No. 13391). The anti-CD3 antibodies and anti-human immunoglobulin in phosphate buffered saline (PBS) were added to each well (100 l/well). The coated plates were incubated at 4° C. overnight or at room temperature for 2 hours. The plates were then washed with PBS twice. After washing, 1 µg/ml human B7-2Fc (R&D System, Cat No. 141-B2) or 5 µg/ml hB7RP1Fc, each diluted in PBS, were added to each well (100 µl per well). The plates were then incubated at room temperature for 3 hours and washed twice with PBS thereafter. Purified human T cells were added ($1 \times 10^5$ per well) in 200 µl volume of media (RPMI 1640 supplemented with 10% fetal calf serum (FCS), penicillin-streptomycin-L-glutamine (PSG), β-mercpatoethanol (2-ME), N-Acetyl aspartate (NAA) and Napyruvate) and incubated at 37° C., 5% $CO_2$ for 48 hours. $^3$H thymidine (ICN Cat No. 2404205) was added at 1 µCi/well and the cells were incubated overnight at 37° C., 5% $CO_2$. The cells were then harvested and counted.

Cell culture plates (Falcon, Cat No. 353077, U bottom) were coated with 0.1 µg/ml anti-human CD3 as above. hB7RP1 transfected CHO cells (5000RAD irradiated) were added at $2 \times 10^4$ per well followed by purified human T cells at $1 \times 10^5$ per well in 200 µl volume. Plates were incubated at 37° C., 5% $CO_2$ for 48 hours as above. $^3$H thymidine was added at 1 µCi/well. Cells were incubated overnight, harvested, and counted as above.

Tetanus Toxoid Assays

PBMC were purified from human blood using a Ficoll-Paque (Amersham Biosciences) gradient as follows. Blood was diluted 1:2 with PBS, diluted blood was layered on top of the Ficoll (1/3 room temp Ficoll+2/3 diluted blood), centrifuged at 2500 rpm for 30 minutes at room temperature, the top layer (plasma & platelets) was aspirated off, and the mononuclear cell layer was transferred to a fresh 50 ml tube. The isolated PBMC were washed with PBS (3× the volume of the mononuclear cell layer) and centrifuged for 10 minutes at 1300 rpm at room temperature and washed as above. The PBMC were resuspended in media (RPMI 1640+10% heat-inactivated FBS+1×PSO+1×NEAA+55 µM 2-ME) and the cells were counted.

PMBC were added to wells of a 96-well round bottom plate at 100 µl PBMC/well ($3 \times 10^6$/ml). Tetanus toxoid (20

µg/ml; University of Massachusetts) was added for a final concentration of 5 µg/ml. The cells were incubated for 3 days at 37° C.; 100 µl supernatant were collected and incubated for an addition 6 to 8 hours in the presence of 1 µCi/well $^3$H-thymidine (MP Biomedicals). The cells were then harvested and counted.

Table 4 summarizes the functional characteristics of certain antibodies of the invention as determined using the assays described above.

TABLE 4

|        | Plate     | Biacore Fc | Biacore mono | CHO    | Tetanus Toxoid |
|--------|-----------|------------|--------------|--------|----------------|
| 2H     | 43        | 89         |              | 1445   | 15             |
| 15H    | 36        |            |              |        | 141            |
| 16H    | 53        | 27         | 1900         | 276    | 27             |
| 16Hg   | 32        | 17         | 2700         | 523    |                |
| 41H    | 52        |            |              |        | 115            |
| 43H    | 46        |            |              |        | 35             |
| 5D     | 55        | 1.6        | 37           | 1456   | 15             |
| ICOS-Fc | 200-1000 | 1000       |              | 10,672 |                |
| α-CD86 |           |            |              |        | 40             |

*EC$_{50}$/KD values in pM

Example 8

Epitope Mapping

Experiments were conducted to identify the region on B7RP-1 to which the 16H/16Hg and 5D monoclonal antibodies bind. To do this, a novel Fluorescence-Activated Cell Sorter (FACS) binding assay was developed. The human extracellular domain (ECD) of B7RP1 (SEQ ID NO: 66) as well as truncated forms of B7RP-1 containing either the Ig1 (IgV-like; SEQ ID NO: 67) or the I82 (IgC-like; SEQ ID NO: 68) were expressed as N-terminal, in-frame fusions with chicken avidin.

```
SEQ ID NO: 66 (ECD):
DTQEKEVRAMVGSDVELSCACPEGSRFDLNDVYVYWQTSESKTVVTYHIP

QNSSLENVDSRYRNRALMSPAGMLRGDFSLRLFNVTPQDEQKFHCLVLSQ

SLGFQEVLSVEVTLHVAANFSVPVVSAPHSPSQDELTFTCTSINGYPRPN

VYWINKTDNSLLDQALQNDTVFLNMRGLYDVVSVLRIARTPSVNIGCCIE

NVLLQQNLIVGSQTGNDIGERDKITENP

SEQ ID NO: 67 (IgV-like):
DTQEKEVRAMVGSDVELSCACPEGSRFDLNDVYVYWQTSESKTVVTYHIP

QNSSLENVDSRYRNRALMSPAGMLRGDFSLRLFNVTPQDEQKFHCLVLSQ

SLGFQEVLSVEVTLHVAANFSVPVVSAPHSPSQDELTFT

SEQ ID NO: 68 (IgC-like):
LGFOEVLSVEVTLHVAANESVPVVSAPHSPSQDELTFTCTSINGYPRPNV

YWINKTDNSLLDQALQNDTVFLNMRGLYDVVSVLRIARTPSVNIGCCIEN

VLLQQNLTVGSQTGNDIGERDKITENP
```

Figure 9A:
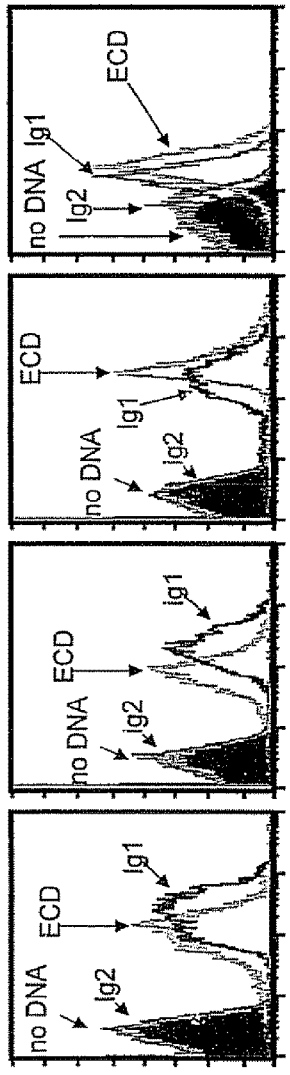
FIG. 9A shows fluorescent staining of B7RP1 extracellular domain (ECD) with labeled 16H, 5D, and ICOS antibodies.

Expression vectors containing genes encoding these fusion proteins were individually transiently transfected into 293T cells and the conditioned media from these cell lines were used as the source of fusion protein. The avidin-tag was used to capture the B7RP1 fusion proteins from solution using a biotin-coated bead. Fusion proteins were incubated with either fluorescently-labeled 16H or 5D mAbs or a fluorescently-labeled ICOS-Fc fusion protein, and incubated with biotin-coated beads. The beads were recovered and analyzed using flow cytometry on a Becton-Dickinson Bioscience FACScan (BD, Franklin Lakes, N.J.). As shown in FIG. 9A, fluorescent staining of the beads was detected with the 16H, 5D, and the ICOS reagents when the full ECD of B7RP-1 was attached, indicating that all three of these reagents could bind to the ECD of B7RP-1. Similarly, all three reagents bound to the avidin fusion protein containing only the Ig1 domain, indicating that both ICOS and the blocking anti-B7RP-1 mAbs could bind to this region. In contrast, neither ICOS nor the anti-B7RP-1 mAbs could bind to the fusion protein containing only the membrane-proximal Ig2 domain. Thus, the ICOS, 16H, and 5D binding regions on B7RP-1 were located in the Ig1 domain.

The antibodies generated as described above in Example 1 and tested for binding using the avidin fusion binding assay, could be divided into two epitope classes, H and D, as shown in Table 5. Of the 100 antibodies initially selected based on their ability to bind B7RP1, 15 failed to bind in the avidin fusion binding assay, most likely because of degradation.

TABLE 5

Classification of mAbs by epitope

| Class                          | # |
|--------------------------------|----|
| H epitope                      | 75 |
| D epitope                      | 10 |
| New epitope, ICOS blocker      | 0  |
| New epitope, not an ICOS blocker | 0  |
| No detectable binding          | 15 |

Example 9

SNP Identification and Functional Analysis

One major single nucleotide polymorphism (SNP) variant was identified in B7RP-1 that is present in the population with an allele frequency of 28.4% (FIG. 7). The variant was identified within the mature protein coding sequence. A search of the National Center for Biotechnology Information (NCBI) databank revealed a second potential SNP variant; the second variant was identified in a 1.5 individual (three chromosome) analysis. The first SNP variant (V128I) was located in the first IgV-like domain, whereas the NCBI SNP variant (L221F) was located in the second IgC-like domain.

Figure 9B:
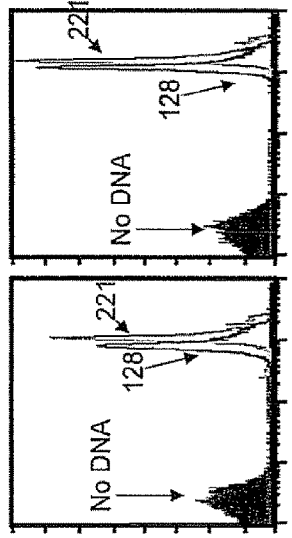
FIG. 9B shows similar binding efficacy of 16H and 5D antibodies to a B7RP1 SNP variant.

As discussed above, both the 16H and 5D monoclonal antibodies bind to the first IgV-like domain, this it is unlikely that the latter L221F variant affects either 16H or 5D mAb binding or function. Nonetheless, to determine if either of these SNP variants affects 16H or 5D binding and/or function, two different experiments were conducted. In the first set of experiments, avidin fusion proteins were constructed with the two SNP variants and tested for binding to 16H or 5D antibodies in the flow cytometric assay as described above. These representative mAbs from the H and D epitope classes bound to the SNP variants with similar efficacy as the wild-type B7RP-1 (FIG. 9B). These data suggested that antibodies from both the H and D epitope classes bind to the B7RP-1 SNP variants.

Figure 9C:
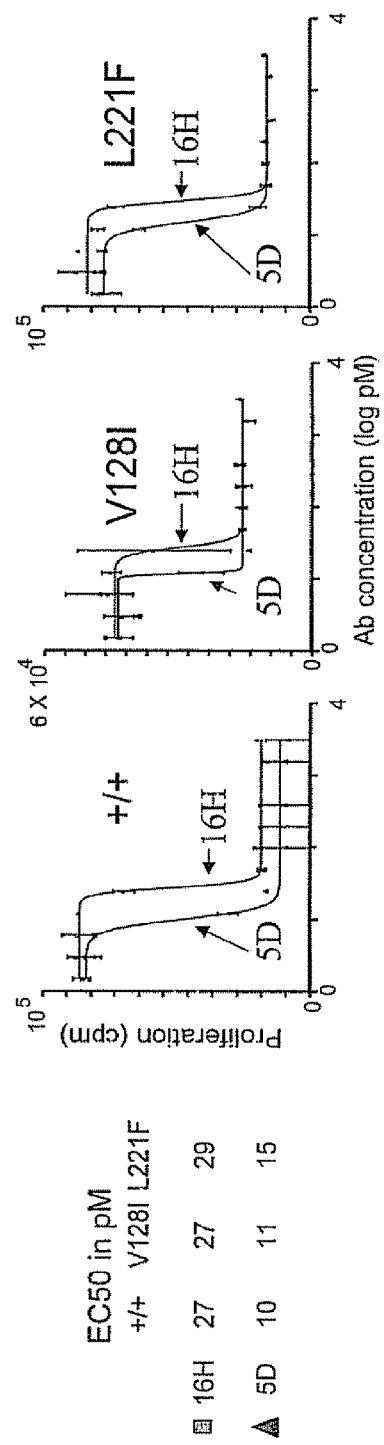
FIG. 9C depicts the results of co-stimulation assays with 16H or 5D antibodies and SNP variants.

In the second approach, Fc fusion proteins were constructed using the B7RP-1 SNP variant sequences and compared for the ability of these proteins to stimulate T cells in the plate co-stimulation assay (FIG. 9C). Both the 16H and 5D antibodies inhibited co-stimulation mediated by the SNP variant Fc fusion proteins with similar EC$_{50}$s as the wild-type fusion protein. Taken together these data indicated that the two potential B7RP-1 SNP variants were recognized by the antibodies of the invention. Thus, the antibodies of the invention can bind to target in patients containing these SNP variants.

Example 10

In Vivo Animal Efficacy Models

The ability of B7RP-1 antibodies to inhibit immune response was analyzed using a murinized rat anti-murine B7RP-1 monoclonal antibody (1B7v2) and challenging BALB/c mice with keyhole-limpet hemocyanin (KLH).

Generation of the Murinized Rat Anti-Murine B7RP-1 Monoclonal Antibody 1B7v2

A Chinese-Hamster-Ovary cell line that overexpressed a full-length murine B7RP-1 was injected into rats as a primary immunization, and subsequently with a murine B7RP-1-Fc fusion protein to boost the immune response. Spleens were harvested 3 or 4 days post-intravenous boost and the splenic B cells fused with the Y3-Ag1.2.3 rat myeloma line (ATCC CRL-1631). Cells were then selected in media supplemented with hypoxanthine-aminopterin-thymidine (HAT) for 2 weeks and subsequently single-cell subcloned by limiting dilution. These procedures are described in "Practical Immunology, 2nd ed." Leslie Hudson and Frank C. Hay; Blackwell Scientific Publications 1980.

Genes encoding the 1B7 immunoglobulin were cloned from the 1B7 cell line using standard procedures (Sambrook et al, 2001, MOLECULAR CLONING: A LABORATORY MANUAL., 3d ed., Cold Spring Harbor Laboratory Press, Cold Spring Harbor, N.Y). The isotype switch of the human anti-huB7RP1 MAbs was accomplished by cloning the variable region fragments containing XbaI and BsmBI restriction site cohesive ends into the pDSRa vector with the human IgG1 or huIgG2 constant region which also had XbaI and BsmBI ends. For the 1B7 rat anti-muB7RP1 the chimera was formed by a three step overlapping PCR process. The rat variable region was PCR amplified with a 3' primer that contained part, ~25-35 nucleotides, of the murine constant region. The murine constant region was amplified with a 5' primer that contained part, ~25-35 nucleotides, of the rat variable region. The two fragments were then used as template and the 5' rat variable region (XbaI containing) and the murine 3' constant region (SalI containing) primers were used to generate a complete light chain or heavy chain. The light chain and heavy chain PCR products were then digested with XbaI and SalI and cloned into pDSRa19. A total of 25 µg of linearized DNA (12.5 µg pDC323B LC+12.5 µg pDC324 HC) were transfected into CS-9 cells using electroporation and selected on DHFR-supplemented medium.

Figure 10A:
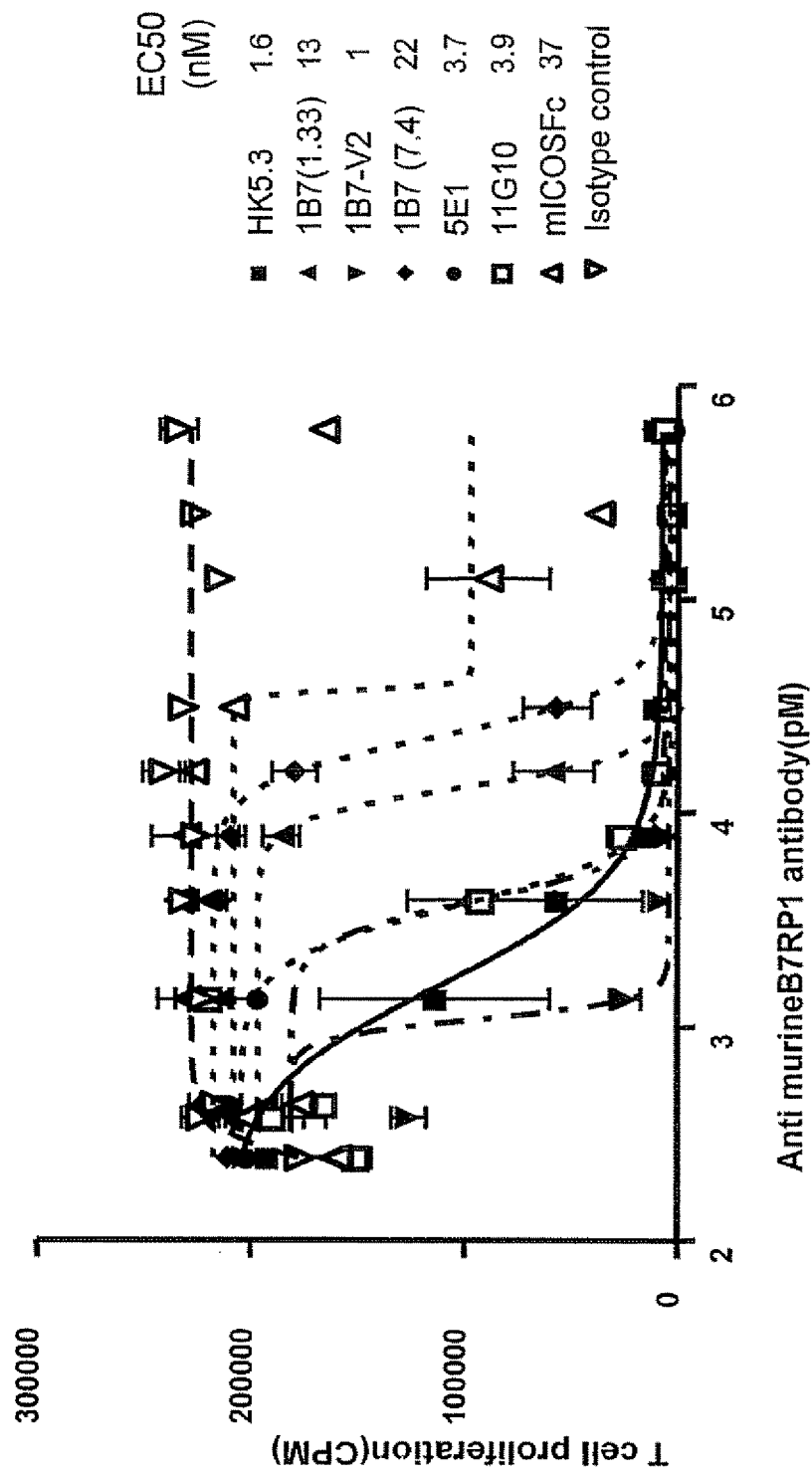
FIG. 10A shows plate co-stimulation assay results with 1B7v2 monoclonal antibodies compared with a number of different anti-murine B7RP-1 monoclonal antibodies.

To test the efficacy of the 1B7v2 mAb, plate co-stimulation assays were conducted with this mAb. The results were compared with other anti-murine B7RP-1 mAbs (FIG. 10A). As discussed above, 1B7 is the original hybridoma-produced mAb; two different preparations (labeled 1.33 and 7.4) were tested. 5E1 and 11G10 were other anti-mB7RP-1 monoclonals generated in the fusions described above. Finally, HK5.3 was a commercially-available anti-mB7RP-1 (ebiosciences #16-5985-85).

The 1B7v2 mAb blocked T cell activation in this assay equal to or better than any of the other mAbs, and thus was selected as the surrogate therapeutic for further studies.

Antigen Challenge in Mice

Keyhole Limpet Hemocyanin (KLH) was purchased from Pierce Biotechnology (Rockford, Ill.). Dosing solution #1 (KLH 5 mg/kg in 1 mg/mouse ALUM) was prepared with equal parts of 2×ALUM (500 mg of ALUM plus 50 ml PBS (phosphate buffered saline)) and 2×KLH (2.0 ml dH20 (RNAse-Free) mixed with 20 mg of lyophilized KLH, brought to 20 ml with 1×PBS). Dosing solution #2 (KLH 1 mg/kg in 1 mg/mouse ALUM) was prepared with 1 part 2×KLH mixed with 4 parts 1× phosphate buffered saline.

Female BALB/c mice were primed either with 1 mg/kg of KLH/alum and re-immunized on day 21 with 5 mg/kg KLH only, introduced by intraperitoneal injection. Mice were treated by intraperitoneal injection with 1B7v.2, the isotype control antibody (anti-AGP3 PB) or the vehicle (PBS) alone, starting on day 1 (one day prior to priming with KLH/alum) in a final volume of 200 µl every 5 days.

The mice were bled every 7 days retro-orbitally (approximately 200 µl) to obtain approximately 50-100 µl of serum for analysis of antigen-specific serum IgM (FIG. 10B), IgG2a (FIG. 10C), and IgG1 (FIG. 10D). Both the isotype-control and vehicle-treated mice showed significant primary and secondary immune responses. The IgM response was not affected by treatment, whereas, blockade of B7RP-1-ICOS with 1B7v2 decreased both primary and secondary IgG2a and IgG1 responses in a statistically-significant manner.

Figure 11:
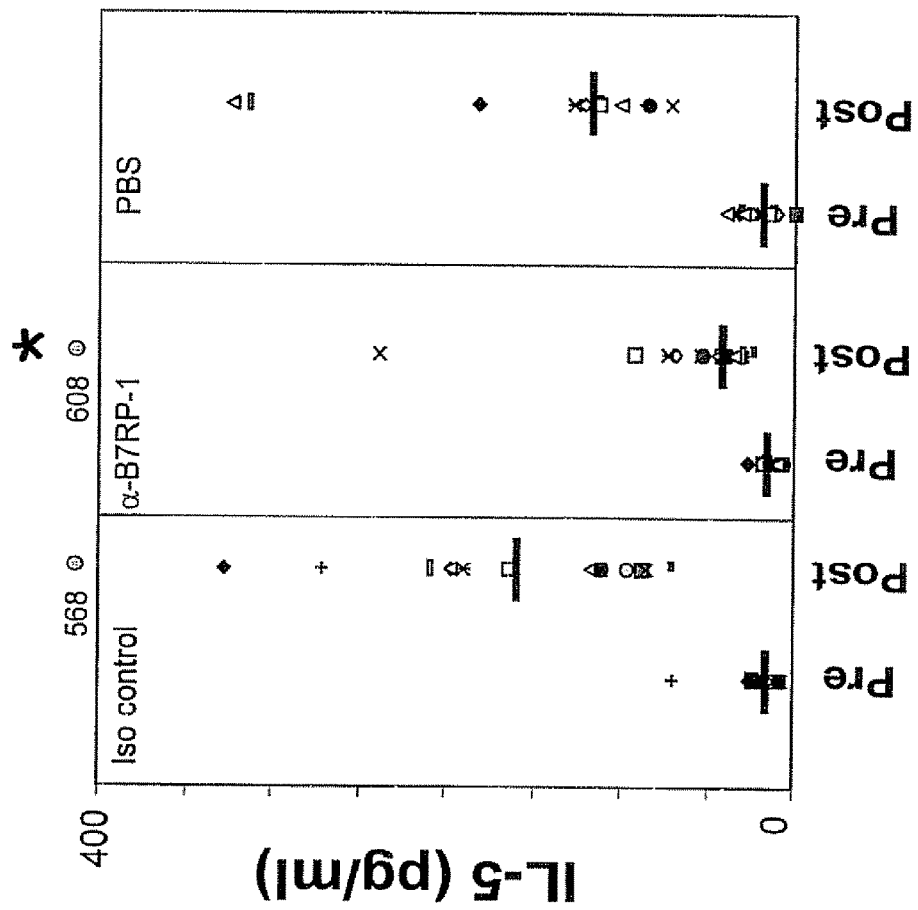
FIG. 11 depicts ELISA results demonstrating that serum IL-5 levels are repressed by 1B7v2 antibodies.

IL-5 is a cytokine released by T cells in response to antigen stimulation that induces B cell differentiation and function. As the B7RP-1/ICOS interaction is believed to be critical for T-cell-dependent B cell function, measuring serum IL-5 levels was used to determine if interdiction of the B7RP-1/ICOS axis was indeed affecting T cell function. As expected, blockade of B7RP-1 also inhibited antigen-induced serum IL-5 levels. Sera were harvested from the mice from the antigen challenge experiment outlined above 24 hours after the antigen challenge on day 21, and serum IL-5 levels were determined by ELISA. As shown in FIG. 11, elevated IL-5 levels were detected in the test mice as early as 9 hours after challenge; levels began to decline by 48 hours and returned to baseline by 72 hours. Treatment of the mice with 1B7v2 mAb lead to a statistically significant repression of IL-5 levels at the 24-hour time point.

Example 11

Binding to Cynomolgus Monkey B7RP-1

Figure 12A:
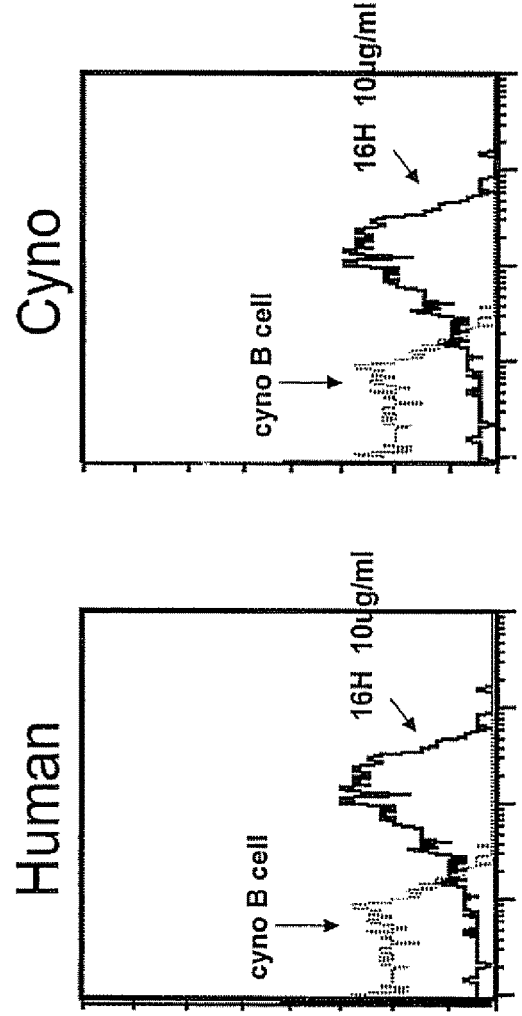
FIG. 12A shows that 16H antibodies can bind to cynomolgus monkey B7RP1 (right panel) and human B7RP1 (left panel).
Figure 12B:
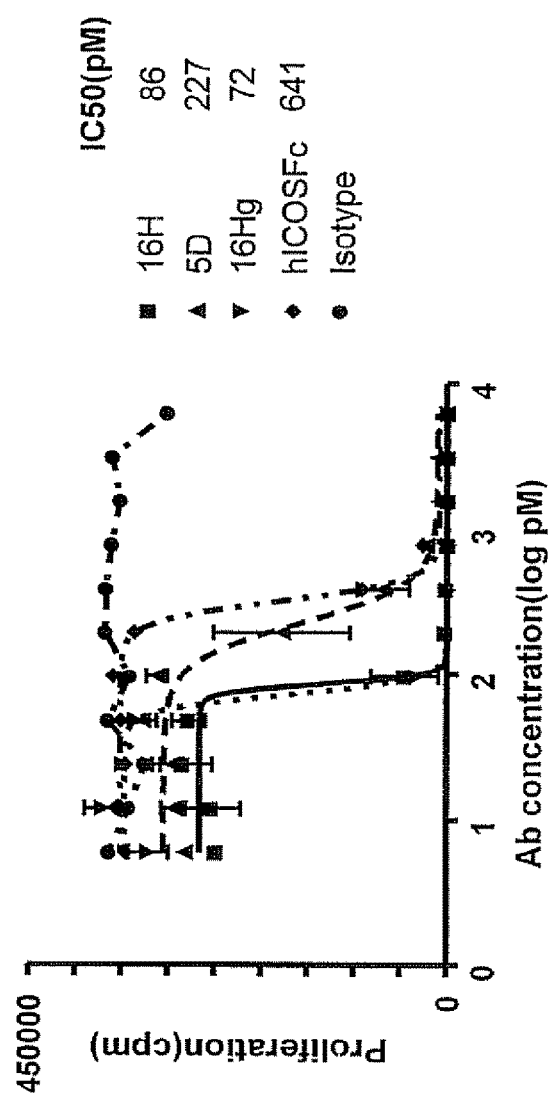
FIG. 12B shows that 16H, 16Hg, and 5D antibodies can inhibit cynomolgus monkey B7RP1/ICOS-dependent T cell activation.

To determine if the anti-hB7RP-1 mAbs also bind to cynomolgus monkey B7RP-1, flow cytometric staining experiments were conducted with the 16H mAb and B cells purified from cynomolgus monkeys and humans. As shown in FIG. 12A, addition of fluorescently-labeled 16H to cyno B cells lead to staining, indicating that 16H was indeed binding to cyno B7RP-1 (right panel). As expected, 16H also stained human B cells (left panel). In addition, 16H, 16Hg, and 5D were tested in plate co-stimulation assays using cyno T cells, cyno B7RP-1-Fc, and anti-CD3 mAb. As shown in FIG. 12B, all three mAbs inhibited cyno B7RP-1-dependent cyno T cell activation, indicating that these mAbs functionally block the cyno ICOS-B7RP-1 interaction.

Example 12

T-Cell Dependent Antigen Responses in the Cynomolgus Monkey Following Administration of the Anti-B7RP-1 Antibodies A cynomolgus monkey study was conducted with two anti-B7RP-1 monoclonal antibodies, 16H and 5D, to assess the ability of these antibodies to inhibit a T-cell dependent B cell antigen response as determined by serum levels of antigen-specific antibody. Briefly, the anti-keyhole limpet hemocyanin (KLH) and anti-tetanus toxoid antibody responses were examined following antigen challenge in the presence of B7RP-1 antibodies in the cynomolgus monkey.

Test Article 1 was 16H and Test Article 2 was 5D. The Control Article was the vehicle for B7RP-1 antibody (0.01 sodium acetate, pH 5.0, 5% sorbitol, 0.004% Tween 20). Keyhole Limpet Hemocyanin (KLH) was purchased from Pierce Biotechnology (Rockford, Ill.).

The KLH was prepared by reconstitution with sterile water to yield a 10 mg/mL stock solution. The stock solution was diluted with sterile water to yield a 1 mg/mL dosing solution. Tetanus Toxoid used for these experiments was Super-Tet® Tetanus Toxoid w/Havlogen®, purchased from Intervet™ Inc. (Milsboro, Del.). The dose level for these experiments was 75 IU (0.5 mL of 150 IU/mL).

Table 6 shows the treatment group distribution of 28 cynomolgus monkeys.

TABLE 6

| Group No. | Number of Males/ Females | Test Article | Route | Dose Level (mg/kg) | Dose Volume (mL/kg) | Dose Solution Conc. (mg/mL) |
| --- | --- | --- | --- | --- | --- | --- |
| 1 | 2/2 | Control | IV | 0 | 1 | 0 |
| 2 | 2/2 | B7RP-1 5D | IV | 0.1 | 1 | 0.1 |
| 3 | 2/2 | B7RP-1 5D | IV | 1.0 | 1 | 1.0 |
| 4 | 2/2 | B7RP-1 5D | IV | 8.0 | 1 | 10.0 |
| 5 | 2/2 | B7RP-1 16H | IV | 0.1 | 1 | 0.1 |
| 6 | 2/2 | B7RP-1 16H | IV | 1.0 | 1 | 1.0 |
| 7 | 2/2 | B7RP-1 16H | IV | 8.0 | 1 | 10.0 |

Test article doses were administered via intravenous injection to all animals on Days 1, 8, 15, 22, 29, 36, 43, and 50. Animals scheduled for necropsy in Groups 1-4 (1/sex/group) received an additional dose on Day 57. Evaluation of immune response was conducted on all animals via immunization with KLH and tetanus toxoid antigens followed by blood sampling for antigen-specific immunoglobulins (IgM and IgG).

Titer values were present following primary administration of both the KLH and tetanus antigens. For KLH, primary titer values ranged from 0 to 900 for both IgM and IgG. As the primary KLH challenge was administered prior to test article administration, no effect of the B7RP-1 antibodies was evaluated. For tetanus toxoid, primary titer values ranged from 0 to 50 for IgM and from 0 to 4050 for IgG. There were no differences in the primary response to tetanus toxoid between the B7RP-1 antibody groups and the control group.

As expected, titer values for IgG were increased following secondary administration of both the KLH and tetanus antigens, when compared to the primary titer values. For KLH, secondary titer values ranged from 0 to 300 for IgM and from 0 to 8100 for IgG. However, there was no evidence of inhibition of the KLH secondary response attributed to administration of the B7RP-1 antibodies.

For tetanus toxoid, secondary titer values were below 50 for IgM and ranged from 1350 to 36450 for IgG. Results for individual animal and group mean values are presented in the FIG. 13A (16H antibody) and FIG. 13B (5D antibody) for Days 53 and 57 following the secondary challenge with tetanus toxoid on Day 42.

On Day 53, the number of animals reaching peak response was 3/4, 1/4, and 1/4 at the 0.1, 1, and 8 mg/kg dose levels of 16H, respectively, and 1/4, 1/4, and 1/4 at the 0.1, 1, and 8 mg/kg dose levels of 5D respectively, compared to 2/4 control animals. Thus, in general, the number of animals reaching a high titer on Day 53 was reduced in the B7RP-1 antibody-treated groups. On Day 57, titer values were maintained in the control animals, while titer values for several of the B7RP-1 antibody-treated animals declined from the Day 53 values. The number of animals with high titers on Day 57 was 0/4, 0/4, and 1/4 at the 0.1, 1, and 8 mg/kg dose levels of 16H, respectively, and 0/4, 0/4, and 0/4 at the 0.1, 1, and 8 mg/kg dose levels of 5D respectively, compared to 2/4 control animals.

These results demonstrated that the two B7RP-1 antibodies 16H and 5D inhibited a T-cell dependent B cell antigen response in cynomolgus monkeys, as determined by serum levels of tetanus toxoid-specific antibody. In addition, the presence of the B7RP-1 antibodies was important for blockage of the B7RP-1-ICOS Interaction during the primary response in order to detect an effect following the secondary challenge.

These results and the results from Example 10 demonstrated that both the surrogate therapeutic and the therapeutic candidates blocked T and B cell-dependent immune responses in murine and monkey model systems, which indicated that blocking this co-stimulatory axis may be efficacious in the treatment of B-cell-mediated diseases such as Systemic Lupus Erythematosus (SLE), asthma, and Rheumatoid Arthritis (RA).

It should be understood that the foregoing disclosure emphasizes certain specific embodiments of the invention and that all modifications or alternatives equivalent thereto are within the spirit and scope of the invention as set forth in the appended claims.

We claim:

1. A method of treating an autoimmune disease or inflammatory response in a patient, comprising administering to a patient a pharmaceutically effective amount of an isolated antibody that binds specifically to human B7RP1, wherein the antibody comprises an amino acid sequence as set forth in any of SEQ ID NO: 1-14, 29, 32, 34, 37, 38, 40, 44-58, or 70-76, or an antigen-binding or an immunologically functional immunoglobulin fragment thereof.

2. The method of claim 1 wherein the autoimmune disease or inflammatory response is asthma, rheumatoid arthritis, or systemic Lupus erythematosus.

3. The method of claim 1, wherein the isolated antibody or immunologically functional immunoglobulin fragment thereof is formulated in a pharmaceutical composition.

4. The method of claim 1, wherein the isolated antibody or immunologically functional immunoglobulin fragment thereof competes with the anti-B7RP1 antibody comprising a heavy chain sequence set forth in SEQ ID NOS: 44, 46, 70, or 71 and a light chain sequence set forth in SEQ ID NO: 45, or the anti-B7RP1 antibody comprising a heavy chain sequence set forth in SEQ ID NOS: 47 or 72 and a light chain sequence set forth in SEQ ID NO: 48 for binding to human B7RP1 and inhibiting the activity of the B7RP1.

5. The method of claim 4, wherein the autoimmune disease or inflammatory response is rheumatoid arthritis, systemic Lupus erythematosus, or asthma.

6. The method of claim 4, wherein the isolated antibody or immunologically functional immunoglobulin fragment thereof is formulated in a pharmaceutical composition.

7. The method of claim 1, wherein the isolated antibody or antigen-binding or immunologically functional immunoglobulin fragment thereof comprises an amino acid sequence as set forth in any of SEQ ID NOs: 44-58 or 70-76, and wherein the antibody or fragment thereof inhibits the activity of human B7RP1.

8. The method of claim 7, wherein the autoimmune disease or inflammatory response is rheumatoid arthritis, systemic Lupus erythematosus, or asthma.

9. A method of treating an autoimmune disease or inflammatory response in a patient, comprising administering to a patient a pharmaceutical composition comprising a human B7RP1 binding agent comprising SEQ ID NOs:
  (a) 15, 16, and 17;
  (b) 18, 19, and 20;
  (c): 15, 21 and 22;
  (d) 18, 19 and 20;
  (e) 18, 19, and 23;
  (f) 24, 16, and 25;
  (g) 15, 16, and 26;
  (h) 27, 28, and 29;
  (i) 27, 33, and 34;
  (j) 30, 31, and 32;
  (k) 35, 36, and 37;
  (l) 27, 33, and 38;
  (m) 35, 39, and 40;
  (n) 15, 16, 17, 27, 28, and 29;
  (o) 18, 19, 20, 30, 31, and 32;
  (p) 15, 21, 22, 27, 33, and 34;
  (q) 18, 19, 23, 35, 36, and 37;
  (r) 24, 16, 25, 27, 33, and 38;
  (s) 15, 16, 26, 35, 39, and 40;
  (t) 29;
  (u) 29 and 27;
  (v) 29 and 28;
  (w) 29, 27, and 28;
  (x) 34;
  (y) 34, and 27;
  (z) 34 and 33;
  (aa) 34, 27, and 33;
  (bb) 32;
  (cc) 32 and 30;
  (dd) 32 and 31;
  (ee) 32, 30, and 31;
  (ff) 37;
  (gg) 37 and 35;
  (hh) 37 and 36;
  (ii) 37, 35, and 36;

(jj) 38;
(kk) 38 and 27;
(ll) 38, 27, and 33;
(mm) 40;
(nn) 40 and 35;
(oo) 40 and 39; or
(pp) 40, 35, and 39.

10. The method of claim 9, wherein the autoimmune disease or inflammatory response is rheumatoid arthritis, systemic Lupus erythematosus, or asthma.

11. A method of treating a condition caused by increased expression of human B7RP1 or increased sensitivity to human B7RP1 in a patient, comprising administering to the patient a pharmaceutical composition comprising a pharmaceutically acceptable carrier and a therapeutically effective amount of an isolated human antibody that binds specifically to human B7RP1, wherein the antibody comprises an amino acid sequence as set forth in any of SEQ ID NOs: 1-14, 29, 32, 34, 37, 38, 40, 44-58 or 70-76, or an antigen-binding or immunologically functional immunoglobulin fragment thereof, and wherein the antibody or fragment thereof inhibits human B7RP1 activity.

12. A method of inhibiting co-stimulatory signal T-cell activation in a patient, comprising administering to a patient a pharmaceutically effective amount of an isolated human antibody that binds specifically to human B7RP1, wherein the antibody comprises an amino acid sequence as set forth in any of SEQ ID NO: 1-14, 29, 32, 34, 37, 38, 40 44-58 or 70-76, or an antigen-binding or an immunologically functional immunoglobulin fragment thereof.

* * * * *

UNITED STATES PATENT AND TRADEMARK OFFICE
CERTIFICATE OF CORRECTION

PATENT NO.       : 10,072,090 B2
APPLICATION NO.  : 14/995983
DATED            : September 11, 2018
INVENTOR(S)      : Gerald Siu et al.

Page 1 of 1

It is certified that error appears in the above-identified patent and that said Letters Patent is hereby corrected as shown below:

On the Title Page

At Item (71), Applicants should be –Amgen Inc., Thousand Oaks, CA (US); Medarex Inc., Princeton, NJ (US)–

Signed and Sealed this
Seventeenth Day of March, 2020

Andrei Iancu
*Director of the United States Patent and Trademark Office*

SEQUENCE LISTING

<160> NUMBER OF SEQ ID NOS: 76

<210> SEQ ID NO 1
<211> LENGTH: 107
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile

```
                35                  40                  45
Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asp Ser Tyr Pro Arg
                 85                  90                  95

Thr Phe Gly Gln Gly Thr Lys Val Glu Ile Lys
            100                 105

<210> SEQ ID NO 2
<211> LENGTH: 107
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Asn Trp Pro Trp
                 85                  90                  95

Thr Phe Gly Gln Gly Thr Lys Val Glu Ile Lys
            100                 105

<210> SEQ ID NO 3
<211> LENGTH: 107
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Trp
                20                  25                  30

Leu Ala Trp Tyr Gln Gln Lys Pro Glu Lys Ala Pro Lys Ser Leu Ile
            35                  40                  45

Tyr Thr Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
            100                 105

<210> SEQ ID NO 4
<211> LENGTH: 108
<212> TYPE: PRT
<213> ORGANISM: Homo sapiens

<400> SEQUENCE: 4
```

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ala
                85                  90                  95

Leu Thr Phe Gly Gly Gly Thr Lys Val Glu Ile Lys
            100                 105

<210> SEQ ID NO 5
<211> LENGTH: 107
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Arg
                85                  90                  95

Thr Phe Gly Gln Gly Thr Lys Val Glu Ile Lys
            100                 105

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Phe Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105
```

<210> SEQ ID NO 7
<211> LENGTH: 121
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Ile Leu Val Thr Val Ser Ser
        115                 120

<210> SEQ ID NO 8
<211> LENGTH: 121
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser
        115                 120

<210> SEQ ID NO 9
<211> LENGTH: 121
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Ala Asp Ser Val
 50                  55                  60

Glu Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Phe Tyr Cys
                85                  90                  95

Ala Arg Asp Leu Asn Ile Met Val Trp Gly Ile Phe Asp Tyr Trp Gly
            100                 105                 110

Gln Gly Thr Leu Val Thr Val Ser Ser
        115                 120

<210> SEQ ID NO 10
<211> LENGTH: 121
<212> TYPE: PRT
<213> ORGANISM: Homo sapiens

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Val Gly Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95

Ala Arg Asp Gly Ile Leu Trp Phe Gly Asp Ile Pro Thr Tyr Trp Gly
            100                 105                 110

Gln Gly Ile Leu Val Thr Val Ser Ser
        115                 120

<210> SEQ ID NO 11
<211> LENGTH: 121
<212> TYPE: PRT
<213> ORGANISM: Homo sapiens

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95

Ala Arg Asp Gly Ile Leu Trp Phe Gly Asp Ile Pro Thr Tyr Trp Gly
            100                 105                 110

```
Gln Gly Thr Leu Val Thr Val Ser Ser
        115                 120

<210> SEQ ID NO 12
<211> LENGTH: 120
<212> TYPE: PRT
<213> ORGANISM: Homo sapiens

<400> SEQUENCE: 12

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Met Tyr Tyr Cys Ala
                85                  90                  95

Lys Ser Gly Val Pro Leu Leu Trp Phe Gly Glu Phe Tyr Trp Gly Gln
            100                 105                 110

Gly Thr Leu Val Thr Val Ser Ser
        115                 120

<210> SEQ ID NO 13
<211> LENGTH: 121
<212> TYPE: PRT
<213> ORGANISM: Homo sapiens

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Leu Trp Phe Gly Asp Leu Pro Thr Tyr Trp Gly
            100                 105                 110

Gln Gly Thr Leu Val Thr Val Ser Ser
        115                 120

<210> SEQ ID NO 14
<211> LENGTH: 118
<212> TYPE: PRT
<213> ORGANISM: Homo sapiens

<400> SEQUENCE: 14

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
```

```
                    20                  25                  30
Ala Met His Trp Val Arg Gln Ala Pro Gly Lys Gly Leu Glu Trp Val
            35                  40                  45

Ser Ala Ile Gly Ala Gly Gly Thr Tyr Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Val Val Val Val Gly Phe Phe Asp Tyr Trp Gly Gln Gly Thr
            100                 105                 110

Leu Val Thr Val Ser Ser
        115
```

<210> SEQ ID NO 15
<211> LENGTH: 11
<212> TYPE: PRT
<213> ORGANISM: Homo sapiens

<400> SEQUENCE: 15

```
Arg Ala Ser Gln Gly Ile Ser Asn Trp Leu Ala
1               5                   10
```

<210> SEQ ID NO 16
<211> LENGTH: 7
<212> TYPE: PRT
<213> ORGANISM: Homo sapiens

<400> SEQUENCE: 16

```
Ala Ala Ser Ser Leu Gln Ser
1               5
```

<210> SEQ ID NO 17
<211> LENGTH: 9
<212> TYPE: PRT
<213> ORGANISM: Homo sapiens

<400> SEQUENCE: 17

```
Gln Gln Tyr Asp Ser Tyr Pro Arg Thr
1               5
```

<210> SEQ ID NO 18
<211> LENGTH: 11
<212> TYPE: PRT
<213> ORGANISM: Homo sapiens

<400> SEQUENCE: 18

```
Arg Ala Ser Gln Ser Val Ser Ser Tyr Leu Ala
1               5                   10
```

<210> SEQ ID NO 19
<211> LENGTH: 7
<212> TYPE: PRT
<213> ORGANISM: Homo sapiens

<400> SEQUENCE: 19

```
Asp Ala Ser Asn Arg Ala Thr
1               5
```

<210> SEQ ID NO 20
<211> LENGTH: 9
<212> TYPE: PRT

<213> ORGANISM: Homo sapiens

<400> SEQUENCE: 20

Gln Gln Arg Asn Asn Trp Pro Trp Thr
1               5

<210> SEQ ID NO 21
<211> LENGTH: 7
<212> TYPE: PRT
<213> ORGANISM: Homo sapiens

<400> SEQUENCE: 21

Thr Ala Ser Ser Leu Gln Ser
1               5

<210> SEQ ID NO 22
<211> LENGTH: 9
<212> TYPE: PRT
<213> ORGANISM: Homo sapiens

<400> SEQUENCE: 22

Gln Gln Tyr Asn Ser Tyr Pro Arg Thr
1               5

<210> SEQ ID NO 23
<211> LENGTH: 10
<212> TYPE: PRT
<213> ORGANISM: Homo sapiens

<400> SEQUENCE: 23

Gln Gln Arg Ser Asn Trp Pro Ala Leu Thr
1               5                   10

<210> SEQ ID NO 24
<211> LENGTH: 11
<212> TYPE: PRT
<213> ORGANISM: Homo sapiens

<400> SEQUENCE: 24

Arg Ala Ser Gln Gly Ile Ser Ser Trp Leu Ala
1               5                   10

<210> SEQ ID NO 25
<211> LENGTH: 9
<212> TYPE: PRT
<213> ORGANISM: Homo sapiens

<400> SEQUENCE: 25

Gln Gln Tyr Asn Thr Tyr Pro Arg Thr
1               5

<210> SEQ ID NO 26
<211> LENGTH: 9
<212> TYPE: PRT
<213> ORGANISM: Homo sapiens

<400> SEQUENCE: 26

Gln Gln Tyr Asn Ser Tyr Pro Tyr Thr
1               5

<210> SEQ ID NO 27
<211> LENGTH: 5
<212> TYPE: PRT
<213> ORGANISM: Homo sapiens

```
<400> SEQUENCE: 27

Ser Tyr Trp Met Ser
1               5

<210> SEQ ID NO 28
<211> LENGTH: 17
<212> TYPE: PRT
<213> ORGANISM: Homo sapiens

<400> SEQUENCE: 28

Tyr Ile Lys Gln Asp Gly Asn Glu Lys Tyr Tyr Val Asp Ser Val Lys
1               5                   10                  15

Gly

<210> SEQ ID NO 29
<211> LENGTH: 12
<212> TYPE: PRT
<213> ORGANISM: Homo sapiens

<400> SEQUENCE: 29

Glu Gly Ile Leu Trp Phe Gly Asp Leu Pro Thr Phe
1               5                   10

<210> SEQ ID NO 30
<211> LENGTH: 5
<212> TYPE: PRT
<213> ORGANISM: Homo sapiens

<400> SEQUENCE: 30

Ser Tyr Gly Met His
1               5

<210> SEQ ID NO 31
<211> LENGTH: 17
<212> TYPE: PRT
<213> ORGANISM: Homo sapiens

<400> SEQUENCE: 31

Val Ile Trp Tyr Asp Gly Ser Lys Lys Tyr Tyr Ala Asp Ser Val Glu
1               5                   10                  15

Gly

<210> SEQ ID NO 32
<211> LENGTH: 12
<212> TYPE: PRT
<213> ORGANISM: Homo sapiens

<400> SEQUENCE: 32

Asp Leu Asn Ile Met Val Trp Gly Ile Phe Asp Tyr
1               5                   10

<210> SEQ ID NO 33
<211> LENGTH: 17
<212> TYPE: PRT
<213> ORGANISM: Homo sapiens

<400> SEQUENCE: 33

Tyr Ile Lys Gln Asp Gly Ser Glu Lys Tyr Tyr Val Asp Ser Val Lys
1               5                   10                  15

Gly

<210> SEQ ID NO 34
```

```
<211> LENGTH: 12
<212> TYPE: PRT
<213> ORGANISM: Homo sapiens

<400> SEQUENCE: 34

Asp Gly Ile Leu Trp Phe Gly Asp Ile Pro Thr Tyr
1               5                   10

<210> SEQ ID NO 35
<211> LENGTH: 5
<212> TYPE: PRT
<213> ORGANISM: Homo sapiens

<400> SEQUENCE: 35

Ser Tyr Ala Met His
1               5

<210> SEQ ID NO 36
<211> LENGTH: 16
<212> TYPE: PRT
<213> ORGANISM: Homo sapiens

<400> SEQUENCE: 36

Ala Ile Gly Thr Gly Gly Gly Thr Tyr Tyr Ala Asp Ser Val Lys Gly
1               5                   10                  15

<210> SEQ ID NO 37
<211> LENGTH: 11
<212> TYPE: PRT
<213> ORGANISM: Homo sapiens

<400> SEQUENCE: 37

Gly Val Pro Leu Leu Trp Phe Gly Glu Phe Tyr
1               5                   10

<210> SEQ ID NO 38
<211> LENGTH: 12
<212> TYPE: PRT
<213> ORGANISM: Homo sapiens

<400> SEQUENCE: 38

Asp Gly Ile Leu Trp Phe Gly Asp Leu Pro Thr Tyr
1               5                   10

<210> SEQ ID NO 39
<211> LENGTH: 16
<212> TYPE: PRT
<213> ORGANISM: Homo sapiens

<400> SEQUENCE: 39

Ala Ile Gly Ala Gly Gly Gly Thr Tyr Tyr Ala Asp Ser Val Lys Gly
1               5                   10                  15

<210> SEQ ID NO 40
<211> LENGTH: 10
<212> TYPE: PRT
<213> ORGANISM: Homo sapiens

<400> SEQUENCE: 40

Val Val Val Val Val Gly Phe Phe Asp Tyr
1               5                   10

<210> SEQ ID NO 41
<211> LENGTH: 326
<212> TYPE: PRT
```

<213> ORGANISM: Homo sapiens

<400> SEQUENCE: 41

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 42
<211> LENGTH: 330
<212> TYPE: PRT
<213> ORGANISM: Homo sapiens

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 43
<211> LENGTH: 107
<212> TYPE: PRT
<213> ORGANISM: Homo sapiens

<400> SEQUENCE: 43

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 44
<211> LENGTH: 447
<212> TYPE: PRT
<213> ORGANISM: Homo sapiens

<400> SEQUENCE: 44

Glu Val Gln Leu Val Glu Ser Gly Gly Gly Leu Val Gln Pro Gly Gly
  1               5                  10                  15

Ser Leu Arg Leu Ser Cys Ala Gly Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Tyr Ile Lys Gln Asp Gly Asn Glu Lys Tyr Tyr Val Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
             85                  90                  95

Ala Arg Glu Gly Ile Leu Trp Phe Gly Asp Leu Pro Thr Phe Trp Gly
            100                 105                 110

Gln Gly Ile Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335
```

```
Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 45
<211> LENGTH: 214
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 447
<212> TYPE: PRT
<213> ORGANISM: Homo sapiens

<400> SEQUENCE: 46
```

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445
```

<210> SEQ ID NO 47
<211> LENGTH: 451
<212> TYPE: PRT
<213> ORGANISM: Homo sapiens

<400> SEQUENCE: 47

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Lys Lys Tyr Tyr Ala Asp Ser Val
    50                  55                  60
Glu Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Phe Tyr Cys
                85                  90                  95
Ala Arg Asp Leu Asn Ile Met Val Trp Gly Ile Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
```

```
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 48
<211> LENGTH: 214
<212> TYPE: PRT
<213> ORGANISM: Homo sapiens

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 433
<212> TYPE: PRT
<213> ORGANISM: Homo sapiens

<400> SEQUENCE: 49
```

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Ala Ser Thr Lys Gly
            100                 105                 110

Pro Ser Val Phe Pro Leu Ala Pro Cys Ser Arg Ser Thr Ser Glu Ser
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Asn Phe Gly Thr Gln Thr Tyr Thr Cys Asn Val
            180                 185                 190

Asp His Lys Pro Ser Asn Thr Lys Val Asp Lys Thr Val Glu Arg Lys
        195                 200                 205

Cys Cys Val Glu Cys Pro Pro Cys Pro Ala Pro Pro Val Ala Gly Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255

Pro Glu Val Gln Phe Asn Trp Tyr Val Asp Gly Val Glu Val His Asn
            260                 265                 270

Ala Lys Thr Lys Pro Arg Glu Glu Gln Phe Asn Ser Thr Phe Arg Val
        275                 280                 285

Val Ser Val Leu Thr Val Val His Gln Asp Trp Leu Asn Gly Lys Glu
    290                 295                 300

Tyr Lys Cys Lys Val Ser Asn Lys Gly Leu Pro Ala Pro Ile Glu Lys
305                 310                 315                 320

Thr Ile Ser Lys Thr Lys Gly Gln Pro Arg Glu Pro Gln Val Tyr Thr
                325                 330                 335

Leu Pro Pro Ser Arg Glu Glu Met Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Met Leu
    370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415
```

Ala Leu His Asn His Tyr Thr Gln Lys Ser Leu Ser Leu Ser Pro Gly
            420                 425                 430

Lys

<210> SEQ ID NO 50
<211> LENGTH: 214
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 447
<212> TYPE: PRT
<213> ORGANISM: Homo sapiens

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

-continued

Ala Arg Asp Gly Ile Leu Trp Phe Gly Asp Ile Pro Thr Tyr Trp Gly
            85                  90                  95
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
                195                 200                 205

Lys Pro Ser Asn Thr Lys Val Asp Lys Thr Val Glu Arg Lys Cys Cys
        210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 52
<211> LENGTH: 444
<212> TYPE: PRT
<213> ORGANISM: Homo sapiens

<400> SEQUENCE: 52

Glu Val Gln Leu Val Gln Ser Gly Gly Gly Leu Val His Pro Gly Gly
1               5                   10                  15

```
Ser Leu Arg Leu Ser Cys Ala Gly Ser Gly Phe Thr Phe Ser Ser Tyr
         20                  25                  30

Ala Met His Trp Val Arg Gln Ala Pro Gly Lys Gly Leu Glu Trp Val
         35                  40                  45

Ser Ala Ile Gly Ala Gly Gly Thr Tyr Tyr Ala Asp Ser Val Lys
     50                  55                  60

Gly Arg Phe Thr Ile Ser Arg Asp Asn Ala Lys Asn Ser Leu Tyr Leu
65                   70                  75                  80

Gln Met Asn Ser Leu Arg Ala Glu Asp Met Ala Val Tyr Tyr Cys Ala
                 85                  90                  95

Arg Val Val Val Val Gly Phe Phe Asp Tyr Trp Gly Gln Gly Thr
                100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Asn Phe Gly Thr Gln Thr Tyr Thr Cys Asn Val Asp His Lys Pro Ser
            195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
    275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
```

<210> SEQ ID NO 53
<211> LENGTH: 214
<212> TYPE: PRT
<213> ORGANISM: Homo sapiens

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 54
<211> LENGTH: 447
<212> TYPE: PRT
<213> ORGANISM: Homo sapiens

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Leu Trp Phe Gly Asp Leu Pro Thr Tyr Trp Gly

```
              100                 105                 110
    Gln Gly Thr Leu Val Thr Val Ser Ser Ala Ser Thr Lys Gly Pro Ser
              115                 120                 125

Val Phe Pro Leu Ala Pro Cys Ser Arg Ser Thr Ser Glu Ser Thr Ala
              130                 135                 140

Ala Leu Gly Cys Leu Val Lys Asp Tyr Phe Pro Glu Pro Val Thr Val
    145                 150                 155                 160

Ser Trp Asn Ser Gly Ala Leu Thr Ser Gly Val His Thr Phe Pro Ala
                        165                 170                 175

Val Leu Gln Ser Ser Gly Leu Tyr Ser Leu Ser Ser Val Val Thr Val
                        180                 185                 190

Pro Ser Ser Asn Phe Gly Thr Gln Thr Tyr Thr Cys Asn Val Asp His
                        195                 200                 205

Lys Pro Ser Asn Thr Lys Val Asp Lys Thr Val Glu Arg Lys Cys Cys
                        210                 215                 220

Val Glu Cys Pro Pro Cys Pro Ala Pro Pro Val Ala Gly Pro Ser Val
    225                 230                 235                 240

Phe Leu Phe Pro Pro Lys Pro Lys Asp Thr Leu Met Ile Ser Arg Thr
                        245                 250                 255

Pro Glu Val Thr Cys Val Val Val Asp Val Ser His Glu Asp Pro Glu
                        260                 265                 270

Val Gln Phe Asn Trp Tyr Val Asp Gly Val Glu Val His Asn Ala Lys
                        275                 280                 285

Thr Lys Pro Arg Glu Glu Gln Phe Asn Ser Thr Phe Arg Val Val Ser
                        290                 295                 300

Val Leu Thr Val Val His Gln Asp Trp Leu Asn Gly Lys Glu Tyr Lys
    305                 310                 315                 320

Cys Lys Val Ser Asn Lys Gly Leu Pro Ala Pro Ile Glu Lys Thr Ile
                        325                 330                 335

Ser Lys Thr Lys Gly Gln Pro Arg Glu Pro Gln Val Tyr Thr Leu Pro
                        340                 345                 350

Pro Ser Arg Glu Glu Met Thr Lys Asn Gln Val Ser Leu Thr Cys Leu
                        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
    385                 390                 395                 400

Asp Gly Ser Phe Phe Leu Tyr Ser Lys Leu Thr Val Asp Lys Ser Arg
                        405                 410                 415

Trp Gln Gln Gly Asn Val Phe Ser Cys Ser Val Met His Glu Ala Leu
                        420                 425                 430

His Asn His Tyr Thr Gln Lys Ser Leu Ser Leu Ser Pro Gly Lys
                        435                 440                 445

<210> SEQ ID NO 55
<211> LENGTH: 214
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30
```

```
Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Thr Tyr Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 56
<211> LENGTH: 446
<212> TYPE: PRT
<213> ORGANISM: Homo sapiens

<400> SEQUENCE: 56

Glu Val Gln Leu Val Gln Ser Gly Gly Gly Leu Val His Pro Gly Gly
 1               5                  10                  15

Ser Leu Arg Leu Ser Cys Ala Gly Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ser Ala Ile Gly Thr Gly Gly Thr Tyr Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Met Ala Met Tyr Tyr Cys Ala
                 85                  90                  95

Lys Ser Gly Val Pro Leu Leu Trp Phe Gly Glu Phe Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

-continued

```
Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 57
<211> LENGTH: 450
<212> TYPE: PRT
<213> ORGANISM: Homo sapiens

<400> SEQUENCE: 57

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Met Tyr Tyr Cys Ala
                85                  90                  95

Lys Ser Gly Val Pro Leu Leu Trp Phe Gly Glu Phe Tyr Trp Gly Gln
            100                 105                 110

Gly Thr Leu Val Thr Val Ser Ser Ala Ser Thr Lys Gly Pro Ser Val
```

```
            115                 120                 125
Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 58
<211> LENGTH: 215
<212> TYPE: PRT
<213> ORGANISM: Homo sapiens

<400> SEQUENCE: 58

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Lys Pro Gly Gln Ala Pro Arg Leu Leu Ile
             35                  40                  45
Tyr Asp Ala Ser Asn Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Ala
                 85                  90                  95
Leu Thr Phe Gly Gly Gly Thr Lys Val Glu Ile Lys Arg Thr Val Ala
            100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
            195                 200                 205
Ser Phe Asn Arg Gly Glu Cys
            210                 215

<210> SEQ ID NO 59
<211> LENGTH: 24
<212> TYPE: DNA
<213> ORGANISM: Homo sapiens
<220> FEATURE:
<221> NAME/KEY: misc_feature
<222> LOCATION: (18)..(23)
<223> OTHER INFORMATION: n is a, c, g, or t

<400> SEQUENCE: 59
ggccggatag gcctccannn nnnt                                            24

<210> SEQ ID NO 60
<211> LENGTH: 21
<212> TYPE: DNA
<213> ORGANISM: Homo sapiens

<400> SEQUENCE: 60
ggggtcaggc tggaactgag g                                               21

<210> SEQ ID NO 61
<211> LENGTH: 19
<212> TYPE: DNA
<213> ORGANISM: Homo sapiens

<400> SEQUENCE: 61
tgaggacgct gaccacacg                                                  19

<210> SEQ ID NO 62
<211> LENGTH: 54
<212> TYPE: DNA
<213> ORGANISM: Homo sapiens

<400> SEQUENCE: 62
cagcagaagc ttctagacca ccatggacat gagggtcctc gctcagctcc tggg           54
```

<210> SEQ ID NO 63
<211> LENGTH: 34
<212> TYPE: DNA
<213> ORGANISM: Homo sapiens

<400> SEQUENCE: 63
cttgtcgact caacactctc ccctgttgaa gctc         34

<210> SEQ ID NO 64
<211> LENGTH: 43
<212> TYPE: DNA
<213> ORGANISM: Homo sapiens

<400> SEQUENCE: 64
acaacaaagc ttctagacca ccatggagtt ggggctgaac tgg         43

<210> SEQ ID NO 65
<211> LENGTH: 32
<212> TYPE: DNA
<213> ORGANISM: Homo sapiens

<400> SEQUENCE: 65
gtggaggcac tagagacggt gaccaggatt cc         32

<210> SEQ ID NO 66
<211> LENGTH: 228
<212> TYPE: PRT
<213> ORGANISM: Homo sapiens

<400> SEQUENCE: 66

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
                20                  25                  30

Tyr Val Tyr Trp Gln Thr Ser Glu Ser Lys Thr Val Thr Tyr His
            35                  40                  45

Ile Pro Gln Asn Ser Ser Leu Glu Asn Val Asp Ser Arg Tyr Arg Asn
        50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile

Thr Glu Asn Pro
225

<210> SEQ ID NO 67
<211> LENGTH: 139
<212> TYPE: PRT
<213> ORGANISM: Homo sapiens

<400> SEQUENCE: 67

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
                20                  25                  30

Tyr Val Tyr Trp Gln Thr Ser Glu Ser Lys Thr Val Val Thr Tyr His
            35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr
    130                 135

<210> SEQ ID NO 68
<211> LENGTH: 127
<212> TYPE: PRT
<213> ORGANISM: Homo sapiens

<400> SEQUENCE: 68

Leu Gly Phe Gln Glu Val Leu Ser Val Glu Val Thr Leu His Val Ala
1               5                   10                  15

Ala Asn Phe Ser Val Pro Val Val Ser Ala Pro His Ser Pro Ser Gln
                20                  25                  30

Asp Glu Leu Thr Phe Thr Cys Thr Ser Ile Asn Gly Tyr Pro Arg Pro
            35                  40                  45

Asn Val Tyr Trp Ile Asn Lys Thr Asp Asn Ser Leu Leu Asp Gln Ala
    50                  55                  60

Leu Gln Asn Asp Thr Val Phe Leu Asn Met Arg Gly Leu Tyr Asp Val
65                  70                  75                  80

Val Ser Val Leu Arg Ile Ala Arg Thr Pro Ser Val Asn Ile Gly Cys
                85                  90                  95

Cys Ile Glu Asn Val Leu Leu Gln Gln Asn Leu Thr Val Gly Ser Gln
            100                 105                 110

Thr Gly Asn Asp Ile Gly Glu Arg Asp Lys Ile Thr Glu Asn Pro
        115                 120                 125

<210> SEQ ID NO 69
<211> LENGTH: 39
<212> TYPE: DNA
<213> ORGANISM: Homo sapiens

<400> SEQUENCE: 69
cgacggagca cgaggacacg acaggacgaa ggagagaaa        39

<210> SEQ ID NO 70
<211> LENGTH: 451
<212> TYPE: PRT
<213> ORGANISM: Homo sapiens

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Ile Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

```
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 71
<211> LENGTH: 451
<212> TYPE: PRT
<213> ORGANISM: Homo sapiens

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 72
<211> LENGTH: 447
<212> TYPE: PRT
<213> ORGANISM: Homo sapiens

<400> SEQUENCE: 72

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Lys Tyr Tyr Ala Asp Ser Val
        50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Phe Tyr Cys
                85                  90                  95

Ala Arg Asp Leu Asn Ile Met Val Trp Gly Ile Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

```
Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 73
<211> LENGTH: 451
<212> TYPE: PRT
<213> ORGANISM: Homo sapiens

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Val Gly Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Leu Trp Phe Gly Asp Ile Pro Thr Tyr Trp Gly
            100                 105                 110

Gln Gly Ile Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 74
<211> LENGTH: 451
<212> TYPE: PRT
<213> ORGANISM: Homo sapiens

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
```

```
                35                  40                  45
Ala Tyr Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Leu Trp Phe Gly Asp Ile Pro Thr Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450
```

-continued

<210> SEQ ID NO 75
<211> LENGTH: 448
<212> TYPE: PRT
<213> ORGANISM: Homo sapiens

<400> SEQUENCE: 75

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Ala Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Val Val Val Val Gly Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser

```
              370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 76
<211> LENGTH: 451
<212> TYPE: PRT
<213> ORGANISM: Homo sapiens

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Leu Trp Phe Gly Asp Leu Pro Thr Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

-continued

| | | | | | | | | | | | | | |
|---|---|---|---|---|---|---|---|---|---|---|---|---|---|
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Pro | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |
| Tyr | Thr | Leu | Pro | Pro | Ser | Arg | Asp | Glu | Leu | Thr | Lys | Asn | Gln | Val | Ser |
| | | 355 | | | | | 360 | | | | | 365 | | | |
| Leu | Thr | Cys | Leu | Val | Lys | Gly | Phe | Tyr | Pro | Ser | Asp | Ile | Ala | Val | Glu |
| | | 370 | | | | 375 | | | | | 380 | | | | |
| Trp | Glu | Ser | Asn | Gly | Gln | Pro | Glu | Asn | Asn | Tyr | Lys | Thr | Thr | Pro | Pro |
| 385 | | | | | 390 | | | | | 395 | | | | | 400 |
| Val | Leu | Asp | Ser | Asp | Gly | Ser | Phe | Phe | Leu | Tyr | Ser | Lys | Leu | Thr | Val |
| | | | | 405 | | | | | 410 | | | | | 415 | |
| Asp | Lys | Ser | Arg | Trp | Gln | Gln | Gly | Asn | Val | Phe | Ser | Cys | Ser | Val | Met |
| | | | 420 | | | | | 425 | | | | | 430 | | |
| His | Glu | Ala | Leu | His | Asn | His | Tyr | Thr | Gln | Lys | Ser | Leu | Ser | Leu | Ser |
| | | | 435 | | | | 440 | | | | | 445 | | | |
| Pro | Gly | Lys | | | | | | | | | | | | | |
| | | 450 | | | | | | | | | | | | | |